(12) United States Patent
Bazan et al.

(10) Patent No.: US 11,458,142 B2
(45) Date of Patent: Oct. 4, 2022

(54) COMPOSITIONS AND METHODS FOR AMELIORATING PAIN

(71) Applicants: The Board of Supervisors of Louisiana State University and Agricultural and Mechanical College, Baton Rouge, LA (US); UNIVERSITY OF ALCALA DE HENARES, Madrid (ES)

(72) Inventors: Nicolas Bazan, New Orleans, LA (US); Hernan Bazan, New Orleans, LA (US); Julio Alvarez-Builla, Madrid (ES); Dennis Paul, New Orleans, LA (US); Carolina Burgos, Madrid (ES)

(73) Assignees: The Board of Supervisors of Louisiana State University and Agricultural and Mechanical College, Baton Rouge, LA (US); University of Alcala De Henares, Madrid (ES); South Rampart Pharma, LLC, New Orleans, LA (US)

( * ) Notice: Subject to any disclaimer, the term of this patent is extended or adjusted under 35 U.S.C. 154(b) by 37 days.

(21) Appl. No.: 16/641,401

(22) PCT Filed: Mar. 12, 2018

(86) PCT No.: PCT/US2018/022029
§ 371 (c)(1),
(2) Date: Feb. 24, 2020

(87) PCT Pub. No.: WO2019/040122
PCT Pub. Date: Feb. 28, 2019

(65) Prior Publication Data
US 2020/0179393 A1 Jun. 11, 2020

Related U.S. Application Data

(60) Provisional application No. 62/550,137, filed on Aug. 25, 2017.

(51) Int. Cl.
| | | |
|---|---|---|
| *A61K 31/5375* | (2006.01) |
| *A61P 23/00* | (2006.01) |
| *A61K 31/18* | (2006.01) |
| *A61K 31/40* | (2006.01) |
| *A61K 31/4402* | (2006.01) |
| *A61K 31/495* | (2006.01) |
| *A61K 45/06* | (2006.01) |
| *A61P 29/00* | (2006.01) |
| *C07C 311/19* | (2006.01) |

(52) U.S. Cl.
CPC .......... *A61K 31/5375* (2013.01); *A61K 31/18* (2013.01); *A61K 31/40* (2013.01); *A61K 31/4402* (2013.01); *A61K 31/495* (2013.01); *A61K 45/06* (2013.01); *A61P 23/00* (2018.01); *A61P 29/00* (2018.01); *C07C 311/19* (2013.01)

(58) Field of Classification Search
CPC .... A61K 31/5375; A61K 31/18; A61K 31/40; A61K 31/4402; A61K 31/495; A61K 45/06; A61P 23/00; A61P 29/00
See application file for complete search history.

(56) References Cited

U.S. PATENT DOCUMENTS 6,806,291 B1  10/2004  Sunkel et al.

FOREIGN PATENT DOCUMENTS

| CN | 104230762 | 12/2014 |
| CN | 108299255 | 7/2018 |
| EA | 006430 | 12/2005 |
| JP | 2011231094 | 11/2011 |
| WO | 2005/035485 | 4/2005 |
| WO | 2008/021896 | 2/2008 |
| WO | 2008/118758 | 10/2008 |
| WO | 2010/085352 | 7/2010 |
| WO | 2017/034872 | 3/2017 |
| WO | 2019/040122 | 2/2019 |

OTHER PUBLICATIONS

Reddy et al. "A Facile and Green synthesis of novel imide and amidic acid derivatives of phenacetin as potential analgesic and anti-pyretic agents." Letters in Organic Chemistry 10.1 (2013). 70-76.
Reddy et al. "Green approach for drug design and discovery of paracetamol analogues as potential analgesic and antipyretic agents." Green Chemistry Letters and Reviews 7.1 (2014): 24-31.
Remington's Pharmaceutical Sciences. 16th ed., Mack Publishing, Easton Pa, (1980).
Reuben, A. et al., Outcomes in Adults with Acute Liver Failure Between 1998 and 2013: An Observational Cohort Study, Annals of internal medicine, 164 (2016) 724-732.
Rodrigues, R.M, et al., Toxicogenomics-based prediction of acetaminophen-induced liver injury using human hepatic sell systems, Toxicology letters, 240 (2016) 50-59.
Santoh, M., et al., Acetaminophen analog N-acetyl-m-aminophenol, but not its reactive metabolite, N-acetyl-p-benzoquinone imine induces CYP3A activity via inhibition of protein degradation, Biochemical and biophysical research communications, 486 (2017) 639-644.
Sinning, C., et al., New analgesics synthetically derived from the paracetamol metabolite N-(4-hydroxyphenyl)4(5Z, 8Z, 11Z, 14Z)-icosatetra-5, 8, 11, 14-enamide, Journal of medicinal chemistry, 51 (2008) 7800-7805.
Vaccarino, A.L., et al., Synthesis and in vivo evaluation of non0-pheatotoxic acetaminophen analogs, Biorrg Med Chem, 15 (2007) 2206-2215.
Williams et al., Emerging Molecular Approaches to Pain Therapy, J. of Medicinal Chem. 42:1481-1485 (1999).
Written Opinion of the Int'l Search Authority for PCT/US2018/022029 dated Aug. 8, 2018.
International Search Report for PCT/US18/22029 dated Aug. 8, 2018.

(Continued)

Primary Examiner — Alicia L Otton
(74) Attorney, Agent, or Firm — Baker Donelson

(57) ABSTRACT

This invention is directed to compositions, methods and kits that can be used for the treatment or amelioration of pain.

23 Claims, 20 Drawing Sheets

(56) References Cited

OTHER PUBLICATIONS

A. Bertolini, A., et al., Paracetamol: new vistas of an old drug. CNS Drug Rev, 12 (2006) 250-275.
Abdel-Alim et al., Synthesis and Anti-Inflammatory Testing of Some New Compounds Incorporating 5-Aminosalicyclic Acid (5-ASA) as Potential Prodrugs, Archives of Pharmacal Research, 2005, vol. 28, No. 6, pp. 637-647.
Abdelmegeed, M. A., et al., Role of cytochrome P450 2E1 in protein nitration and ubiquitin-mediated degradation during acetaminophen toxicity, Biochemical pharmacology, 79 (2010) 57-66.
Bernal, William, et al "Acute liver failure." The Lancet 376.9736 (2010); 190-201.
Bessems, J.G and Vermeulen, N.P, Paracetamol (acetaminophen)-induced toxicity: molecular and biochemical mechanisms, analogues and protective approaches, Crit Reve Toxicol, 31 (2001) 55-138.
Blieden, M., et al., A perspective on the epidemiology of acetaminophen exposure and toxicity in the United States, Expert Reve Clin Pharmacol, 7 (2014) 341-348.
Brodie, B.B and Axelrod, J., The fate and acetanilide in man, The Journal of pharmacology and experimental therapeutics, 94 (1948) 29-38.
Brune, K., et al., Acetaminophen/paracetamol: A history of errors, failures and false decisions, European journal of pain, 19 (2015) 250-275.
Cui, J.G, et al., Allodynia and hyperalgesia suppression by a novel analgesic in experimental neuropathic pain, Biochemical and biophysical research communications, 350 (2006) 358-363.
Dani, M., et al., The local antinociceptive effects of paracetamol in neuropathic pain are mediated by cannabinoid receptors, European journal of pharmacology, 573 (2007) 214-215.
Flower, R.J and Vane, J.R. Inhibition of prostaglandin synthetase in brain explains the antipyretic activity of paracetamol (4-acetamidophenol), Nature, 240 (1972) 410-411.
Fresno, N., et al., Adamantyl analogues of paracetamol as potent analgesic drugs via inhibition of TRPA1, PloS one, 9 (2014) e113841.
Gamal, W., et al., Low-dose acetaminophen induces early disruption of cell-cell tight junctions in human hepatic cells and mouse liver, Scientific reports, 7 (2017) 37541.
Harrison's Principles of Internal Medicine, pp. 93-98 (Wilson et al., ed., 12th ed. 1991).
Hinson, J.A., et al,. Acetaminophen-induced hepatoxicity: role of metabolic activation, reactive oxygen-nitrogen species, and mitochondrial permeability transition, Drug Metab Rev. 36 (2004) 805-822.
Hogestatt, E.D., et al., Conversion of acetaminophen to the bioactive N-acylphenolamine AM404 via fatty acid amide hydrolase-dependent arachidonic acid conjugation in the nervous system. The Journal of biological chemistry, 280 (2005) 31405-31412.
Larson, A.M., et al., Acute Liver Failure Study, Acetaminophen-induced acute liver failure: results of a United States multicenter, prospective study, Hepatology, 42 (2005) 1364-1372.
LeCluyse, E.L., et al., R.P. Witek, M.E. Andersen, M.J. Powers, Organotypic liver culture models: meeting current challenges in toxicity testing, Crit Reve Toxicol, 42 (2012) 501-548.
Mallat, C. et al., TRPV1 in brain is involved in acetaminophen-induced antinociception, PloS one, 5 (2010).
Mason, R.P., and V. Fisher. Federation proceedings. vol. 45. No. 10, 1986.
McGill, M.R., et al., Acetaminophen-induced liver injury in rats and mice: comlparison of protein adducts, mitochondrial dysfunction, and oxidative stress in the mechanism of toxicity, Toxicology and applied pharmacology, 264 (2012) 387-394.
Mercola, FDA Finally Changes Prescription Recommendations for High-Dose ApAP, 2014.
Miao, L., et al, First Multi-gram Preparation SCP-123, A Novel Water-Soluble Analgesic, Org Process Res Dev, 130 (2009) 820.
Mitchell et al., (1983) Effects of oral contraceptive steroids on acetaminophen metabolism and elimination. Clin. Pharmacol. Ther., Jul. 1983, pp. 48-53.
Mitchell, J. R., et al. (1973). "Acetaminophen-induced hepatic necrosis. I. Role of drug metabolism." J Pharmacol Exp Ther 187(1): 185-194.
Neuberger et al., 1980. Long-term ingestion of paracetamol and liver disease. Journal of the Royal Society of Medivine. vol. 73. pp. 701-707.
Ouellet, M. and Percival, M.D., Mechanism of acetaminophen inhibition of cyclooxygenase isoforms, Archives of biochemistry and biophysics, 387 (2001) 273-280.
Rodrigues, R.M, et al., Toxicogenomics-based prediction of acetaminophen-induced liver injury using human hepatic cell systems, Toxicology letters, 240 (2016) 50-59.
Written Opinion of the Int'l Search Authority for PCT/US2018/022029 dated Aug. 18, 2018.
Guidelines for conducting preclinical studies of drugs. Part One.—Moscow: Grif and K, 2012.—944 p., Ed. Mironov A. N. see Chapter 12, pp. 197-218.
N.A.Shostak, N.G. Pravdyuk: "Pain as an interdisciplinary problem", Clinician, 2, 2012, pp. 5-8.
M.D. Mashkovsky "Medicines", Moscow, "Medicine", 1993, part I, p. 8.
V.G. Belikov "Pharmaceutical chemistry", textbook, 2007,Moscow, publishing house "MEDpress-inform", pp. 27-29.
Dyson G., May P. "Chemistry of Synthetic Drugs", translation from English: publishing house "Mir", 1964, pp. 12-19).

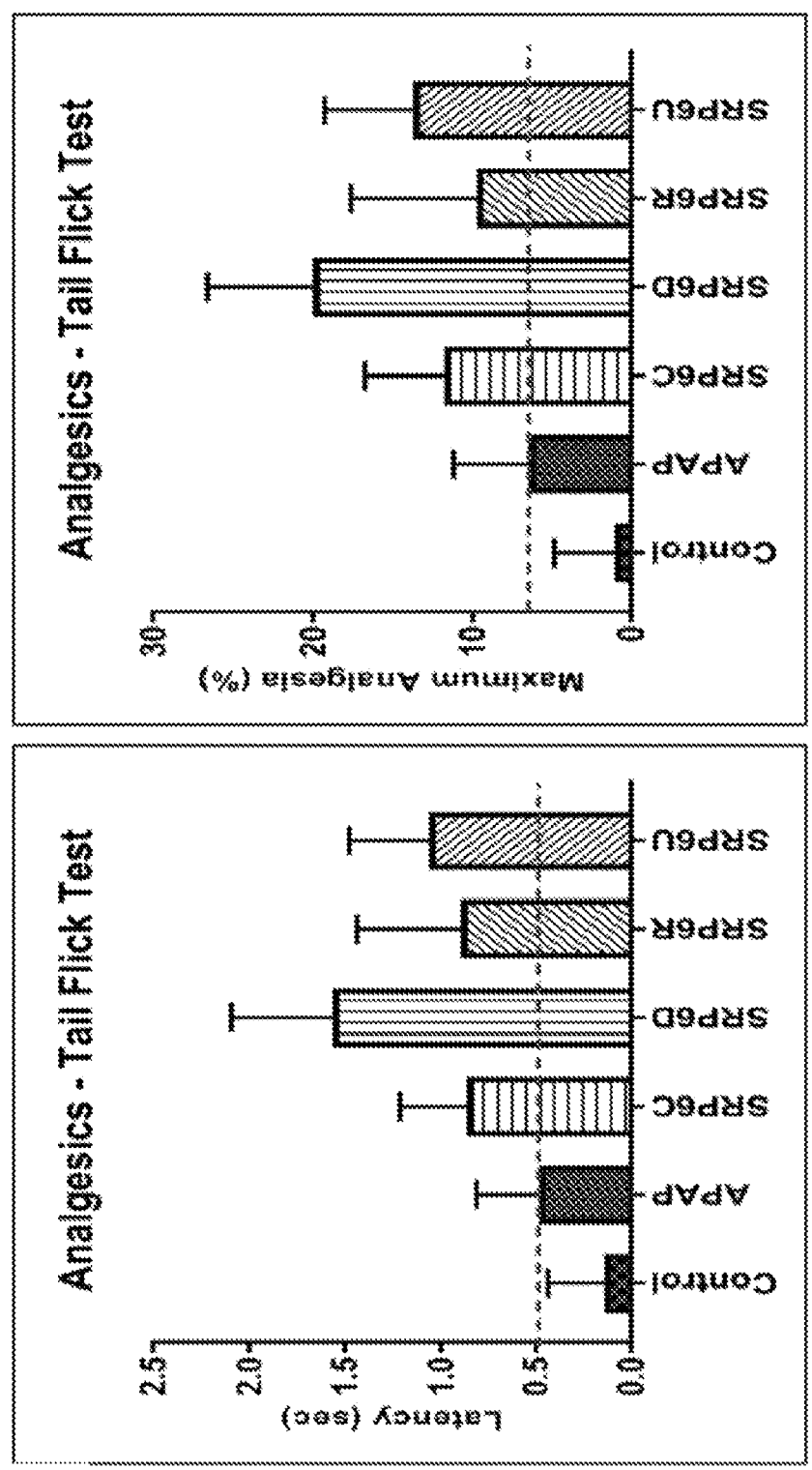
FIG. 1 - CONT.

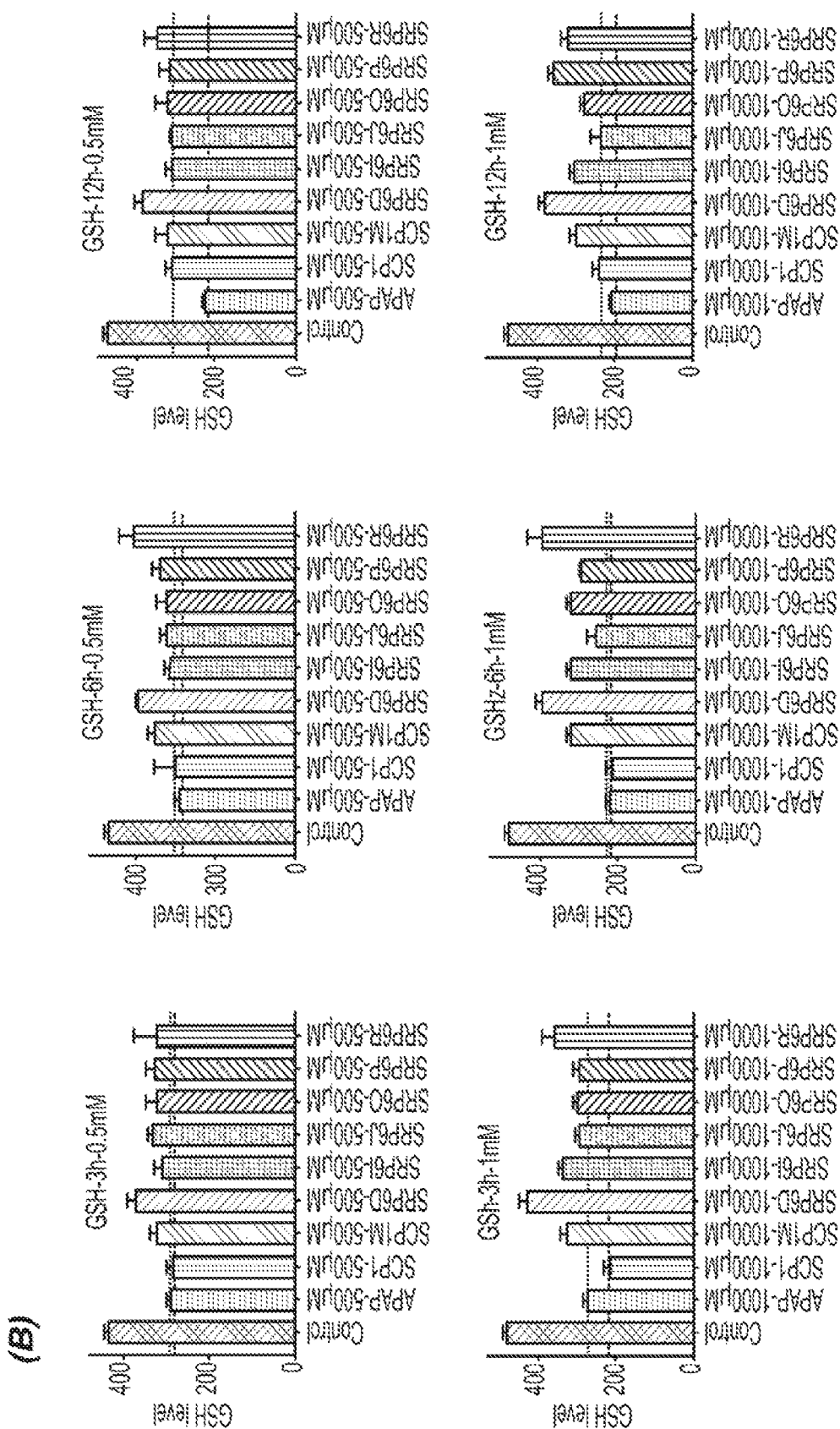
FIG. 3 - CONT.

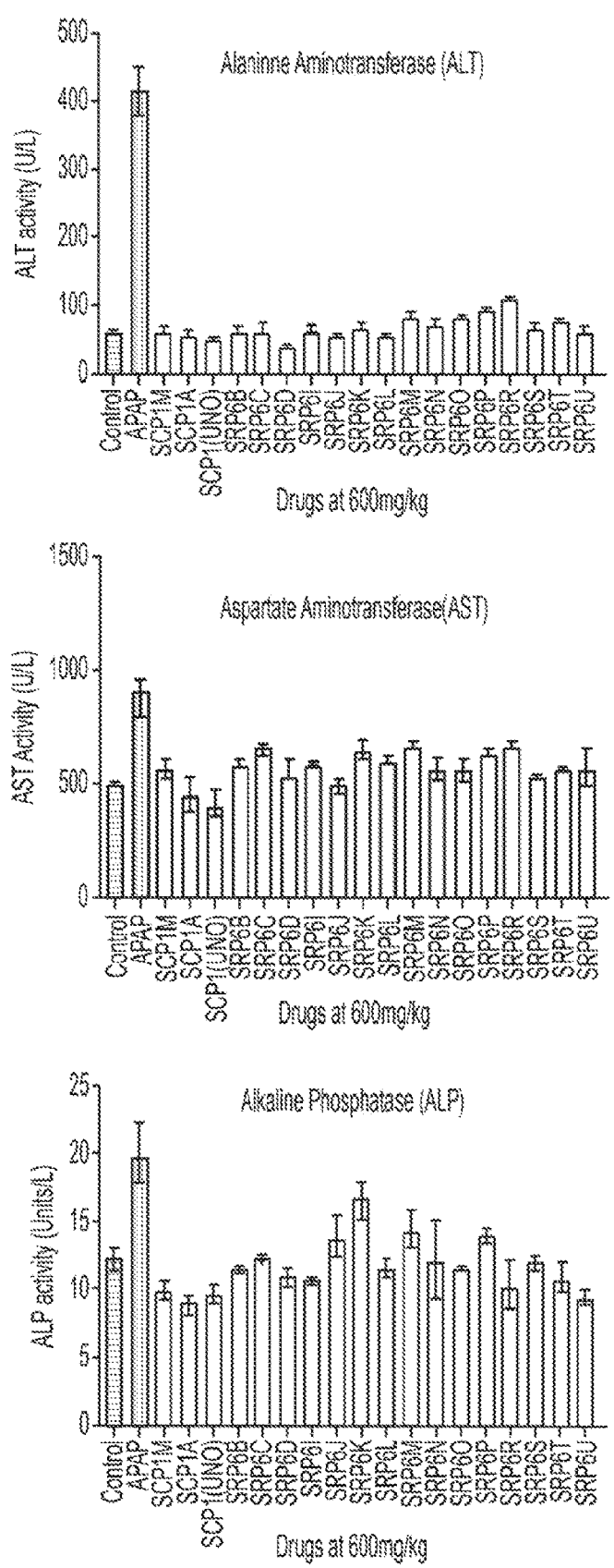
FIG. 3 - CONT.

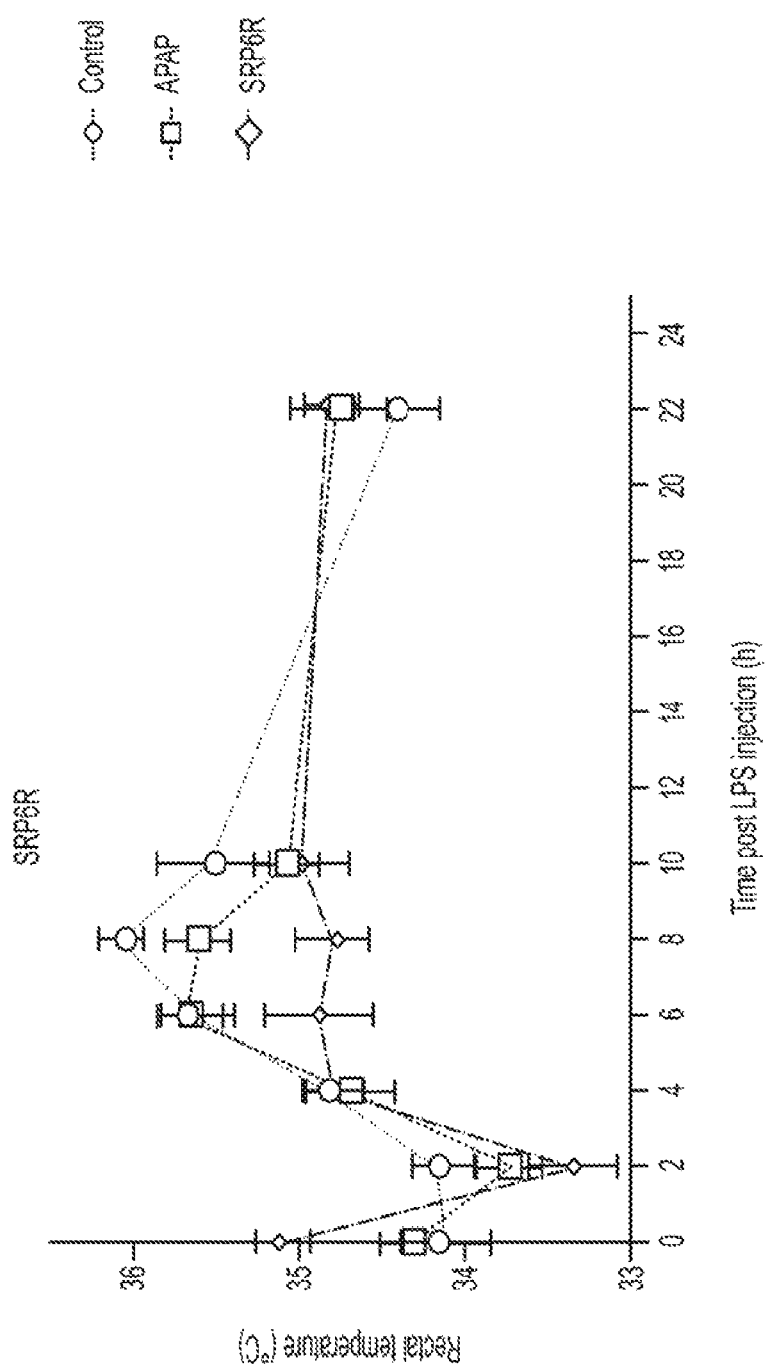
FIG. 4 - CONT.

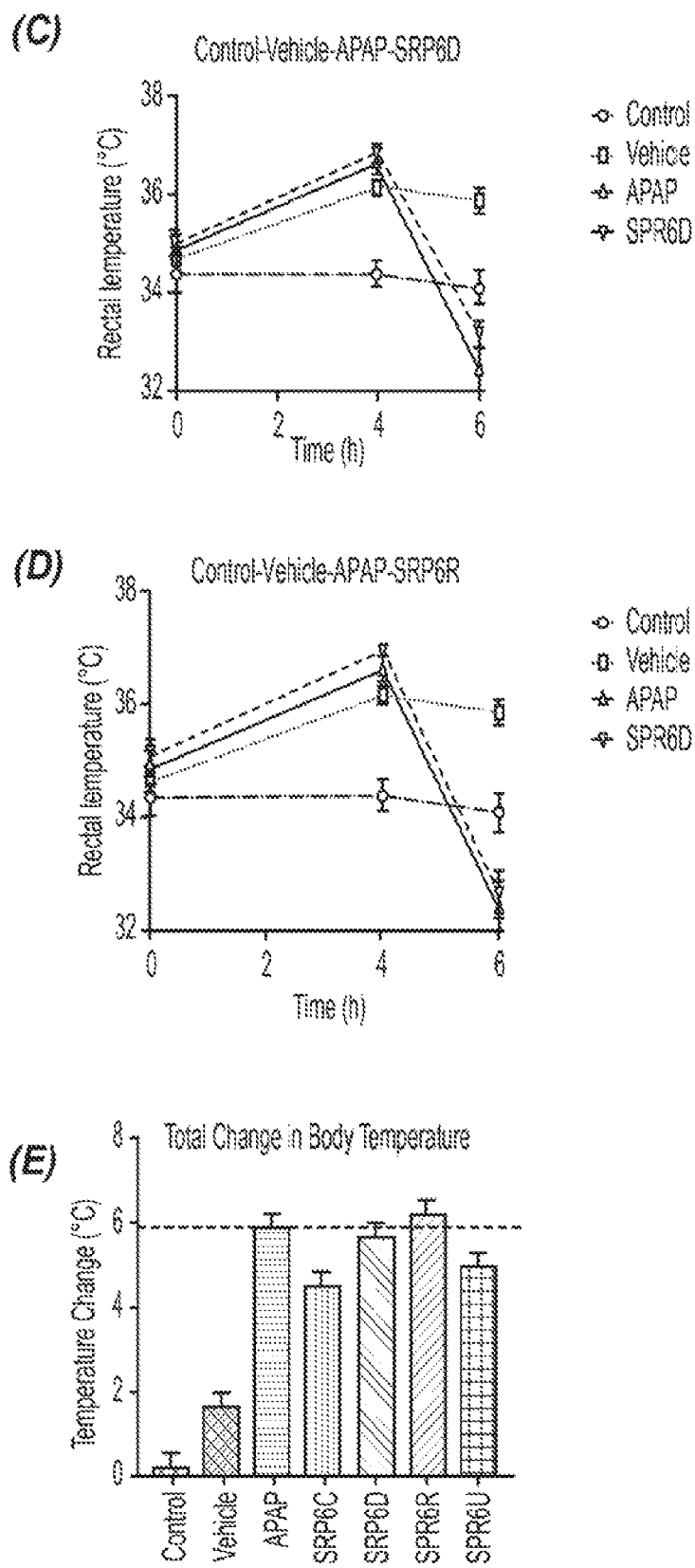
FIG. 4 - CONT.

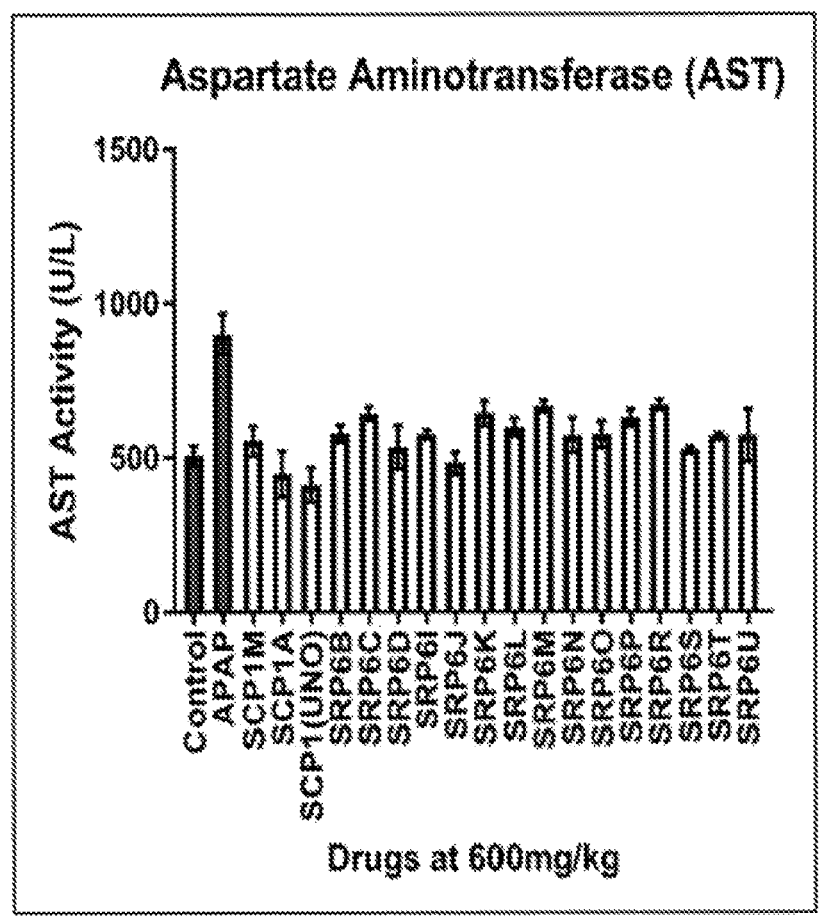
FIG. 7 - CONT.

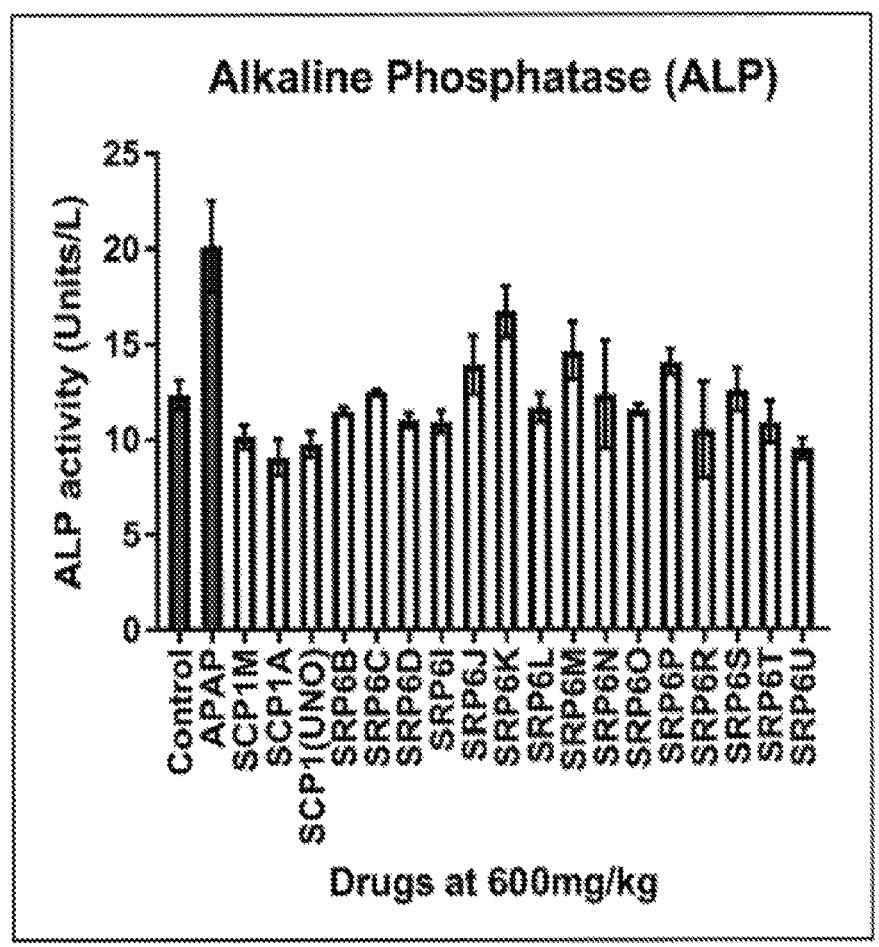
*FIG. 7 - CONT.*

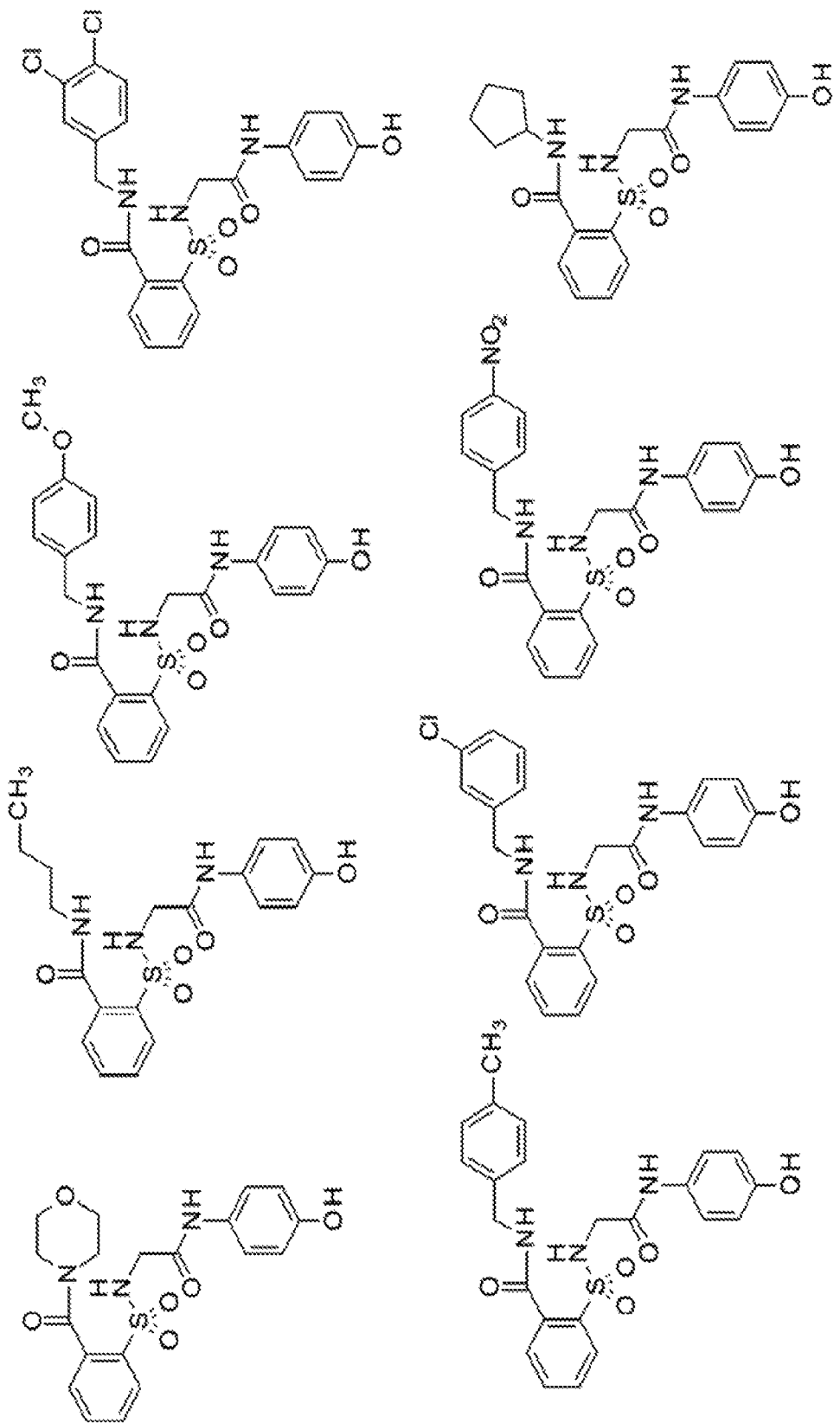

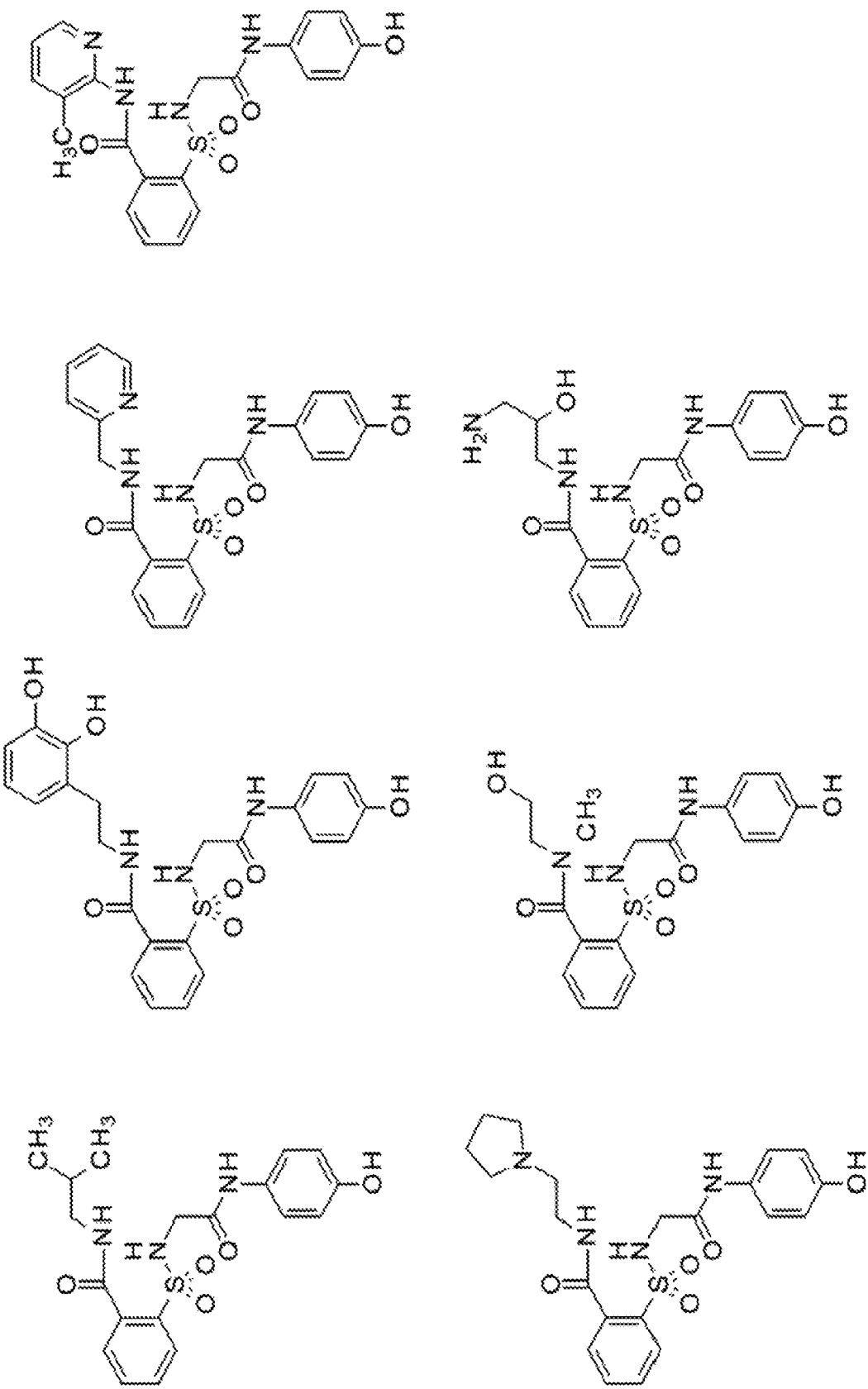
FIG. 8 - CONT.

COMPOSITIONS AND METHODS FOR AMELIORATING PAIN

This application is a national stage application under 35 U.S.C. 371 from PCT Application No. PCT/US18/22029, filed Mar. 12, 2018, which claims priority from U.S. Provisional Application No. 62/550,137 filed on Aug. 25, 2017, the entire contents of each of which are incorporated herein by reference in their entireties.

GOVERNMENT INTERESTS

This invention was made with government support under contract P30GM103340 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions, methods and kits that can be used for the treatment or amelioration of pain.

BACKGROUND OF THE INVENTION

For many types of pain (e.g., common headache, osteoarthritis) acetaminophen (ApAP, N-acetyl-para-aminophenol) has equal potency and efficacy to acetylsalicylic acid (aspirin). However, the safety of ApAP is a risk, particularly to a patient with impaired liver function. Overdose (inadvertent or for deliberate self-harm) or use in patients with compromised liver function is the most common cause of fulminant hepatic failure in Western world (Bernal, William, et al. "Acute liver failure." *The Lancet* 376.9736 (2010): 190-201). In these patients, acute fulminant hepatic failure presents are rapid development of hepatic dysfunction, leasing to encephalopathy, coagulopathy, and progressive multi-organ failure.

ApAP overdose is the leading cause for calls to Poison Control Centers across the United States with more than 100,000 annual calls and is the primary reason for more than 56,000 emergency room visits and 2,600 hospitalizations annually, resulting in an estimated 458 deaths due to acute liver failure in 2014 (Mercola, *FDA Finally Changes Prescription Recommendations for High-Dose ApAP*, 2014).

ApAP's toxicity is thought to be mediated via a toxic metabolite, N-acetyl-benzoquinoneimine (NAPQI), which depletes hepatic and renal glutathione, a cytoprotective endogenous metabolite (Mason, R. P., and V. Fischer. *Federation proceedings*. Vol. 45. No. 10. 1986; Mitchell et al., 1983). Hepatic toxicity with ApAP can occur at doses only 4- to 8-fold higher than the maximum recommended analgesic dose (Neuberger et al., 1980); renal toxicity is rarely seen clinically. Pharmaceutical combinations that contain ApAP and a centrally acting analgesic may be even more dangerous than ApAP alone. With repeated use these combinations require higher doses to produce the same analgesic effect because of an increase in tolerance. As the dose of the combination is increased to compensate for analgesic tolerance, the safety of the drug decreases as the higher doses of the ApAP component increase hepatic toxicity.

SUMMARY OF THE INVENTION

The present invention provides for analgesic compounds for treating pain.

In some embodiments, the analgesic compound comprises a compound of formula (I):

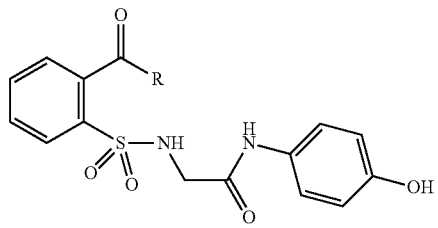

wherein R comprises $NH_2$, $N(CH_3)_2$, $NHCH_3$, $N(CH_2CH_3)_2$, $N_2(CH_2)_4CH_2C_6H_5$, $NH(CH_2)_2C_6H_5$, $NHCH_2C_6H_5$, $NO(CH_2)_4$, $NHCH_2CH_2CH_2CH_3$, $NHCH_2C_6H_4CH_3$, $NHCH_2C_6H_3Cl_2$, $NHCH_2C_6H_5CH_3$, $NHCH_2C_6H_5Cl$, $NHCH_2C_6H_5NO_2$, $NHC_5H_4$, $NHCH_2C(CH_3)_2$, $NHC(CH_3)_2$, $NHCH_2CH_2C_6H_3(OH)_2$, $NHCH_2C_6H_4N$, $NHCH_2C_6H_3NCH_3$, $NHCH_2CH_2C_4H_4N$, $N(CH_3)CH_2CH_2OH$, $NHCH_2CH(OH)CH_2NH_2$; or a pharmaceutically acceptable salt thereof.

In some embodiments, the analgesic compound comprise a compound of formula (II):

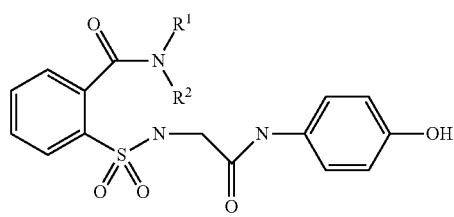

wherein $R^1$ is H, OH, an alkyl group, a haloalkyl group, a halobenzyl group, a phenyl group, —O-(alkyl), —O-(haloalkyl), —O-(halobenzyl), —O-(phenyl), an alkyl phenyl, a haloalkyl-phenyl, an alkyl-halobenzene, an alkyl-nitrobenzene, —O-(alkyl phenyl), —O-(haloalkyl)-phenyl, a cycloalkane group, and wherein $R^2$ is selected from the group consisting of H and an alkyl group; or a pharmaceutically acceptable salt thereof. In some embodiments, $R^1$ comprises H, $CH_3$, $(CH_2)_2C_6H_5$, $CH_2C_6H_5$, $CH_2CH_2CH_2CH_3$, $CH_2C_6H_3Cl_2$, $CH_2C_6H_5CH_3$, $CH_2C_6H_5Cl$, $CH_2C_6H_5NO_2$, $C_5H_4$, $CH_2C(CH_3)_2$, $C(CH_3)_2$, $CH_2CH_2C_6H_3(OH)_2$, $CH_2C_6H_4N$, $CH_2C_6H_3NCH_3$, $CH_2CH_2C_4H_4N$, $CH_2CH_2OH$, or $CH_2CH(OH)CH_2NH_2$; and wherein $R^2$ is selected from the group consisting of H and $CH_3$; or a pharmaceutically acceptable salt thereof.

In some embodiments, alkyl can comprise $C_NH_{2N-1}$, for example, wherein N is 1-10.

In some embodiments, the analgesic compound comprises the following chemical structure:

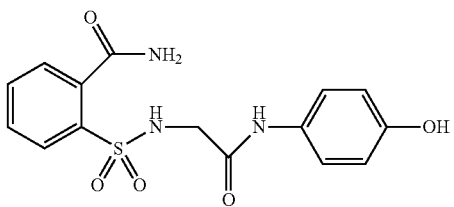 [SMILES: NC(=O)c1ccccc1S(=O)(=O)NCC(=O)Nc1ccc(O)cc1]

In some embodiments, the analgesic compound comprises the following chemical structure:

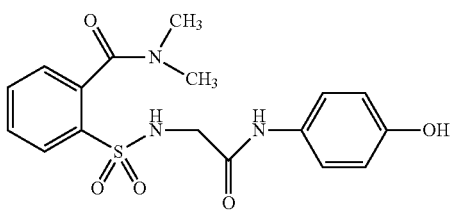 [SMILES: CN(C)C(=O)c1ccccc1S(=O)(=O)NCC(=O)Nc1ccc(O)cc1]

In some embodiments, the analgesic compound comprises the following chemical structure:

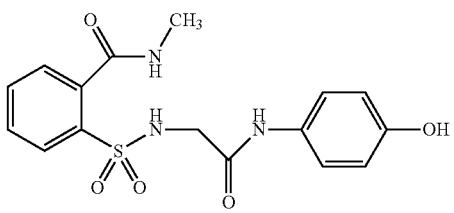 [SMILES: CNC(=O)c1ccccc1S(=O)(=O)NCC(=O)Nc1ccc(O)cc1]

In some embodiments, the analgesic compound comprises the following chemical structure:

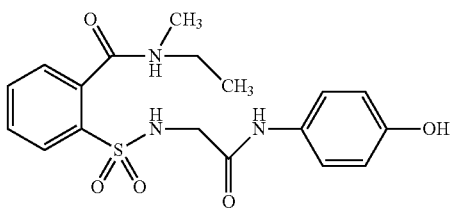 [SMILES: CCN(C)C(=O)c1ccccc1S(=O)(=O)NCC(=O)Nc1ccc(O)cc1]

In some embodiments, the analgesic compound comprises the following chemical structure:

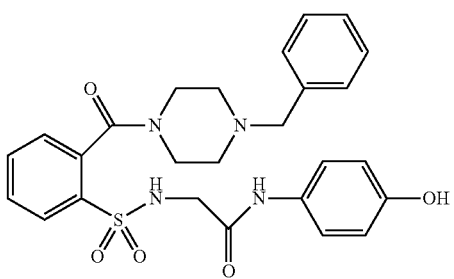 [SMILES: O=C(CNS(=O)(=O)c1ccccc1C(=O)N1CCN(Cc2ccccc2)CC1)Nc1ccc(O)cc1]

In some embodiments, the analgesic compound comprises the following chemical structure:

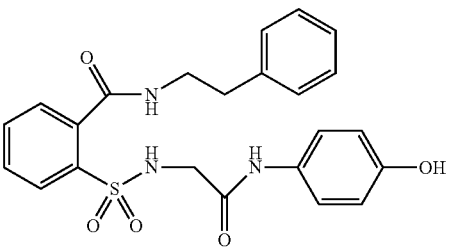 [SMILES: O=C(CNS(=O)(=O)c1ccccc1C(=O)NCCc1ccccc1)Nc1ccc(O)cc1]

In some embodiments, the analgesic compound comprises the following chemical structure:

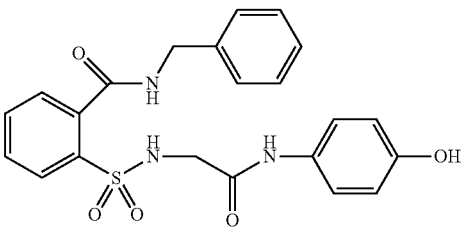 [SMILES: O=C(CNS(=O)(=O)c1ccccc1C(=O)NCc1ccccc1)Nc1ccc(O)cc1]

In some embodiments, the analgesic compound comprises the following chemical structure:

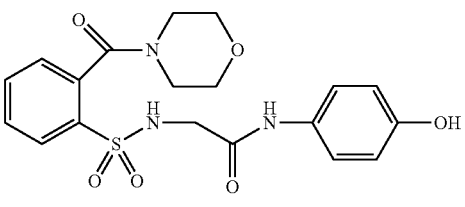 [SMILES: O=C(CNS(=O)(=O)c1ccccc1C(=O)N1CCOCC1)Nc1ccc(O)cc1]

In some embodiments, the analgesic compound comprises the following chemical structure:

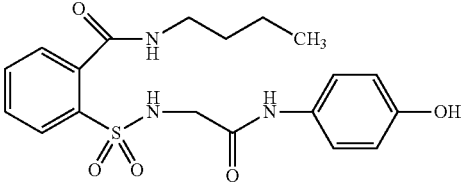 [SMILES: CCCCNC(=O)c1ccccc1S(=O)(=O)NCC(=O)Nc1ccc(O)cc1]

In some embodiments, the analgesic compound comprises the following chemical structure:

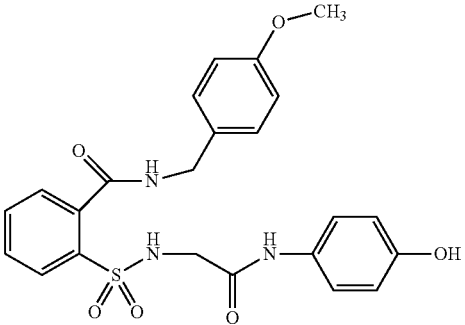 [SMILES: COc1ccc(CNC(=O)c2ccccc2S(=O)(=O)NCC(=O)Nc2ccc(O)cc2)cc1]

In some embodiments, the analgesic compound comprises the following chemical structure:

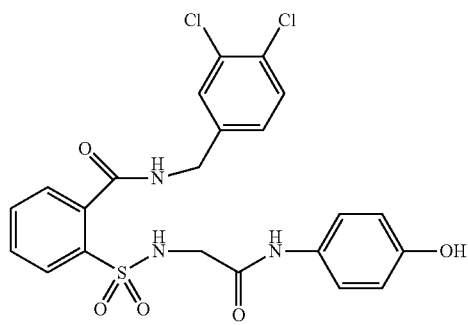 [SMILES: O=C(CNS(=O)(=O)c1ccccc1C(=O)NCc1ccc(Cl)c(Cl)c1)Nc1ccc(O)cc1]

In some embodiments, the analgesic compound comprises the following chemical structure:

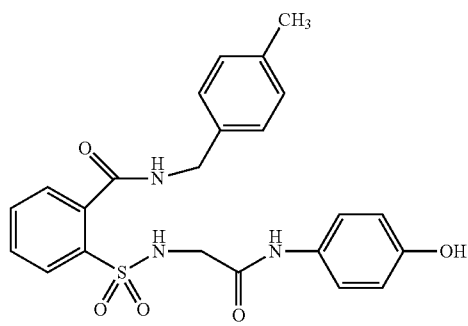 [SMILES: Cc1ccc(CNC(=O)c2ccccc2S(=O)(=O)NCC(=O)Nc2ccc(O)cc2)cc1]

In some embodiments, the analgesic compound comprises the following chemical structure:

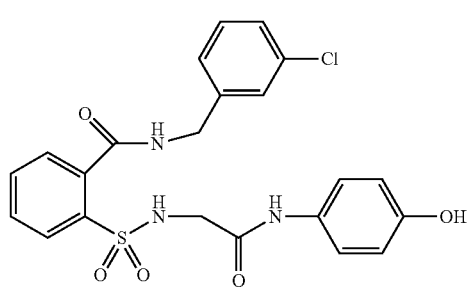 [SMILES: O=C(CNS(=O)(=O)c1ccccc1C(=O)NCc1cccc(Cl)c1)Nc1ccc(O)cc1]

In some embodiments, the analgesic compound comprises the following chemical structure:

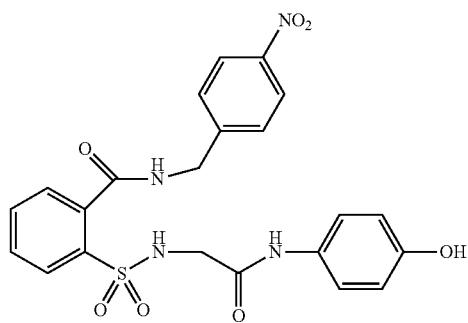 [SMILES: O=C(CNS(=O)(=O)c1ccccc1C(=O)NCc1ccc([N+](=O)[O-])cc1)Nc1ccc(O)cc1]

In some embodiments, the analgesic compound comprises the following chemical structure:

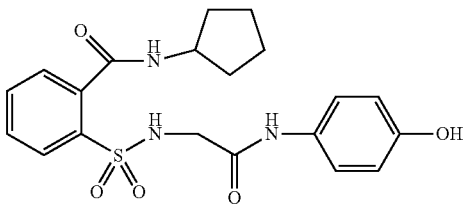 [SMILES: O=C(CNS(=O)(=O)c1ccccc1C(=O)NC1CCCC1)Nc1ccc(O)cc1]

In some embodiments, the analgesic compound comprises the following chemical structure:

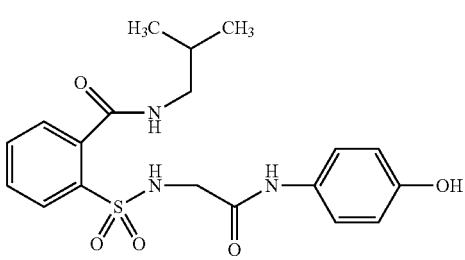 [SMILES: CC(C)CNC(=O)c1ccccc1S(=O)(=O)NCC(=O)Nc1ccc(O)cc1]

In some embodiments, the analgesic compound comprises the following chemical structure:

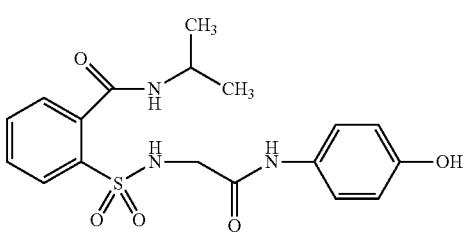 [SMILES: CC(C)NC(=O)c1ccccc1S(=O)(=O)NCC(=O)Nc1ccc(O)cc1]

In some embodiments, the analgesic compound comprises the following chemical structure:

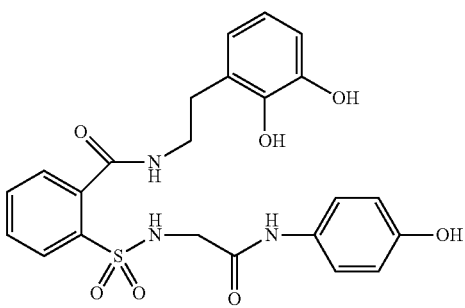 [SMILES: O=C(CNS(=O)(=O)c1ccccc1C(=O)NCCc1cccc(O)c1O)Nc1ccc(O)cc1]

In some embodiments, the analgesic compound comprises the following chemical structure:

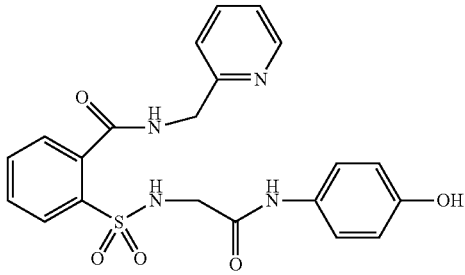 [SMILES: O=C(CNS(=O)(=O)c1ccccc1C(=O)NCc1ccccn1)Nc1ccc(O)cc1]

In some embodiments, the analgesic compound comprises the following chemical structure:

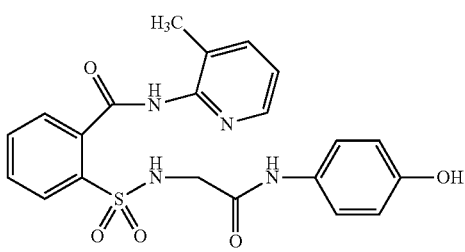 [SMILES: Cc1cccnc1NC(=O)c1ccccc1S(=O)(=O)NCC(=O)Nc1ccc(O)cc1]

In some embodiments, the analgesic compound comprises the following chemical structure:

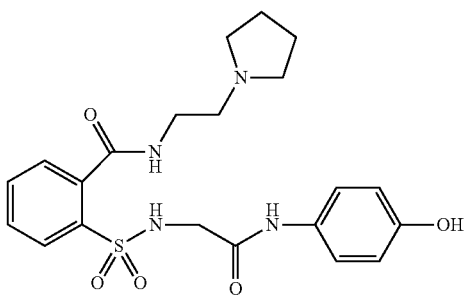 [SMILES: O=C(CNS(=O)(=O)c1ccccc1C(=O)NCCN1CCCC1)Nc1ccc(O)cc1]

In some embodiments, the analgesic compound comprises the following chemical structure:

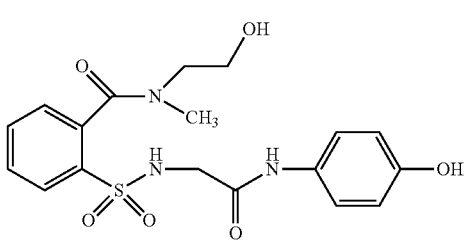 [SMILES: CN(CCO)C(=O)c1ccccc1S(=O)(=O)NCC(=O)Nc1ccc(O)cc1]

In some embodiments, the analgesic compound comprises the following chemical structure:

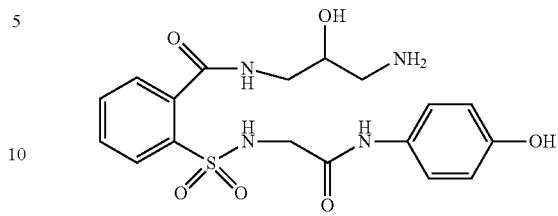

In some embodiments, the analgesic compound has a reduced risk of hepatotoxicity when administered to a subject in vivo. For example, the composition can reduce the risk of hepatotoxicity by at least 5%, 10%, 15%, 20%, 25%, 30%, 35%, 40%, 45%, or 50%.

In some embodiments, the analgesic compound exhibits analgesia comparable to ApAP when administered to a subject in vivo.

In some embodiments, the analgesic compound is a non-narcotic analgesic.

In some embodiments, the analgesic compound exhibits antipyretic activity.

In some embodiments, the composition is not metabolized to NAPQI.

In some embodiments, the analgesic compound has a reduced risk of hepatotoxicity, exhibits analgesia comparable to ApAP, is non-narcotic, exhibits antipyresis, and is not metabolized to NAPQI when administered to a subject in vivo.

The present invention is further directed towards pharmaceutical compositions comprising an analgesic compound as described herein and a second active ingredient, such as an opioid or an non-steroidal anti-inflammatory drug (NSAID). Non-limiting examples such opioids comprise codeine, fentanyl, hydrocodone, hydrocodone/ApAP, hydromorphone, meperidine, methadone, morphine, oxycodone, oxycodone and ApAP, oxycodone and naloxone. Non-limiting examples of NSAIDs comprise aspirin, celecoxib, diclofenac, diflunisal, etodolac, ibuprofen, indomethacin, ketoprofen, ketorolac, nabumetone, naproxen, oxaprozin, piroxicam, salsalate, sulindac, and tolmetin.

The present invention also provides for a method of treating pain in a subject.

The present invention further provides for a method of alleviating pain in a subject.

Still further, the present invention provides for a method of preventing pain in a subject, reducing the incidence of pain in a subject, delaying the development of pain in a subject, preventing the development of pain in a subject, and/or palliating pain in a subject.

Non-limiting examples of such pain comprise acute pain, chronic pain, neuropathic pain, nociceptive pain, post-surgical pain, eye pain, dental pain, and/or veterinary pain. In some embodiments, neuropathic pain comprises post-surgical pain, neuropathic pain, dental pain, ophthalmic pain, arthritic pain, post- and/or traumatic pain, or a combination thereof.

In some embodiments, the method comprises administering to a subject in need thereof a therapeutically effective amount of the analgesic compound or composition as described herein. For example, the therapeutically effective amount of the analgesic compound or composition administered to a subject can comprise a dose of about 10 µM to about 10 mM, or a dose of about 50 µM to about 1 mM.

In some embodiments, the analgesic compound or composition is administered to a subject in a single dose, such as in a bolus. In other embodiments, the compound is administered at intervals of about 4 hours, 12 hours, or 24 hours. In still other embodiments, the compound is administered continuously, such as in a drip IV infusion.

In some embodiments, the composition can be administered orally, such as in a pill, tablet, aqueous solution, or capsule; parentally, such as in an intravenous or intramuscular injection; transdermally, such as in a cream, lotion, or patch; or nasally, such as in a spray. In other embodiments, the composition can be administered subcutaneously, intrapulmonary, topically, intravitreally, transmucosally, rectally, and intranasally administration.

In some embodiments, the composition or analgesic compound as described herein can be administered to a subject together with a therapeutically effective amount of a second active ingredient, such as an opioid and/or NSAID. The second active ingredient can be administered prior to, concurrently with, or subsequent to the administration of a composition or analgesic compound as described herein.

The present invention further provides a medical kit for the treatment of pain. In embodiments, the kit comprises printed instructions for administering the compound to the subject afflicted with pain and an analgesic compound or composition as described herein.

Other objects and advantages of this invention will become readily apparent from the ensuing description.

DETAILED DESCRIPTION OF THE INVENTION

Abbreviations and Definitions

Figure 1:
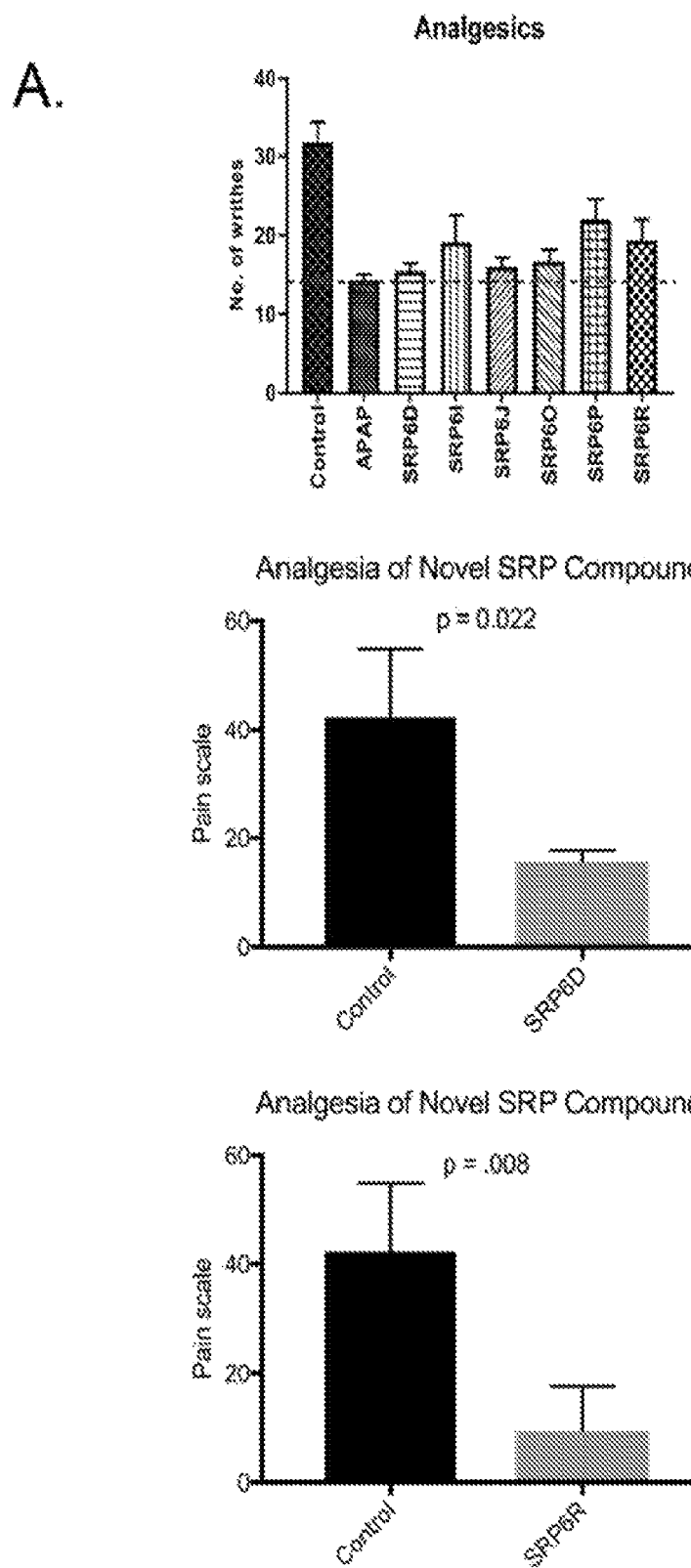
FIG. 1 shows analgesia of novel compounds SRP6D, R is comparable to ApAP in an in vivo mouse model utilizing two pain assays. A) Acetic acid-induced abdominal writhing assay. Number of abdominal stretches (writhes) induced by injection of acetic acid, n=7, p<0.05. SRP6D (n=5, p=0.022) and C) SRP6R (n=5, p=0.008) display analgesia compared to control/vehicle only. B) Tail flick assay. Percentage of maximum analgesia for each mouse were calculated with the formula, Percentage Analgesia=100*{[(Latency to tail flick after drug injection)−(Latency to tail flick at baseline)]/[(12 sec cutoff time)−(Baseline latency)]}. Data expressed as mean±SEM, n=10.

Detailed descriptions of one or more embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Analgesic Compounds

Aspects of the invention are directed towards analgesic compounds and compositions comprising the analgesic compounds. The term "analgesic" or "analgesia" can refer to an agent that lessens, alleviates, reduces, relieves, or extinguishes pain in an area of a subject's body.

Further, aspects of the invention are directed towards compounds and/or compositions that exhibit antipyrisis. For example, analgesic compounds as described herein can be considered "antipyretics" or "antipyretic compounds," which can refer to a compound or composition that has the ability to reduce the subject's body temperature, such as to physiologically normal levels, when the subject has an abnormally high body temperature (e.g., fever). Antipyretic compounds, such as those described herein, can also block the onset of fever.

Embodiments of the invention demonstrate analgesic and/or antipyretic properties while having no or reduced levels of hepatotoxicity. The term "hepatotoxicity" can refer to the chemical- or drug-induced liver damage. Drug-induced liver injury or damage is a cause of acute or chronic liver disease. Hepatotoxicity can be caused by certain medicinal agents, when taken in overdoses or sometimes even when introduced within therapeutic ranges.

ApAP is usually well tolerated in prescribed dose, but overdose is a common cause of drug-induced liver disease and acute liver failure. Damage to the liver is not due to the drug itself but to a toxic metabolite (N-acetyl-p-benzoquinone imine (NAPQI)) produced by cytochrome P-450 enzymes in the liver. In normal circumstances, this metabolite is detoxified by conjugating with glutathione in phase 2 reaction. In an overdose, a large amount of NAPQI is generated, which overwhelms the detoxification process and leads to liver cell damage. Nitric oxide also plays a role in inducing toxicity. The risk of liver injury is influenced by several factors, such as the dose ingested, concurrent alcohol or other drug intake, and/or interval between ingestion and antidote. The dose toxic to the liver is quite variable from person to person and is often thought to be lower in chronic alcoholics. Measurement of blood level is important in assessing prognosis, wherein higher levels predicting a worse prognosis. Those that develop acute liver failure can still recover spontaneously, but may require transplantation if poor prognostic signs such as encephalopathy or coagulopathy is present.

In some embodiments, the analgesic compound or composition comprising the same has a reduced risk of hepatotoxicity, for example when compared to ApAP, when administered to a subject in vivo. For example, the composition can reduce the risk of hepatotoxicity by at least 5%, 10%, 15%, 20%, 25%, 30%, 35%, 40%, 45%, or 50%.

In some embodiments, the analgesic compound comprises formula (I):

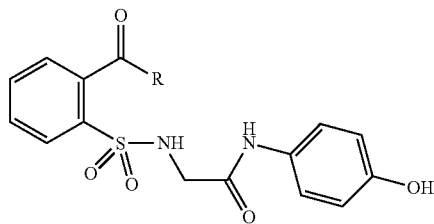

In other embodiments, R comprises $NH_2$, $N(CH_3)_2$, $NHCH_3$, $N(CH_2CH_3)_2$, $N_2(CH_2)_4CH_2C_6H_5$, $NH(CH_2)_2C_6H_5$, $NHCH_2C_6H_5$, $NO(CH_2)_4$, $NHCH_2CH_2CH_3$, $NHCH_2C_6H_4CH_3$, $NHCH_2C_6H_3Cl_2$, $NHCH_2C_6H_5CH_3$, $NHCH_2C_6H_5Cl$, $NHCH_2C_6H_5NO_2$, $NHC_5H_4$, $NHCH_2C(CH_3)_2$, $NHC(CH_3)_2$, $NHCH_2CH_2C_6H_3(OH)_2$, $NHCH_2C_6H_4N$, $NHCH_2C_6H_3NCH_3$, $NHCH_2CH_2C_4H_4N$, $N(CH_3)CH_2CH_2OH$, $NHCH_2CH(OH)CH_2NH_2$; or a pharmaceutically acceptable salt thereof.

In some embodiments, the analgesic compound comprises formula (II):

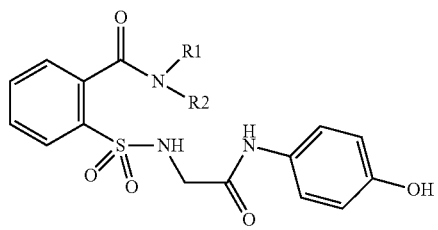

In some embodiments, $R^1$ can be H, OH, an alkyl group, a halogen group, a haloalkyl group, a halobenzyl group, a phenyl group, —O-(alkyl), —O-(haloalkyl), —O-(phenyl), —O-(halobenzyl), an alkyl phenyl, a haloalkyl-phenyl, an alkyl-halobenzene, an alkyl-nitrobenzene, —O-(alkyl phenyl), —O-(haloalkyl)-phenyl, a cycloalkane group. In further embodiments, the alkyl group comprises C1-C2 carbon chains, C1-C3 carbon chains, C1-C4 carbon chains, C1-C5 carbon chains, C1-C6 carbon chains, C1-C7 carbon chains, C1-C8 carbon chains, C1-C9 carbon chains, C1-C10 carbon chains. In other embodiments, the alkyl group can be C1-C4 carbon chains. In some embodiments, the halogen can be F, Br, Cl. In some embodiments, the cycloalkane group can be a 5-member ring. In some embodiments, the cycloalkane group can be a 6-member ring. In some embodiments, the analgesic compound described herein is pharmaceutically acceptable salt.

In yet other embodiments, $R^2$ can be H, OH, an alkyl group, a halogen group, a haloalkyl group, a halobenzyl group, a phenyl group, —O-(alkyl), —O-(haloalkyl), —O-(phenyl), —O-(halobenzyl), an alkyl phenyl, a haloalkyl-phenyl, an alkyl-halobenzene, an alkyl-nitrobenzene, —O-(alkyl phenyl), —O-(haloalkyl)-phenyl, a cycloalkane group. In further embodiments, the alkyl group comprises C1-C2 carbon chains, C1-C3 carbon chains, C1-C4 carbon chains, C1-C5 carbon chains, C1-C6 carbon chains, C1-C7 carbon chains, C1-C8 carbon chains, C1-C9 carbon chains, C1-C10 carbon chains. In other embodiments, the alkyl group can be C1-C4 carbon chains. In some embodiments, the halogen can be F, Br, Cl. In some embodiments, the cycloalkane group can be a 5-member ring. In some embodiments, the cycloalkane group can be a 6-member ring. In some embodiments, the analgesic compound described herein is pharmaceutically acceptable salt.

In further embodiments, $R^1$ comprises H, $CH_3$, $(CH_2)_2C_6H_5$, $CH_2C_6H_5$, $CH_2CH_2CH_2CH_3$, $CH_2C_6H_3Cl_2$, $CH_2C_6H_5CH_3$, $CH_2C_6H_5Cl$, $CH_2C_6H_5NO_2$, $C_5H_4$, $CH_2C(CH_3)_2$, $C(CH_3)_2$, $CH_2CH_2C_6H_3(OH)_2$, $CH_2C_6H_4N$, $CH_2C_6H_3NCH_3$, $CH_2CH_2C_4H_4N$, $CH_2CH_2OH$, or $CH_2CH(OH)CH_2NH_2$; and $R^2$ is selected from the group consisting of H and $CH_3$, or a pharmaceutically acceptable salt thereof.

Non-limiting examples of analgesic compounds of the inventions are shown in Table 1 below. As desired, such compounds can also be provided as salts thereof.

TABLE 1

| Identifier | STRUCTURE | Mol weight | cLog P |
|---|---|---|---|
| SRP6a | 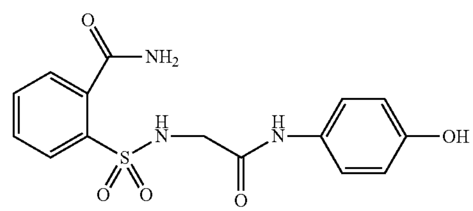 [SMILES: NC(=O)c1ccccc1S(=O)(=O)NCC(=O)Nc1ccc(O)cc1] | 349.36 | 0.26 |
| SRP6b | 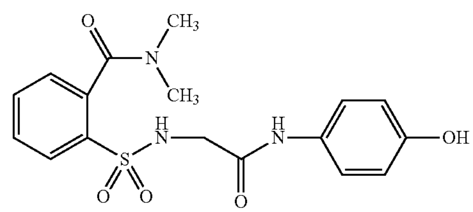 [SMILES: CN(C)C(=O)c1ccccc1S(=O)(=O)NCC(=O)Nc1ccc(O)cc1] | 377.41 | 0.71 |
| SRP6c | 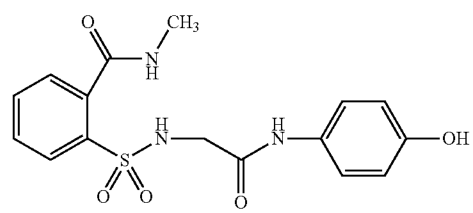 [SMILES: CNC(=O)c1ccccc1S(=O)(=O)NCC(=O)Nc1ccc(O)cc1] | 363.39 | 0.49 |
| SRP6d | 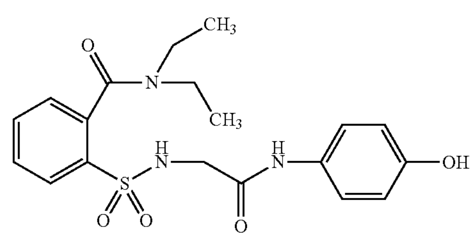 [SMILES: CCN(CC)C(=O)c1ccccc1S(=O)(=O)NCC(=O)Nc1ccc(O)cc1] | 405.47 | 1.42 |
| SRP6e | 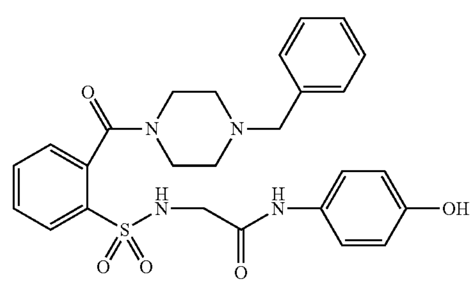 [SMILES: O=C(CNS(=O)(=O)c1ccccc1C(=O)N1CCN(Cc2ccccc2)CC1)Nc1ccc(O)cc1] | 508.59 | 2.28 |

TABLE 1-continued
| Identifier | STRUCTURE | Mol weight | cLog P |
|---|---|---|---|
| SRP6f | 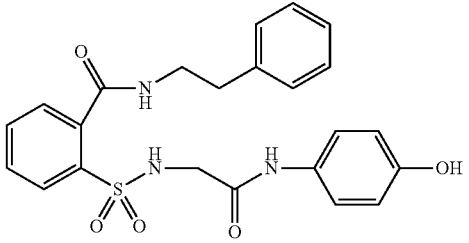 [SMILES: O=C(CNS(=O)(=O)c1ccccc1C(=O)NCCc1ccccc1)Nc1ccc(O)cc1] | 453.51 | 2.50 |
| SRP6g | 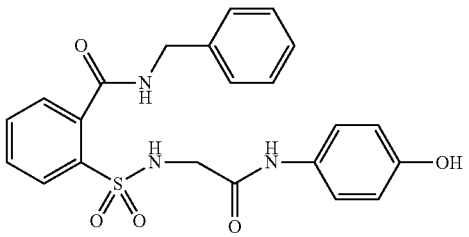 [SMILES: O=C(CNS(=O)(=O)c1ccccc1C(=O)NCc1ccccc1)Nc1ccc(O)cc1] | 439.48 | 2.21 |
| SRP6h | 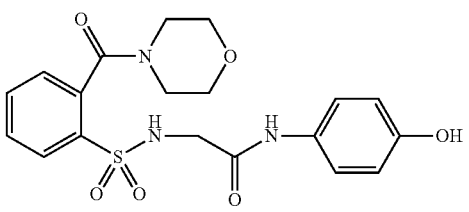 [SMILES: O=C(CNS(=O)(=O)c1ccccc1C(=O)N1CCOCC1)Nc1ccc(O)cc1] | 419.45 | 0.49 |
| SRP6i | 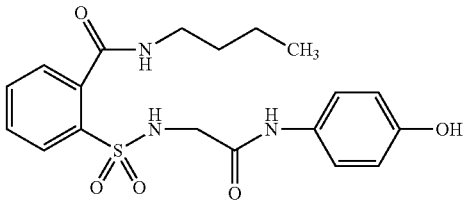 [SMILES: CCCCNC(=O)c1ccccc1S(=O)(=O)NCC(=O)Nc1ccc(O)cc1] | 405.47 | 1.81 |
| SRP6j | 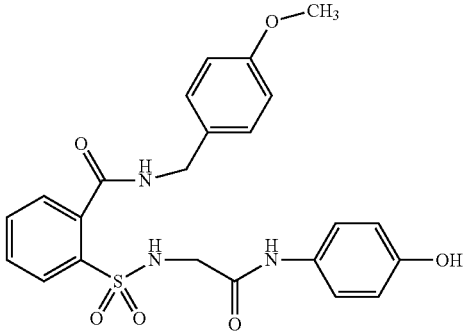 [SMILES: COc1ccc(CNC(=O)c2ccccc2S(=O)(=O)NCC(=O)Nc2ccc(O)cc2)cc1] | 469.51 | 2.05 |

TABLE 1-continued

| Identifier | STRUCTURE | Mol weight | cLog P |
|---|---|---|---|
| SRP6k | 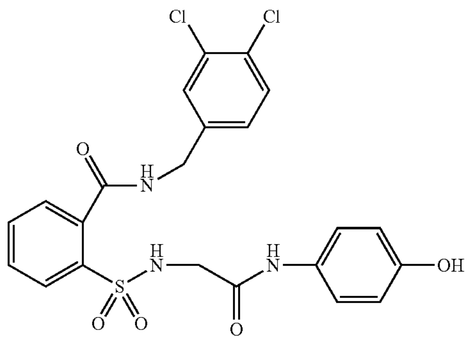 [SMILES: O=C(CNS(=O)(=O)c1ccccc1C(=O)NCc1ccc(Cl)c(Cl)c1)Nc1ccc(O)cc1] | 508.37 | 3.42 |
| SRP6l | 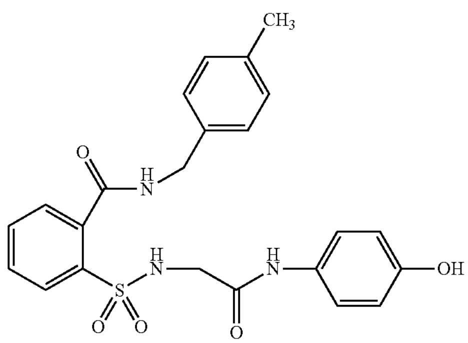 [SMILES: Cc1ccc(CNC(=O)c2ccccc2S(=O)(=O)NCC(=O)Nc2ccc(O)cc2)cc1] | 453.51 | 2.72 |
| SRP6m | 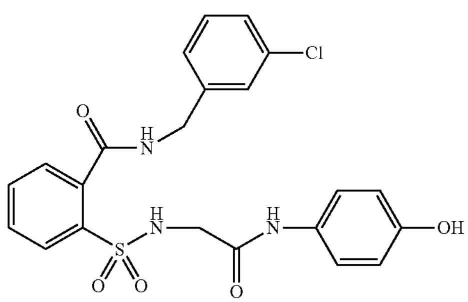 [SMILES: O=C(CNS(=O)(=O)c1ccccc1C(=O)NCc1cccc(Cl)c1)Nc1ccc(O)cc1] | 473.93 | 2.81 |
| SRP6n | 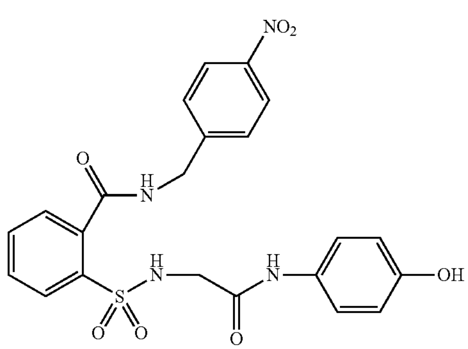 [SMILES: O=C(CNS(=O)(=O)c1ccccc1C(=O)NCc1ccc([N+](=O)[O-])cc1)Nc1ccc(O)cc1] | 484.48 | 2.75 |

TABLE 1-continued
| Identifier | STRUCTURE | Mol weight | cLog P |
|---|---|---|---|
| SRP6o | 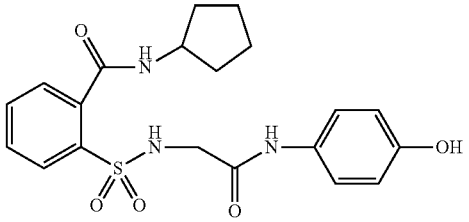 [SMILES: O=C(CNS(=O)(=O)c1ccccc1C(=O)NC1CCCC1)Nc1ccc(O)cc1] | 417.48 | 1.84 |
| SRP6p | 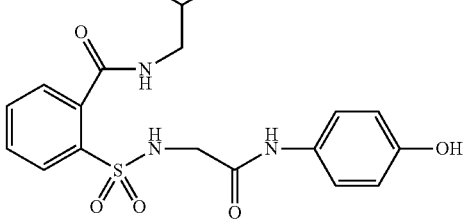 | 405.47 | 1.73 |
| SRP6q | 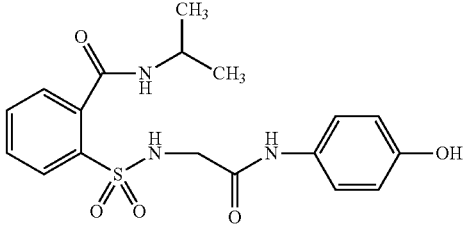 [SMILES: CC(C)NC(=O)c1ccccc1S(=O)(=O)NCC(=O)Nc1ccc(O)cc1] | 391.44 | 1.26 |
| SRP6r | 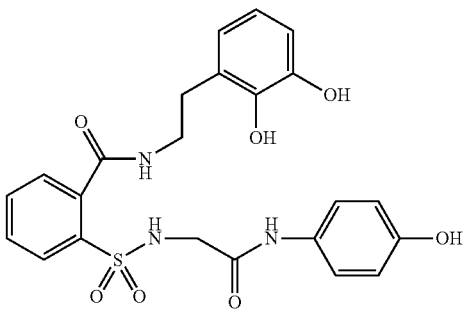 [SMILES: O=C(CNS(=O)(=O)c1ccccc1C(=O)NCCc1cccc(O)c1O)Nc1ccc(O)cc1] | 485.51 | 1.89 |
| SRP6s | 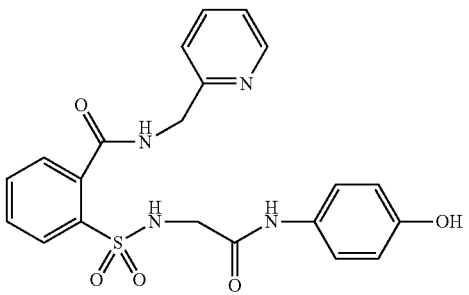 [SMILES: O=C(CNS(=O)(=O)c1ccccc1C(=O)NCc1ccccn1)Nc1ccc(O)cc1] | 440.47 | 1.07 |

TABLE 1-continued

| Identifier | STRUCTURE | Mol weight | cLog P |
|---|---|---|---|
| SRP6t | 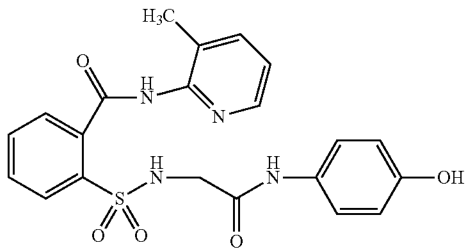 [SMILES: Cc1cccnc1NC(=O)c1ccccc1S(=O)(=O)NCC(=O)Nc1ccc(O)cc1] | 440.47 | 2.39 |
| SRP6u | 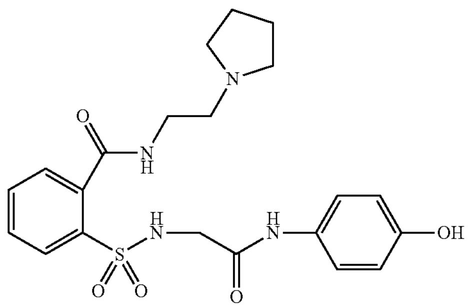 [SMILES: O=C(CNS(=O)(=O)c1ccccc1C(=O)NCCN1CCCC1)Nc1ccc(O)cc1] | 446.52 | 0.60 |
| SRP6w | 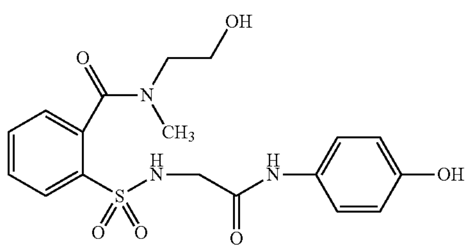 [SMILES: CN(CCO)C(=O)c1ccccc1S(=O)(=O)NCC(=O)Nc1ccc(O)cc1] | | |
| SRP6x | 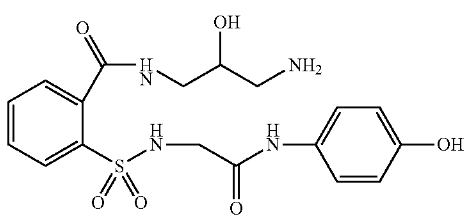 [SMILES: NCC(O)CNC(=O)c1ccccc1S(=O)(=O)NCC(=O)Nc1ccc(O)cc1] | | |
| SCP1 | | 332.33 | 1.28 |
| SCP1M (SCP-1 metabolite) | | 350.35 | From 1.07 to −2.48 |

Figure 10:
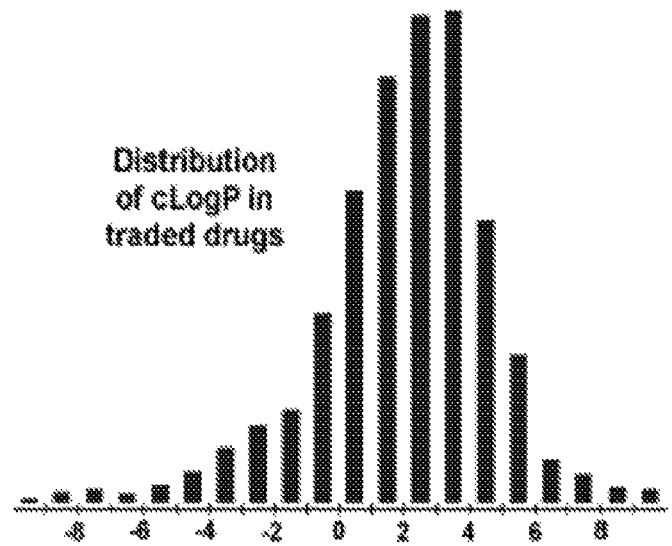
FIG. 10 is a bar graph showing the distribution of calculated log P values of more than 3000 drugs on the market.

The log P value of a compound is a measure of the compound's hydrophilicity. The log P value of a compound, which is the logarithm of its partition coefficient between n-octanol and water $\log(c_{octanol}/c_{water})$, is a measure of the compound's hydrophilicity. Typically, a low solubility contributes to poor absorption. Low hydrophilicities are indicated by high log P. High log P values can indicate poor absorption or permeation. Low Calculated Log P (c Log P) values can indicate compounds with shorter half-lives and poor absorption. Low hydrophilicities and therefore high log P values cause poor absorption or permeation. Without being bound by theory, for compounds to have a reasonable probability of being well absorbed, their log P value must not be greater than 5.0. Exemplary embodiments comprise compounds with intermediate c Log P values, such as about 1, 1.2, 1.4, 1.6, 1.8, 2.0, 2.2, 2.4, 2.6, 2.8, or 3. In some embodiments, the c Log P value of a compound is about 2.0. Embodiments can also comprise a compound with a log P value of no greater than about 5.0. The distribution of calculated log P values of more than 3000 drugs on the market is shown in FIG. 10 [source: http://www.openmolecules.org/properties/properties.html.]

Pain

Embodiments can be used for the treatment or amelioration of pain, non-limiting examples of which comprise post-surgical, neuropathic, dental, ophthalmic, arthritic, post- and/or traumatic pain.

The term "pain" can refer to all types of pain. For example, the term can refer to acute pains and chronic pains, such as neuropathic pain and post-operative/post-surgical pain, chronic lower back pain, ophthalmic pain, arthritic pain, post-traumatic pain, traumatic pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post-partum pain, migraine, angina pain, and genitourinary tract-related pain including cystitis. The term can also refer to nociceptive pain or nociception, such as somatic pain (normal nerve response to a noxious stimulus). Pain can also refer to pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93-98 (Wilson et al., eds., 12th ed. 1991); Williams et al., *J. of Medicinal Chem.* 42:1481-1485 (1999), herein each incorporated by reference in their entirety).

"Neuropathic pain" (NP) can refer to a type of chronic pain that frequently develops following an injury or disease of either nerve or peripheral tissue. Neuropathic pain (NP) can develop with ongoing, spontaneous, paroxysmal, and lancinating pain components. Such NP is almost invariably associated with abnormalities of cutaneous sensibility in the forms of allodynia (sensation of pain from stimuli that are not normally painful), hyperalgesia (increased sensation to normally painful stimuli), and dysesthesis (unpleasant abnormal sensation). Although knowledge about neuropathic pain mechanisms has advanced tremendously, satisfactory treatment options for NP have been elusive.

Neuropathic pain according to the present disclosure can be divided into "peripheral" (originating in the peripheral nervous system) and "central" (originating in the brain or spinal cord).

The features of neuropathic pain are known to be different from that of the general, nociceptive type of pain. Nociceptive type of pain can refer to a chronic or acute pain associated with a painful stimulus. Most animal models used to study pain and its treatment are based on the nociceptive type of pain, e.g., tail flick or hot plate models. Neuropathic pain can be induced by innocuous stimuli, and responds much less to some medications than does the nociceptive type. For example, opioids seldom have an analgesic effect on neuropathic pain, while opioids are successful in producing an analgesic effect on nociceptive pain. Neuropathic pain can result from peripheral nerve trauma (e.g., amputation), infection (e.g., post-herpetic neuralgia), infarct, or metabolic disturbance (e.g., diabetic neuralgia). New treatment strategies are needed for treatment of neuropathic pain.

"Dental pain" can refer to pain felt in the mouth area, such as gums, teeth, and/or jaw. Dental pain can indicate an oral health problem, such as gum disease, tooth decay or TMJ disorder, although the pain can also be caused by conditions that are not dental in nature, such as sinus or ear infections or heart problems.

In most cases, dental pain can be caused be or can result from to tooth decay. When a cavity gets larger, it begins to irritate the pulp, which is the center of the tooth that contains nerves and blood vessels. The pulp can also be irritated when the tooth is touched or comes into contact with cold, hot or very sweet food and beverages. In advanced cases of tooth decay, destruction of the enamel and dentin (the middle layer of the tooth) can allow bacteria to invade the pulp, which can lead to infection and result in tooth abscess. Whenever the pulp becomes irritated, its nerves send signals to the brain, causing pain. Although the pain may sometimes dissipate over time without any treatment, the condition will continue to worsen and the pain can return if the tissue and bone surrounding the affected tooth becomes infected.

Gingivitis can also be the cause of dental pain. The soft tissue of the gums can become inflamed because of the build-up of plaque along the gum line. As a result, gums loosen and detach from the teeth, forming deep pockets of space between the gums and teeth. Bacteria invade these pockets, causing swelling, bleeding and pain. In severe cases, when bacteria dissolve the bone surrounding tooth roots, tooth and bone loss may occur. When the roots of teeth become exposed due to receding gums or bone loss, tooth sensitivity can result. Nerve endings contained in the lower part of the tooth react to certain stimuli, such as cold air, food or drinks, causing dental pain.

Dental pain can also occur in the jaw area and can be caused by, for example, muscle strain. The muscles controlling the temporomandibular joint (TMJ) can spasm and trigger pain. This often happens in patients with an unstable bite, missing or improperly aligned teeth.

The additional oral symptoms that can be related to dental pain depend on its cause, non-limiting examples of which comprise sensitivity to certain stimuli (e.g., cold, heat, air, biting, chewing), loose teeth, bad breath (halitosis), red and/or swollen gums, bleeding gums, receding gums, difficulty opening or closing the mouth, cracking sound when jaw opens, foul-tasting discharge, and/or pus near the source of the pain. Furthermore, symptoms in other areas of the body can appear along with dental pain, non-limiting examples of which comprise fever, headaches and difficulty swallowing or breathing.

Dental pain can be due to a variety of medical conditions, non-limiting examples of which comprise tooth decay, gum disease, debris, temporomandibular joint (TMJ) disorder, and/or teeth grinding (bruxism). Other causes of dental pain comprise tooth eruption, such as in children, or tooth impaction; fractured, cracked or broken teeth; exposed tooth root; dry socket (complication of tooth extraction); trauma to head or teeth; abnormal bite; recent dental work; and or meth mouth (caused by use of methamphetamine). Further, dental pain can also be the result of a condition elsewhere in the body, such as ear infection, sinus infection, migraines, heart problems (such as pain that increases with exertion), neurological conditions (e.g., trigeminal neuralgia), burning mouth syndrome, and/or salivary gland dysfunction.

"Ophthalmic pain" or "eye pain," also known as ophthalmalgia can fall into one of two categories: ocular pain which occurs on the eye's surface, and/or orbital pain which occurs within the eye.

Eye pain that occurs on the surface can be a scratching, burning, or itching sensation. Surface pain can be caused by irritation from a foreign object, infection, or trauma.

Eye pain that occurs deeper within the eye can be aching, gritty, stabbing, or throbbing.

Eye pain can be accompanied by vision loss.

Ophthalmic pain, which occurs on the eye's surface, can be caused by, for example, a foreign object, conjunctivitis, contact lens irritation, corneal abrasion, injury, chemical burns and flash burns to the eye, blepharitis, and/or a sty.

Ophthalmic pain that occurs within the eye (e.g. orbital pain) can be caused by glaucoma, optic neuritis, sinusitis, migraines, injury, iritis, and/or inflammation of the eye.

"Arthritic pain" can refer to any pain arising anatomically from the joints and their adjacent bones and non-osseous tissues. Any arthritic pain can be treated by the invention including, without limitation, any pain resulting from an auto-immune, infectious, inflammatory, proliferative, regenerative or degenerative process so involving the joints of an animal or human patient. As such, suitable pain treatable with the current invention includes pain from rheumatoid or osteo arthritis.

"Post-surgical pain" (interchangeably termed "post-incisional" or "post-traumatic pain") can refer to pain arising or resulting from an external trauma such as a cut, puncture, incision, tear, or wound into tissue of an individual (including that that arises from all surgical procedures, whether invasive or non-invasive).

In some embodiments, post-surgical pain is internal or external (including peripheral) pain, and the wound, cut, trauma, tear or incision may occur accidentally (as with a traumatic wound) or deliberately (as with a surgical incision).

Post-surgical pain, as used herein, includes allodynia (i.e., increased response (i.e., a noxious perception) to a normally non-noxious stimulus) and hyperalgesia (i.e., increased response to a normally noxious or unpleasant stimulus), which can in turn, be thermal or mechanical (tactile) in nature. In some embodiments, the post-surgical pain is characterized by thermal sensitivity, mechanical sensitivity and/or resting pain. In some embodiments, the post-surgical pain comprises mechanically-induced pain or resting pain. In other embodiments, the post-surgical pain comprises resting pain.

Pharmaceutical Combinations

Embodiments comprise structural analogs of ApAP molecules that function as non-toxic, non-addictive, non-narcotic pain relievers. Such compounds can be a component of pharmaceutical combinations for the treatment or amelioration of pain.

The pharmaceutical combinations of the present invention comprise analgesics as described herein, such as SRP6D and SRP6R, in an admixture with an analgesic as described herein along with a pharmaceutically acceptable carrier prepared according to conventional pharmaceutical techniques. According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil. The amount of the carrier employed in conjunction with the combination is sufficient to provide a practical quantity of material per unit dose of analgesic.

The use of such media and agents for pharmaceutically active substances is well known in the art. Any conventional media or agent that is compatible with the active compound can be used. Supplementary active compounds can also be incorporated into the compositions.

Pharmaceutically acceptable carriers for oral administration comprise sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration comprise isotonic saline, propylene glycol, ethyl oleate, pyrrolidone, aqueous ethanol, sesame oil, corn oil, and combinations thereof.

Various oral dosages forms can be employed, non-limiting examples of which comprise solid forms such as tablets, capsules, granules, suppositories and/or powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms comprise aqueous solutions, emulsions, suspensions, syrups, aerosols and/or reconstituted solutions and/or suspensions. The composition may alternatively be formulated for external topical application, or in the form of a sterile injectable solution.

Pharmaceutically effective combinations can be provided as a composition comprising between 0.1 and 2000 mg/kg of an analgesic as described herein, such as SRP6D and SRP6R. For example, pharmaceutically effective combinations can be provided as a composition comprising about 0.1 mg/kg, 1 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg of an analgesic. Useful pharmaceutically effective combinations can contain between about 300 mg/kg and about 1000 mg/kg of an analgesic as described herein, such as SRP6D and SRP6R. For example, embodiments as described herein can comprise about 300 mg/kg of an analgesic.

Pharmaceutically effective combinations, such as a pill or tablet, can be comprise between 0.1 and 2000 mg of an analgesic as described herein, such as SRP6D and SRP6R. For example, pharmaceutically effective combinations can comprise about 0.1 mg, 1 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg of an analgesic. Useful pharmaceutically effective combinations can contain between about 300 mg and about 1000 mg of an analgesic as described herein, such as SRP6D and SRP6R. For example, embodiments as described herein can comprise about 300 mg of an analgesic.

The present invention also comprises the formation of pharmaceutically acceptable, stable salts of the compounds as described herein, such as SRP6D and SRP6R, with metals or amines. Non-limiting examples of metals used as cations comprise alkali metals such as $Na^+$ or $K^+$ and alkaline-earth metals such as $Mg^{2+}$ and $Ca^{2+}$. Non-limiting examples of amines comprise N,N-dibenzylethylenediamine, chloro-procaine, choline, diethanolamine, ethylenediamine, N-methyl-glucamine and procaine.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As an exemplary embodiment, pharmaceutical combinations of the invention can be administered orally, either in the form of tablets containing excipients such as starch or lactose, or in capsules, either alone or mixed with excipients, or in the form of syrups or suspensions containing coloring or flavoring agents. They can also be injected parenterally, for example intramuscularly, intravenously or subcutaneously. In parenteral administration, they can be used in the form of a sterile aqueous solution which can contain other solutes, such as, for example, any salt or glucose in order to make the solution isotonic.

The compounds of the present invention can be administered to a subject for the treatment of pain, for example orally, either covered in gelatin capsules or compressed in lozenges. For oral therapeutic administration, said compounds can be mixed with excipients and used in the form of lozenges, tablets, capsules, elixirs, suspensions, syrups, wafers, chewing gum, and the like. These preparations could contain at least 0.5% of active compound, but can vary depending on each form, in particular between 4% and 75% approximately of the weight of each unit. The amount of active compound in such compositions should be that which is necessary for obtaining the corresponding dosage. For example, the compositions and preparations as described herein can be prepared in such a way that each oral dosage unit can contain between 0.1 mg and 300 mg of the active compound.

In parenteral therapeutic administration, the active compounds of this invention can be incorporated in a solution or suspension. Such preparations, for example, can contain at least 0.1% of the active compound, but can vary between 0.5% and 50% approximately of the weight of the preparation. For example, such preparations comprise about 0.1%, 0.5%, 1%, 5%, 10%, 15%, 25%, 30%, 35%, 40%, 45%, 50%, of the weight of the preparation. The amount of active compound in such compositions should be that which is necessary for obtaining the corresponding dosage. The compositions and preparations as described herein can be prepared in such a way that each parenteral dosage unit can contain between 0.01 mg and 1000 mg, for example between about 0.5 mg and 100 mg of the active compound, for example. While intramuscular administration can be given in a single dose or divided into up to multiple doses, such as three doses, intravenous administration can include a drip device for giving the dose by venoclysis. Parenteral administration can be performed by means of ampoules, disposable syringes or multiple-dose vials made of glass or plastic.

Pharmaceutical compositions suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). In embodiments, the composition can be sterile and should be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can occur by including an agent in the composition which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds of the present invention can be administered to a subject for the treatment of pain in a single dose, or as multiple doses over a period of time. Further, the compound can be administered at intervals of about 4 hours, 8 hours, 12 hours, 24 hours, or longer. For example, a pill can be administered to a subject prior to the onset of pain to prevent pain, or a multiple pills can be administered over a period of time to ameliorate pain over said period.

Of necessity, there will be variations which will depend on the weight and conditions of the subject to be treated and on the particular administration route selected.

Methods of Treatment

Embodiments can be used for the treatment or amelioration of pain, non-limiting examples of which comprise post-surgical, neuropathic, dental, ophthalmic, arthritic, post- and/or traumatic pain.

In embodiments, a compound as described herein, such as SRP6D or SRP6R, is used as the only physically active compound in the treatment of neuropathic pain without a second active agent, such as GABA analogous, such as Gabapentin (Neurontin).

In other embodiments, the compositions as described herein can be administered to a subject concurrently with and/or in combination with a second active ingredient, such as an opioid or an non-steroidal anti-inflammatory drug (NSAID). Opioid drugs work by binding to opioid receptors in the brain and spinal cord. Non-limiting examples such opioids comprise codeine, fentanyl, hydrocodone, hydrocodone/ApAP, hydromorphone, meperidine, methadone, morphine, oxycodone, oxycodone and ApAP, oxycodone and naloxone. Nonsteroidal anti-inflammatory drugs (NSAIDs) block the COX enzymes and reduce prostaglandins throughout the body. As a consequence, ongoing inflammation, pain, and fever are reduced. Non-limiting examples of NSAIDs comprise aspirin, celecoxib, diclofenac, diflunisal, etodolac, ibuprofen, indomethacin, ketoprofen, ketorolac, nabumetone, naproxen, oxaprozin, piroxicam, salsalate, sulindac, and tolmetin.

Compounds of as described herein, for example SRD6R and SRP6D, can be incorporated into pharmaceutical compositions suitable for administration. Such compositions can comprise a compound as described herein and a pharmaceutically acceptable carrier. Thus, in some embodiments, the compounds of the invention are present in a pharmaceutical composition.

For example, a pharmaceutical compositions comprising a compound as described herein can be used for preventing and/or treating pain, such as a therapeutically effective amount of SRP6D and SRP6R in admixture with a pharmaceutical acceptable carrier or excipient. For example, a therapeutically effective amount of SRP6D can be administered to a subject so as to prevent the onset of pain, or prevent the severity of pain from increasing.

"Treatment" can refer to an approach for obtaining beneficial or desired clinical results, for example improvement or alleviation of any aspect of pain, such as acute, chronic, inflammatory, neuropathic, or post-surgical pain. Beneficial or desired clinical results comprise, but are not limited to, one or more of the following: including lessening severity, alleviation of one or more symptoms associated with pain including any aspect of pain (such as shortening duration of pain, and/or reduction of pain sensitivity or sensation).

"Ameliorating" pain or one or more symptoms of pain can refer to a lessening or improvement of one or more symptoms of a pain as compared to not administering a composition as described here, such as SRP6D and SRP6R. "Ameliorating" can also comprise shortening or reduction in duration of a symptom. For example, a therapeutically effective amount of SRP6D or SRP6R can be administered to a subject afflicted with pain so as to ameliorate, or lessening, the pain.

The term "alleviate" or "alleviating" can refer to lightening or lessening the severity of a symptom, condition, or disorder. For example, a treatment, such as SRP6D or SRP6R, that reduces the severity of pain in a subject can be said to alleviate pain. For example, a therapeutically effective amount of SRP6D can be administered to a subject afflicted with pain, wherein the severity of the pain is lessened. It is understood that, in certain circumstances, a treatment can alleviate a symptom or condition without treating the underlying disorder. In certain aspects, this term can be synonymous with the language "palliative treatment."

Embodiments can be used for reducing the incidence of pain or delaying, non-limiting examples of which comprise post-surgical, neuropathic, dental, ophthalmic, arthritic, post- and/or traumatic pain. "Reducing incidence" of pain can refer to any of reducing severity (which can include reducing need for and/or amount of (e.g., exposure to) other drugs and/or therapies generally used for this conditions), duration, and/or frequency (including, for example, delaying or increasing time to pain in an individual). As is understood by those skilled in the art, individuals can vary in terms of their response to treatment, and, as such, for example, a "method of reducing incidence of pain in an individual" reflects administering compositions as described herein, such as SRP6D and SRP6R, based on a reasonable expectation that such administration can cause such a reduction in incidence in that particular individual.

"Delaying" the development of pain can refer to deferring, hindering, slowing, retarding, stabilizing, and/or postponing progression of pain. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method.

"Development" or "progression" of pain can refer to initial manifestations and/or ensuing progression of the disorder. Development of pain can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of pain includes initial onset and/or recurrence. For example, embodiments as described herein can be used to prevent the development of pain, or prevent the progression of pain.

Embodiments can be used for palliating pain, non-limiting examples of which comprise post-surgical, neuropathic, dental, ophthalmic, arthritic, post- and/or traumatic pain.

"Palliating" pain or one or more symptoms of pain can refer to lessening the extent of one or more undesirable clinical manifestations of pain in an individual or population of individuals treated with a composition as described herein, such as SRP6D and SRP6R.

Embodiments comprise administering to a subject an effective amount of a composition as described herein, such as SRP6D and SRP6R, for the treatment of pain.

An "effective amount", "sufficient amount" or "therapeutically effective amount" can refer to an amount sufficient to effect beneficial or desired clinical results including alleviation or reduction in the pain sensation. For purposes of this invention, an effective amount of a composition as described herein, such as SRP6D and SRP6R, can comprise an amount sufficient to treat, ameliorate, reduce the intensity of or prevent pain of any sort, including acute, chronic, inflammatory, neuropathic, or post-surgical pain. In some embodiments, an effective amount of compositions as described herein can modulate the sensitivity threshold to external stimuli to a level comparable to that observed in healthy subjects. In other embodiments, this level is not be comparable to that observed in healthy subjects, but is reduced compared to not receiving the combination therapy.

Specific compositions as described herein, such as SRP6D and SRP6R, can be administered to a subject by any suitable means, such as oral, intravenous, parenteral, subcutaneous, intrapulmonary, topical, intravitreal, dermal, transmucosal, rectal, and intranasal administration. Parenteral infusions include intramuscular, intravenous, intraarterial, or intraperitoneal administration. The compounds can also be administered transdermally, for example in the form of a slow-release subcutaneous implant or as a transdermal patch. They can also be administered by inhalation. Although direct oral administration may cause some loss of desired activity, for example pain relieving activity, the analgesics can be packaged in such a way to protect the active ingredient(s) from digestion by use of enteric coatings, capsules or other methods known in the art.

Controlled-release pharmaceutical products have a common goal of improving drug therapy over that achieved by their non-controlled counterparts. The use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Solutions or suspensions used for parenteral, intradermal, or subcutaneous application can include, for example, the following components: a sterile diluent such as water for injection, saline solution, fixed oils, polyethylene glycols, glycerine, propylene glycol or other synthetic solvents; anti-inflammatory agents; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Compositions as described herein, such as SRP6D and SRP6R, can be administered to the subject one time (e.g., as a single injection or deposition). While the term for administering of at least one compound to prevent pain varies depending on species, and the nature and severity of the condition to be prevented or treated, the compound can be administered to humans for a short term or a long term, i.e. for 1 week to 1 year. For example, administration can be once or twice daily to a subject in need thereof for a period of time, such as one week or one month.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In an embodiment, the recommended daily dose range of a compound as described herein for pain as described herein lies within the range of from about, a daily dose of about 1 mg/body to about 10 g/body, for example about 5 mg/body to about 5 g/body, or for example about 10 mg/body to about 2 g/body of the active ingredient is generally given for treating this disease, and an average single dose of about 0.5 mg to about 1 mg, about 5 mg, about 10 mg, about 50 mg, about 100 mg, about 250 mg, about 500 mg, about 1 g, about 2 g and about 3 g is generally administered. Daily dose for administration in humans for treating or ameliorating pain could be in the range of about 1 mg/kg to about 300 mg/kg.

A compound as described herein, for example SRP6D or SRP6R, or composition comprising the same can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal (e.g., cream, lotion, or dermal spray) or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions or solutions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms for parenteral administration to a subject.

The composition, shape, and type of dosage forms of the disclosure will typically vary depending on their use. Further, the dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

For example, a dosage form used in the acute treatment of a disease can contain larger amounts of one or more of the active agents it comprises than a dosage form used in the chronic treatment of the same disease. Similarly, a parenteral dosage form can contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat, pig, or human. In some embodiments, the subject is a mouse. In some embodiments, the subject is a rat. In some embodiments, the subject is a pig. In some embodiments, the subject is a human.

Medical Kits

A "kit" or "medical kit" of the disclosure comprises a dosage form of a compound of the disclosure, such as SRP6D or SRP6R, or a pharmaceutically acceptable salt, solvate, hydrate, stereoisomer, prodrug, or clathrate thereof. A kit can also include both SRP6D and SRP6R, either in combination, such as in a single tablet, or provided separately, such as in two tablets.

Kits can further comprise additional active agents, for example opioids or non-steroidal anti-inflammatories, examples of which are described herein. For example, an opioid can be provided in a kit described herein at dose lower than that currently used by a subject so as to decrease total body opioid consumption and the deleterious effects associated with prolonged opioid use. Kits of the disclosure can further comprise devices that are used to administer the active ingredients. Examples of such devices include, but are not limited to, syringes, drip bags, patches, and inhalers. Kits can also comprise printed instructions for administering the compound to a subject.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Discovery of ApAP Analogs with Retained Analgesia and Minimal Hepatotoxicity

Although ApAP is one of the most commonly used medicines worldwide, hepatotoxicity is the most significant risk, and overdose or use in patients with compromised liver function is the most common cause of fulminant hepatic failure. Oxidation of ApAP to the metabolite N-acetyl-p-benzoquinone imine (NAPQI) is the likely mechanism for the hepatotoxicity. We previously synthesized an ApAP analogue bearing a heterocyclic moiety linked to the p-acylaminophenol fragment. Analogs to the metabolite of this ApAP analog were synthesized (SRP 6D and R) to further enhance the safety profile of these new chemical entities while retaining analgesia. These novel compounds display analgesia comparable to ApAP with retained antipyresis in a mouse model, while exhibiting decreased hepatotoxicity in human hepatocytes (hHEPs). Compared to ApAP, SRP 6D and R resulted in decreased lactate dehydrogenase and increased reduced glutathione in hHEPs and demonstrated a favorable cytochrome P450 metabolism and marked decreased liver function tests in an in vivo mouse model. Given the widespread use of ApAP as a standalone medication and in various combination formulations, this preclinical data establishes a novel pipeline of compounds to develop that maintain analgesia but have markedly diminished hepatotoxicity.

Introduction

Acetaminophen, ApAP, also known as paracetamol, is N-acetyl-para-aminophenol (ApAP), the most common over the counter analgesic used worldwide[2]. The chemical structures of ApAP, n-acetyl-p-aminophenol, and ApAP metabolite N-arachidonoylphenolamine (AM404), are below:

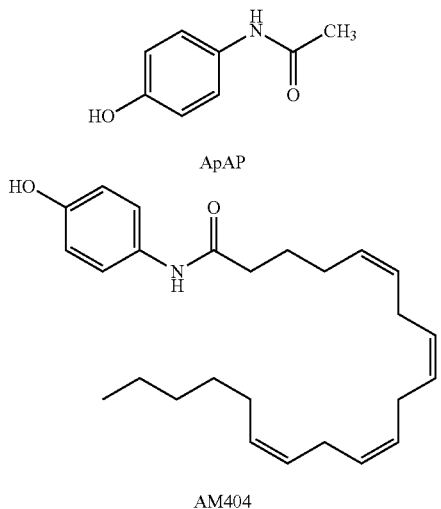

An analine analgesic, it was synthesized in the 1878 in search of a safer acetanilide derivative devoid of methemoglobinemia toxicity causing cyanosis with analgesic and antipyretic activity, and briefly introduced into clinical practice in 1887[3]. However, it was not widely adopted as an analgesic until the 1950s after Brodie and Axelrod demonstrated that ApAP was the major metabolite of the analines, acetanilide and phenacetin[4], devoid of methemoglobinemia and nephropathy, re-introducing ApAP.

Even though it has been used over several decades, ApAP has a rather narrow therapeutic index and significant side effects are associated when overdose occurs, primarily hepatotoxicity. Hepatotoxicity has been the major caveat with use of ApAP, primarily due to accidental or intentional overdose being the most common cause of fulminant hepatic failure in the United States[5] and in the Western world[2], requiring aggressive intensive care support and, in rare cases, liver transplantation[6]. Cases of ApAP hepatotoxicity may also occur in patients with compromised liver function not ingesting large doses of ApAP. Hepatotoxicity occurs via is oxidation of ApAP to the corresponding N-acetyl-p-benzoquinone imine (NAPQI)[2, 7] thru cytochrome P450 metabolism, with resultant glutathione depletion, mitochondrial dysfunction and oxidative stress.

Despite this long history, ApAP mechanism of action is still unclear, and this has been a challenge towards designing safer analgesic and antipyretic analogs. Distinct from non-steroidal anti-inflammatory drugs (NSAIDs), which principally have anti-inflammatory and only moderate analgesia and anti-pyretic effects through inhibition of cyclooxygenases (COX-1, -2), whether or not ApAP is a COX inhibitor has been debated as it has no appreciable clinical anti-inflammatory functions. Some suggest it possesses the ability to act as a COX-inhibitor by reducing the protoporphyrin radical cation in the peroxidase site of prostaglandin H2 synthases (COX-enzymes)[8], thereby reducing the prostaglandins responsible for pyrexia[9].

The discovery in 2005 of the ApAP metabolite N-arachidonoylphenolamine (AM404, FIG. 1) as the amide formed from 4-aminophenol and arachidonic acid by fatty amide hydrolase in the brain and spinal cord [10] suggest that ApAP may exert its effects thru activation of the capsaicin receptor/TRPV1 (transient receptor potential cation channel, subfamily V, member 1) [11] and/or the cannabinoid CB1 receptor system [12]. These putative mechanisms of action have led to the development of ApAP analogs, including an adamantyl analog of ApAP [13] that targets the TRPA1 ion channel (transient receptor potential cation channel subfamily A member 1). Another strategy employed has been to target the cannabinoid receptors CB1 and CB2 thru modification of the main metabolite of ApAP, AM404, by placing an anandamide chain instead of the acetamido group [14].

We have taken another approach, creation of novel ApAP analogs that are not metabolized to NAPQI and, hence, result in minimal hepatotoxicity. This was achieved by replacing the methyl group with saccharin and various derivatives and analogs thereof, creating 2-(1,1-dioxido-3-oxo-1,2-benzisothiazol-2(3H)-yl)-N-(4-hydroxyphe-nyl) alkanecarboxamides, bearing a heterocyclic moiety linked to the p-acylaminophenol fragment (SCP-1)[15]. This modification also improves considerably its water solubility and maintains analgesia[16]. Here we describe the synthesis of novel analgesics, 2-<[(4-Hydroxy-phenylcarbamoyl)-methyl]-sulfamoyl>-n,n-diethyl-benzamide (SRP-6D) and n-[2-(2,3-Dihydroxyphenyl)-ethyl-2-<[(4-hydroxy-phenyl-carbamoyl)-methyl]-sulfamoyl>-benzamide (SRP-6R, FIG. 1), which are analogs to the metabolite of SCP-1 (SCP-1M) that display analgesia, a favorable cytP450 metabolism profile and minimal hepatotoxicity.

Methods

Synthesis of Saccharin Derivatives

Preparation of Starting Material 5 and Saccharin Derivatives 7

2-Chloro-N-(4-hydroxyphenyl)acetamide 3 was synthesized by acylation of 4-aminophenol 1 with 2-chloroacetic anhydride, using a heterogeneous silica gel supported NaHSO4 catalyst (NaHSO4. SiO2) in CH2Cl2 at room temperature. Compound 3 was obtained in 75% yield (Scheme 1).

Scheme 1

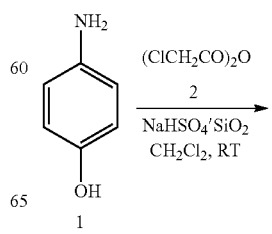

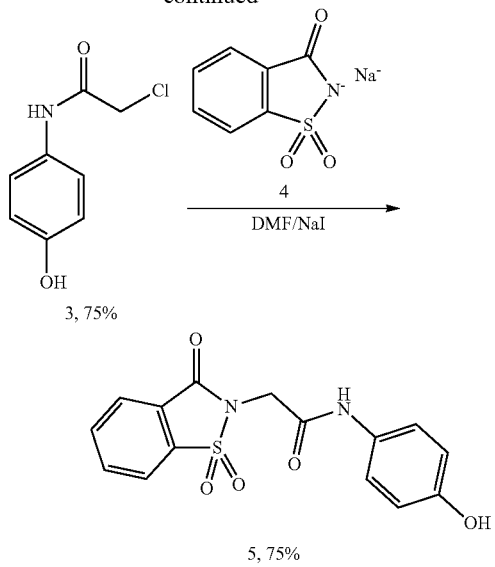

3, 75%

5, 75%

Preparation of compound 5 was carried out by using the procedure described by Trudell et al[17]. Thus, 2-chloro-N-(4-hydroxy-phenyl) acetamide 3 and saccharin sodium salt 4 were heated to reflux in DMF with catalytic amount of NaI. The saccharin derivate 5 was obtained by precipitation in ice/water and crystallized in ethanol/water, to give compound 5 (Scheme 1).

Reaction between compound 5 and amines 6 produces the opening of the saccharin heterocyclic ring to give the desired N-substituted amides (Scheme 2). These reactions are carried out mostly in aqueous solution until complete disappearance of 5 by TLC.

Scheme 2

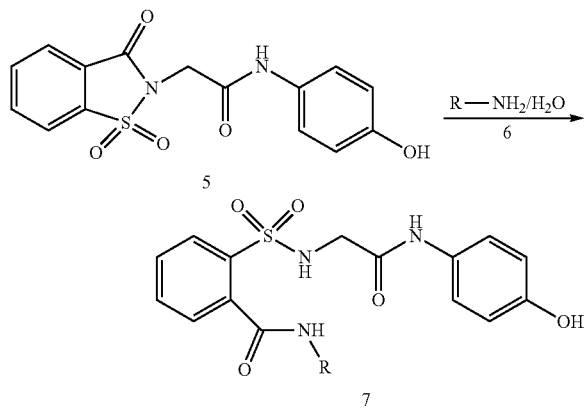

Preparation of Saccharin Derivatives

NaHSO$_4$—SiO$_2$ catalyst. To a solution of 4.14 g (0.03 mol) of NaHSO$_4$.H$_2$O in 20 mL of water was added 10 g of silica gel (column chromatographic grade, 60 Å, 200-400 mesh). The mixture was stirred for 15 min at room temperature and then gently heated in the rotary evaporator, until a free-flowing white solid was obtained. The catalyst was further dried under vacuum for at least 48 h prior to use.

2-Chloro-N-(4-hydroxyphenyl)acetamide, 3. To a mixture of 4-aminophenol 1 (4.36 g, 40 mmol) and 2-chloroacetic anhydride 2 (8.2 g, 48 mmol) in CH$_2$Cl$_2$ (200 mL) NaHSO$_4$. SiO$_2$ (4 g) was added. The mixture was heated to 35° C. for 2.5 h and the reaction was monitored by TLC. The precipitate was dissolved in ethanol and the mixture was filtered. The filtrate was concentrated and the residue washed with water, to give 3 (5.74 g, 75%) as a white solid: mp 142-144° C.; $^1$H NMR (300 MHz DMSO-d$_6$) δ 4.18 (s, 2H, CH$_2$), 6.71 (d, 2H, J=8.9 Hz, H-1,5), 7.36 (d, 2H, J=8.9 Hz, H-2,4), 9.27 (s, 1H, OH), 10.03 (s, 1H, NH) ppm. $^{13}$C NMR (75 MHz DMSO-d$_6$) δ 44.0, 115.6, 121.6, 130.5, 154.2, 164.3.ppm.

2-(1,1-Dioxo-1,2-dihydrobenzo[d]isothiazol-3-one-2-yl)-N(4-hydroxyphenyl) acetamide, 5. 2-Chloro-N-(4-hydroxyphenyl)acetamide 3 (5 g, 27 mmol) and saccharin sodium monohydrate 4 (7.25 g, 32.4 mmol) salt were mixed together in the presence of NaI (0.015 g, 2.30 mmol) in DMF (15 mL). The mixture was heated to reflux (160° C.) for 2 h, cooled to 25° C., and poured into cold water until no additional precipitate formed to displace the DMF. The sticky white precipitate was collected by vacuum filtration and allowed to dry in air for 90 min. The filter cake was dissolved in 50% ethanol-water and crystallized to furnish 6.72 g of 5 as white crystals 75% yield: mp 204-207° C.; $^1$H NMR (300 MHz DMSO-d$_6$) δ 4.52 (s, 2H, CH$_2$), 6.71 (d, 2H, J=8.5 Hz, H-1,5), 7.34 (d, 2H, J=8.5 Hz, H-2,4), 8.05 (m, 2H, 2H-arom), 8.15 (d, 1H, J=7.1, H-arom), 8.35 (d, 1H, J=7.4, H-arom), 9.26 (s, 1H, OH), 10.06 (s, 1H, NH) ppm. $^{13}$C NMR (75 MHz DMSO-d$_6$) δ 40.6, 115.2, 121.0, 121.8, 125.2, 126.5, 130.1, 135.5, 135.9, 136.0, 153.7, 158.8, 162.6 ppm.

2-<[(4-Hydroxy-phenylcarbamoyl)-methyl]-sulfamoyl>-N-methyl-benzamide (7a). OSA-6c To methylamine aqueous solution (10 mL, 40% 119 mmoL) compound 5 (0.6 g, 1.8 mmol) was added. The mixture was stirred for 35 min and dried under vacuum to give a white solid. This compound was purified by flash column chromatography (Ethyl acetate/Hexane 9:1) to give 0.59 g, 89%: mp 93-95° C. $^1$H NMR (300 MHz, DMSO-d$_6$) δ, 2.80 (d, 3H, J=4.5 Hz, CH3), 3.67 (s, 2H, CH2), 6.64 (d, 2H, J=8.8 Hz, H-1,5), 7.20 (d, 2H, J=8.8 Hz, H-2,4), 7.49 (s, 1H, NH), 7.55 (d, 1H, J=7.2 Hz, H-arom), 7.65 (m, 2H, H-arom), 7.86 (d, 1H, J=7.4 Hz, H-arom), 8.69 (s, 1H, J=4.5 Hz, NH), 9.20 (s, 1H, NH), 9.76 (s, 1H, OH) ppm. $^{13}$C NMR (75 MHz, DMSO) δ 26.7, 39.1, 39.4, 39.7, 39.9, 40.2, 40.5, 40.8, 46.3, 115.4, 129.0, 121.4, 129.6, 130.3, 130.4, 133.2, 136.2, 137.2, 153.9, 165.8, 169.2 ppm.

Scheme 3

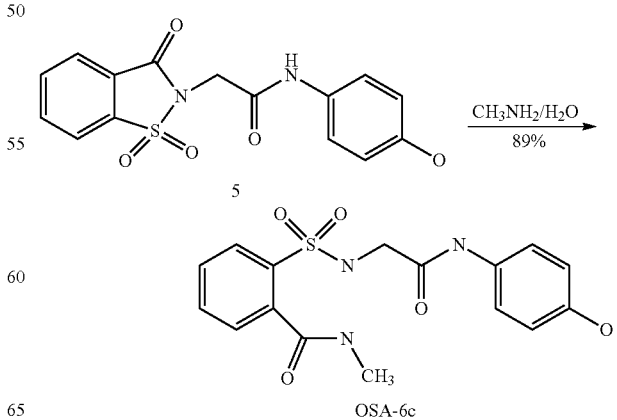

OSA-6c

2-<[(4-Hydroxy-phenylcarbamoyl)-methyl]-sulfamoyl>-N,N-diethyl-benzamide (7b). OSA-6d To a solution of diethylamine (0.657 g, 0.93 mL, 9 mmol) in water (15 mL) compound 5 (1 g, 3 mmol) was added. The mixture was stirred for 2 h at room temperature. The obtained solid was dried under vacuum and was purified by flash column chromatography (Ethyl acetate/EtOH 6:4) to supply a white solid (0.960 g, 76%): mp 187-189° C.; $^1$H NMR (300 MHz, DMSO) δ 1.19 (t, J=7.2 Hz, 6H, 2CH$_3$), 2.93 (q, J=7.2 Hz, 4H, 2CH$_2$), 3.55 (s, 2H, CH$_2$), 6.63 (d, J=8.7 Hz, 2H, H-arom), 7.23 (d, J=8.7 Hz, 2H, H-arom), 7.40 (t, J=7.2 Hz, 1H), 7.52 (t, J=7.1 Hz, 1H, H-arom), 7.60 (d, J=7.2 Hz, 1H, H-arom), 7.73 (d, J=7.5 Hz, 1H, H-arom), 8.93 (bs, 1H, NH), 9.20 (bs, 1H, NH), 9.99 (s, 1H, OH)ppm. $^{13}$C NMR (75 MHz, DMSO) δ 11.1, 41.3, 46.4, 114.8, 120.8, 127.1, 127.2, 129.9, 130.0, 132.0, 135.3, 141.6, 153.2, 165.4 ppm.

Scheme 4

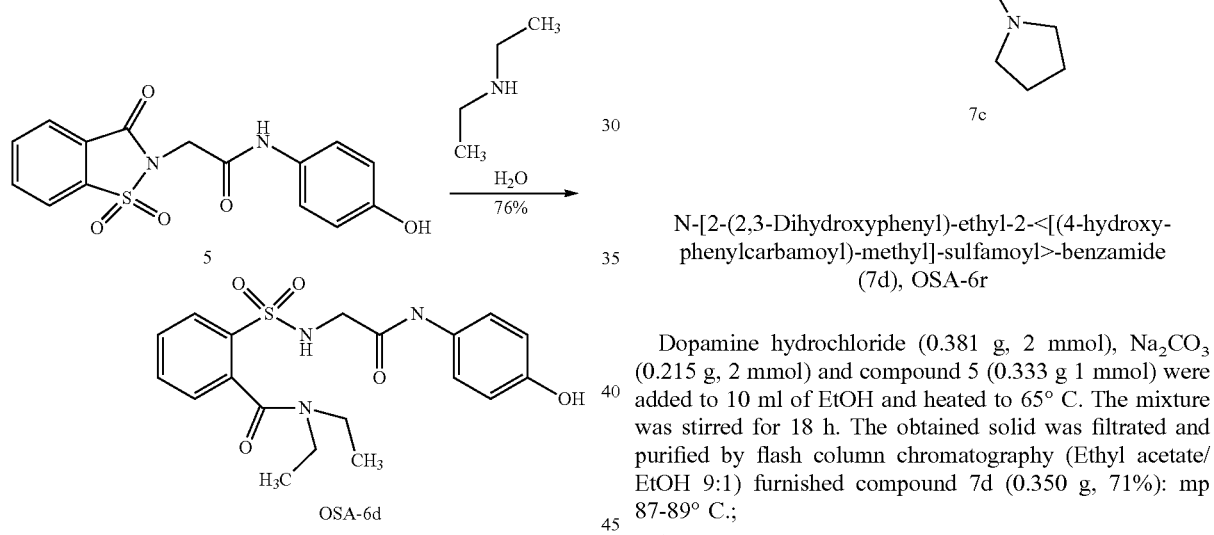

OSA-6d

2-<[(4-Hydroxy-phenylcarbamoyl)-methyl]-sulfamoyl>-N-(2-pyrrolidin-1-yl-ethyl)-benzamide (7c). OSA-6u To a solution of 1-(2-aminoethyl)pyrrolidine (0.684 g, 0.76 mL, 6 mmol) in acetonitrile (15 mL) compound 5 (0.941 g, 2.8 mmol) was added. The mixture was stirred for 1 h at room temperature. The obtained solid was filtrated and purified by flash column chromatography (Ethyl acetate/EtOH 9:1) to supply a white solid (1.1 g, 80%): mp 141-142° C.; $^1$H NMR (300 MHz, DMSO) δ 1.71 (s, 4H), 2.54 (s, 4H), 2.64 (s, 2H), 3.43 (s, 2H), 3.85 (s, 2H), 6.59 (d, J=7.8 Hz, 2H), 6.95 (d, J=7.7 Hz, 2H), 7.44 (dd, J=7.4 Hz, 2H), 7.56 (t, J=7.5 Hz, 1H), 7.80 (d, J=7.7 Hz, 1H), 9.21 (s, 1H), 8.81 (s, 1H), 9.87 (s, 1H) ppm. $^{13}$C NMR (75 MHz, DMSO) δ 23.6, 38.2, 46.0, 53.4, 54.5, 115.7, 122.2, 129.5, 129.8, 133.2, 137.2, 137.5, 154.5, 166.9, 167.8 ppm.

Scheme 5

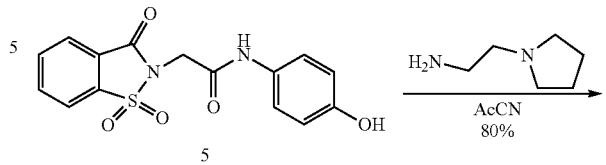

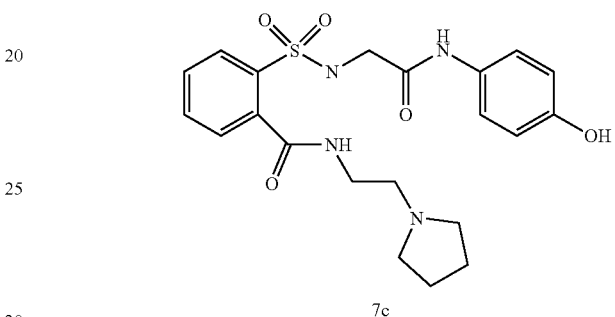

7c

N-[2-(2,3-Dihydroxyphenyl)-ethyl-2-<[(4-hydroxy-phenylcarbamoyl)-methyl]-sulfamoyl>-benzamide (7d), OSA-6r Dopamine hydrochloride (0.381 g, 2 mmol), Na$_2$CO$_3$ (0.215 g, 2 mmol) and compound 5 (0.333 g 1 mmol) were added to 10 ml of EtOH and heated to 65° C. The mixture was stirred for 18 h. The obtained solid was filtrated and purified by flash column chromatography (Ethyl acetate/EtOH 9:1) furnished compound 7d (0.350 g, 71%): mp 87-89° C.;

$^1$H NMR (300 MHz, DMSO) δ 2.68 (t, J=7.4 Hz, 2H, CH$_2$), 3.40 (t, J=6.8 Hz, 2H, CH$_2$), 3.68 (d, J=5.8 Hz, 2H, CH$_2$), 6.50 (dd, J=8.0, 1.5 Hz, 1H, H-arom), 6.70-6.58 (m, 4H), 7.21 (d, J=8.7 Hz, 2H, H-arom), 7.50-7.39 (m, 2H, H-arom, NH), 7.63 (dq, J=7.5, 6.8 Hz, 2H, H-arom), 7.87 (dd, J=7.3, 1.0 Hz, 1H, H-arom), 8.65 (s, 1H, OH), 8.77 (s, 1H, OH), 8.82 (t, J=5.6 Hz, 1H, NH), 9.18 (s, 1H, NH), 9.75 (s, 1H, OH) ppm. $^{13}$C NMR (75 MHz, DMSO) δ 35.0, 42.1, 46.7, 115.7, 116.2, 116.7, 120.0, 121.6, 129.2, 129.8, 130.5, 130.6, 130.7, 133.4, 136.4, 137.4, 144.2, 145.7, 154.1, 165.9, 168.8 ppm.

Scheme 6

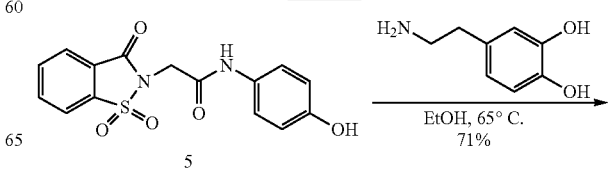

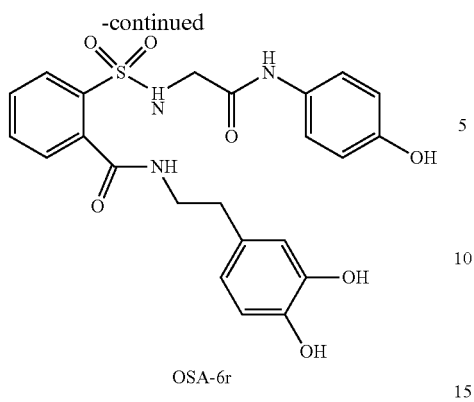

OSA-6r

Additional analogs of the above-described novel compounds were similarly formed via reaction of compound 5 with various reagents through processes similar to those described above with respect to select analogs of the herein-described novel analgesics. In certain embodiments, compound 5 was mixed with a desired reagent in a solution of water, ethanol, methanol, acetonitrile, tetrahydrofuran, aqueous methylamine, or any other organic or inorganic solvents known in the art as appropriate.

Potential reagents include $NH_3$, $NH(CH_3)_2$, $NH_2CH_3$, $NH(CH_2CH_3)_2$, $N_2(CH_2)_4HCH_2C_6H_5$, $NH_2(CH_2)_2C_6H_5$, $NH_2CH_2C_6H_5$, $NHO(CH_2)_4$, $NH_2CH_2CH_2CH_2CH_3$, $NH_2CH_2C_6H_4CH_3$, $NH_2CH_2C_6H_3Cl_2$, $NH_2CH_2C_6H_5CH_3$, $NH_2CH_2C_6H_5Cl$, $NH_2CH_2C_6H_5NO_2$, $NH_2C_5H_4$, $NH_2CH_2C(CH_3)_2$, $NH_2C(CH_3)_2$, $NH_2CH_2CH_2C_6H_3(OH)_2$, $NH_2CH_2C_6H_4N$, $NH_2CH_2C_6H_3NCH_3$, $NH_2CH_2CH_2C_4H_4N$, $NH(CH_3)CH_2CH_2OH$, $NH_2CH_2CH(OH)CH_2NH_2$; or pharmaceutically acceptable salts thereof.

Analogs created according to methods of synthesis described herein include compositions having the following chemical formulas:

6a
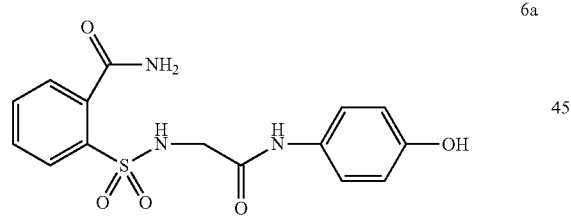

6b
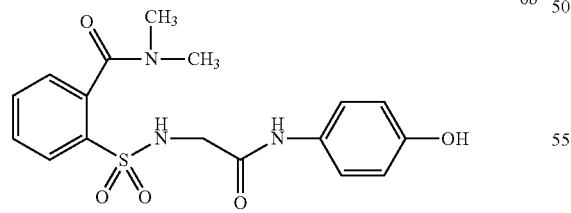

6c
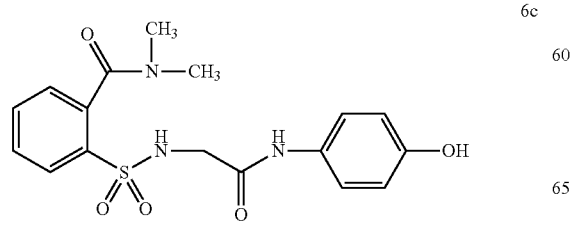

6d
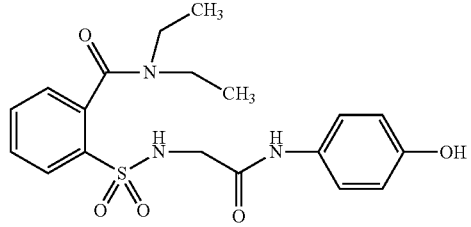

6e
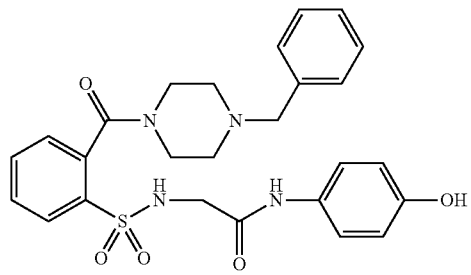

6f
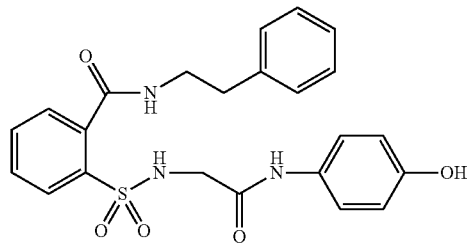

6g
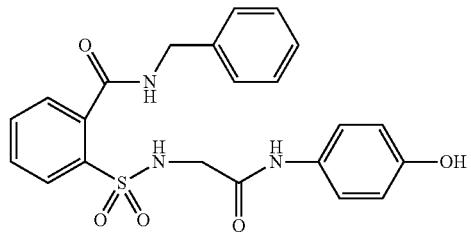

6h
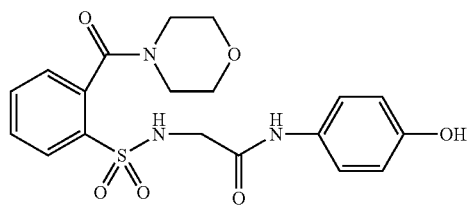

6i
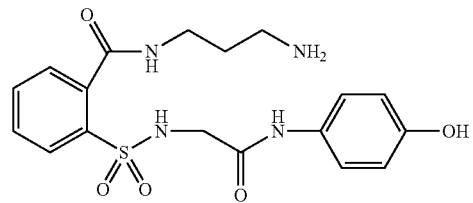

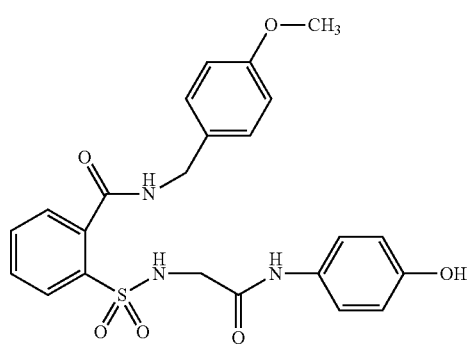
6j
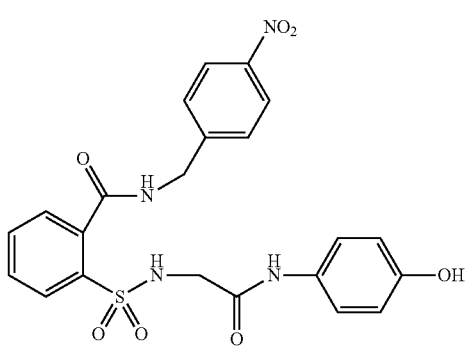
6n
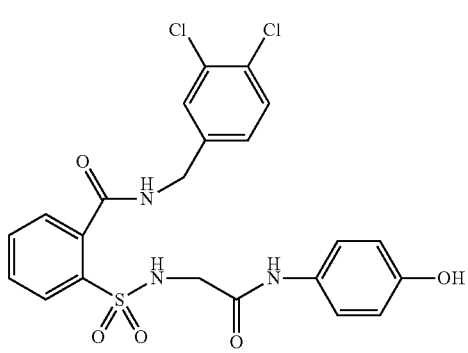
6k
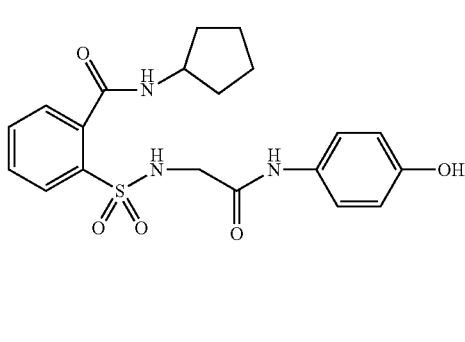
6o
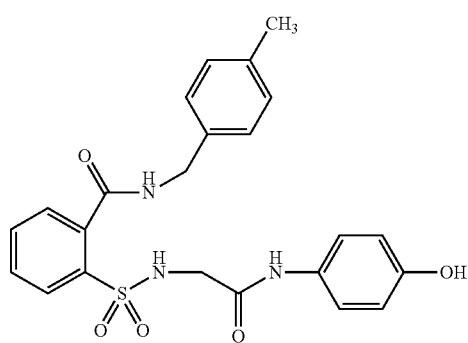
6l
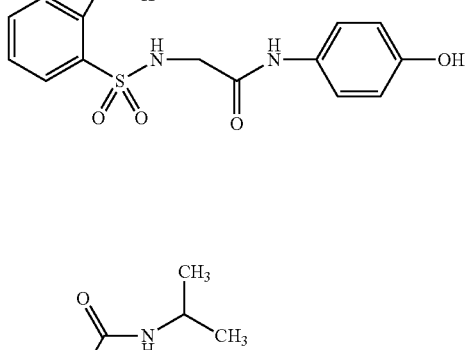
6p
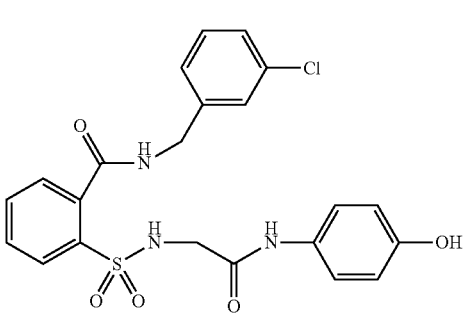
6m
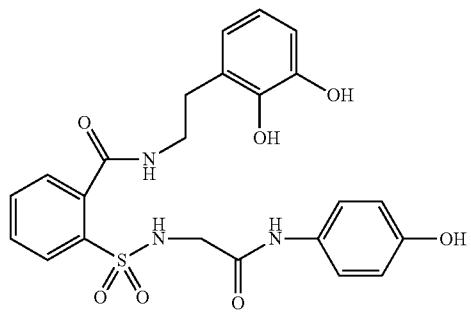
6q
6r

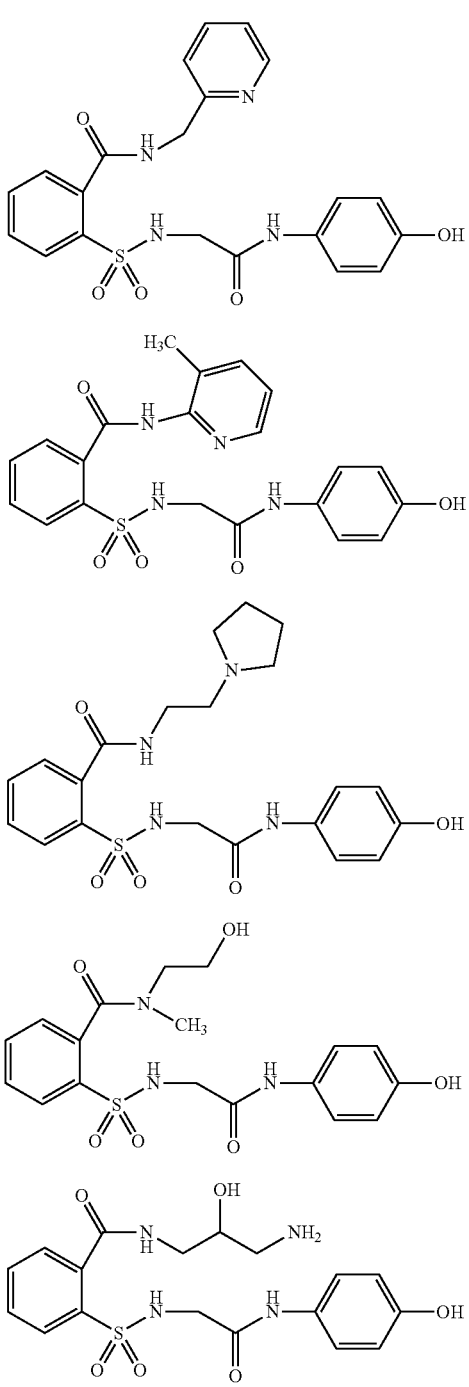

Analgesia Assays

Two different assays were utilized to quantify the analgesic effects of the compounds. All tests were performed on CD1 male mice. Compounds SCP-1, SCP-1M and SRP-6D,R (South Rampart Pharmaceuticals, New Orleans, La.), or APAP (Sigma, St. Louis, Mo.) and administered in a concentration of 75 mg/kg after suspension in the vehicle (0.9% saline). In some embodiments, the vehicle can comprise Agent K, 0.2%, Bio-serve, or Labrafil 1944 (Gottefosee, France). Compound or vehicle was administered orally by lavage under brief halothane anesthesia to animals fasted overnight.

Acetic acid-induced abdominal writhing assay. Contraction of the abdominal muscle and stretching of the hind limbs is induced as a response to intraperitoneal (ip) injection of an acetic acid solution, as described Hendershot and Forsaith, 1959. In this model of visceral pain, abdominal contractions (writhing) is induced in mice by an ip injection of 0.4% acetic acid at a dose of 10 mL/Kg, 25 min after drug administration. The number of writhes is counted for 10 min beginning 5 min after acetic acid injection. All animals (CD1 male mice) were fasted overnight (15 hours) prior to testing and the compounds were administered orally to animals belonging to the treatment groups, ApAP and SRP compounds at 75 mg/kg body weight). Data is expressed as mean±SEM, n=7.

Tail-flick assay. Analgesic effect of drugs was determined by using the reaction time (latency) of mice to thermal stimulation of the tail tip. All animals (CD1 male mice) were fasted overnight (15 hours) and, their baseline tail flick latency (seconds) was recorded using an IITC Tail Flick Analgesia Meter. The tail of each mouse was exposed to a focused beam of light and the latency to remove the tail from the path of the stimulus were recorded electronically using a photoelectric cell of the IITC Tail Flick Analgesia Meter. The stimulus intensity was adjusted to produce baseline latencies of 3-6 seconds. After measurement of baseline latency, drugs were administered per os to animals belonging to the treatment groups—(ApAP and SRP compounds at 600 mg/Kg body weight); control group received vehicle (0.9% saline only). At 30 minutes post injection, tail flick latency was recorded again to determine total change in latency. Percentage of maximum analgesia for each mouse were calculated with the formula, Percentage Analgesia=100*{[(Latency to tail flick after drug injection)-(Latency to tail flick at baseline)]/[(12 sec cutoff time)-(Baseline latency)]}. Data expressed as mean±SEM, n=10.

Antipyresis

The antipyretic effect of the compounds was assessed utilizing baker yeast-induced hyperthermia. All animals (CD1 male mice) were fasted overnight (15 hours) and, their baseline temperature was recorded using a Cole-Palmer rectal thermometer probe. Then they were injected thru the ip route with a pyrogenic dose of baker yeast (15% yeast, 0.1 ml/10 g body weight) while, control and vehicle group received an ip injection of vehicle (0.9% saline). Temperatures were again recorded at 4 hours, after which, the compounds were administered orally to febrile animals belonging to the treatment groups—(ApAP and SRP compounds at 300 mg/Kg body weight). Two hours post-injection, rectal temperatures were recorded once again, to determine total change in body temperature. Percentage Change in body temperature is calculated with the formula, Percentage Change=[(Total change in body temperature)/(Base temperature)*100]. Data is expressed as mean±SEM, n=10.

Cells/Cell Lines

Hepatocyte cell line (HEPG-2 cells) and primary human hepatocytes (hHEP).

HepaRG cells procured from Thermo Fisher Scientific (Invitrogen) are terminally differentiated hepatic cells, which are derived from a hepatic progenitor cell line that retains many characteristics of primary human hepatocytes. HepaRG cells were grown and maintained in EMEM containing NEAA (non-essential amino acids), supplemented with 10% fetal bovine serum (FBS), and incubated at 37° C./5% CO2. hHEP, purchased from SCKISUI Xenotech, were obtained from a 61 year-old Caucasian male individual donor who was a non-alcoholic and non-smoker. hHEP were grown in HCM (Clonetics, Walkersville, Md.), and maintained in HMM (Clonetics, Walkersville, Md.) at 37° C./5% CO2. Cultures (80% confluent) of HepaRG cells and hHEP growing in 6- and 24-well plates, respectively, were held 6-8 h in serum-free medium (EMEM, 0.5% FBS for HEPG-2, and HMM for primary hepatocytes) before the addition of analgesics. The serum-starved cells were treated with APAP, SRP-6D, R, SCP-1, SCP-1M or vehicle control for 6-8 h at 37° C.

Hepatotoxicity Testing for ApAP (APAP) Mediated Liver Injury (AILI) in Hepatocytes.

LDH assay. Using the Pierce LDH Cytotoxicity assay kit from Thermo Scientific, cells were incubated in presence of various drug compounds, followed by collection of the medium supernatant. Release of LDH was measured in 96 well plate formats. The absorbance was measured at 490 nm and 680 nm and the final result was absorbance observed at 680 nm subtracted from absorbance observed at 490 nm ($A_{490\ nm} - A_{680\ nm}$). GSH assay. Using the ThiolTracker Violet Glutathione Detection reagent from Molecular Probes (Invitrogen), after hepatocytes were incubated in the presence of various compounds, incubation medium was removed, cells rinsed with D-PBS conditioned medium followed by incubation with pre-warmed ThiolTracker Violet dye (working solution prepared as per manufacturer's instructions) for 30 minutes. Fluorescence was measured at the following wavelengths: excitation (404 nm) and emission (526 nm). The finalized result was expressed as relative fluorescence units (RFU), which indicates the cellular level of reduced glutathione (GSH) in intact cells.

Liver function assays. Alanine aminotransferase (ALT), aspartate aminotransferase (AST) and alkaline phosphatase (ALP) were run after dosing CD1 male mice with 600 mg/Kg of compounds—ApAP and SRP D and R orally, via gavage. The assays were run with serum collected from mice injected with compounds or vehicle, after overnight (15 hours) fasting. After drug administration, water and food were provided to the mice ad libitum.

Cytochrome P450 Enzyme Metabolism Profile

The VIVIDCYP450 screening assay kit (Life Technologies, Invitrogen/Thermo Fisher Scientific) was used as an in vitro high throughput screening. Here, each compound was mixed with a master pre-mix comprising of CYP450 BACULOSOMES (which are microsomes prepared from insect cells expressing a specific human P450 isoenzyme), reagent and regeneration system, which contained glucose-6-phosphate and glucose-6-phosphate dehydrogenase. The mixture was pre-incubated at room temperature for 20 minutes. Following this, each CYP enzyme specific substrate and $NADP^+$ were added and the mixture incubated at room temperature for 30 minutes. The reaction was stopped by addition of 0.5 M Tris base. CYP activity was evaluated by measuring the fluorescence of the fluorescent metabolite generated from each CYP enzyme specific substrate.

Statistics. Changes of the withdrawal thresholds or latencies induced by a drug were first analyzed with a one-way ANOVA. Comparisons between the effects of different drugs were then subjected to t-tests for unpaired means. A value of $p<0.05$ was considered significant.

Figure 11:
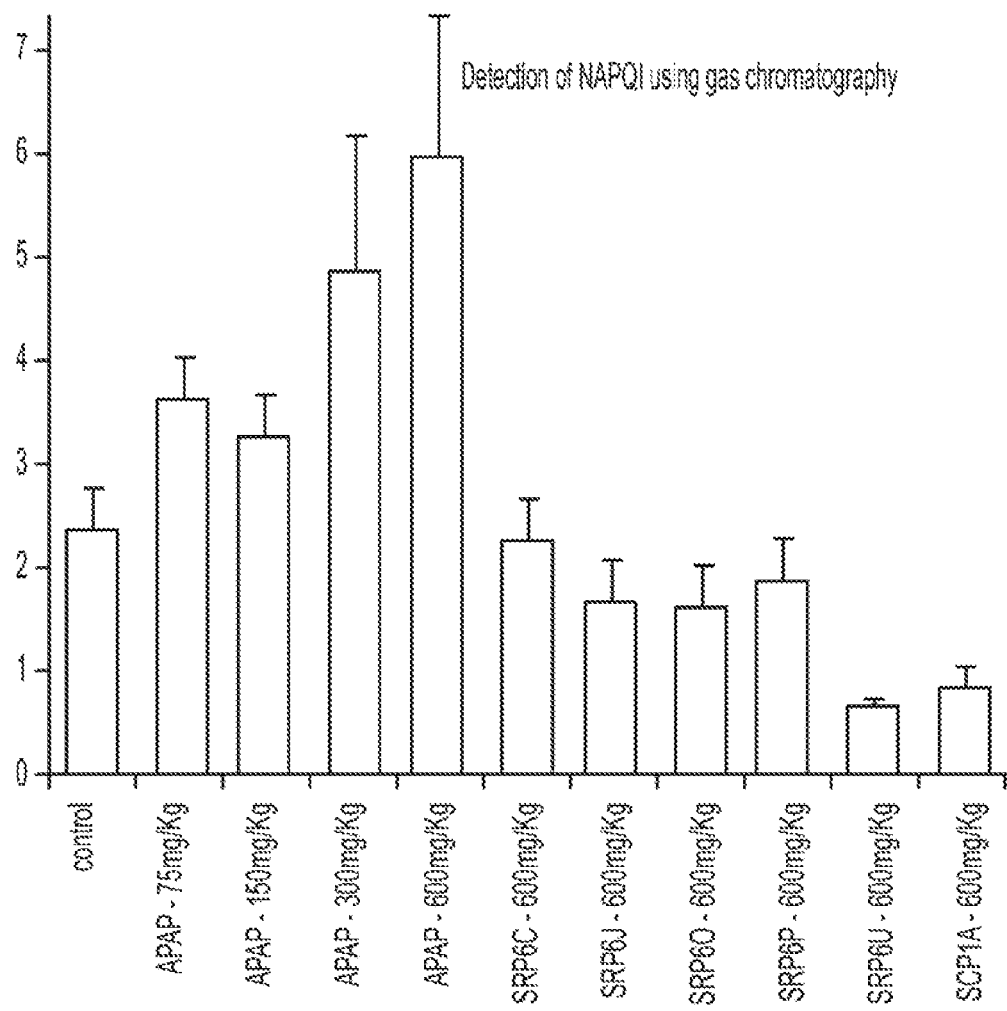
FIG. 11 is a bar graph showing results from gas chromatography used to detect a toxic metabolite, N-acetyl-benzoquinoneimine (NAPQI). Peak at 5.788.

Determination of metabolites: Gas chromatography was used to detect NAPQI (FIG. 11). Without being bound by theory, ApAP's toxicity is mediated via a toxic metabolite, N-acetyl-benzoquinoneimine (NAPQI), which depletes hepatic and renal glutathione, a cytoprotective endogenous metabolite. Gas chromatography demonstrates markedly lower levels of metabolism to NAPQI for select SRP compounds, compared to ApAP, explaining the decreased hepatotoxicity.

Two-month-old CD-1 mice were fasted overnight. Next morning, following light halothane anesthesia, they were given po 5a, 3 mmol/kg in Tween 20 (vehicle). They were placed in Nalgene metabolic cages (two mice per cage) with water ad libitum. Food was supplied 6 h post dose treatment. The urine was collected in a plastic container, which was maintained in ice during the 24-h collecting period. It was stored at 20° C. until use. At the time of the HPLC injection, aliquots were centrifuged in a microfuge at 6000 rpm, 15° C. for 10 min, filtered with nylon filters (0.45 μm), and used immediately or lyophilized.

In the HPLC-MS analysis, a volume of 20 lL was injected. When lyophilized samples were used, they were dissolved in a mixture of acetonitrile-0.1% ammonium acetate solution, pH 7 (50:50, v/v). The HPLC-MS analyses were performed in an Agilent 1100 apparatus. The analytical column was a Luna 150·4.6 mm, C18 (5 lm) Phenomenex column. The mobile phase was de-gassed automatically by the electronic degasser system. Before the analysis, the column was equilibrated and a gradient program was used for analysis of samples. The flow rate was maintained at 1.5 mL/min and the column was maintained at 45° C.

Results

Compound molecular weight and the calculated Log P (c Log P). Low Clog P values signify products with shorter half-lives, but higher c Log P values indicate potential difficulties with compound absorption. Hence, intermediate values around 2 are likely desirable, particularly for compounds to cross the blood-brain barrier.

TABLE 2

| Compound | Molecular weight (g/mol) | Clog P |
|---|---|---|
| ApAP | 151.16 | 0.416 |
| SCP1 | 332.33 | 1.28 |
| SCPM | 350.35 | From 1.07 to −2.48 |
| SRP6D | 405.47 | 1.42 |
| SRP6R | 485.51 | 1.89 |

A total of 21 compounds were synthesized in our project to discover novel chemical analogs to the metabolite of a heterocyclic moiety linked to the p-acylaminophenol fragment of ApAP but we focus on two (SRP 6D and R) that displayed analgesia comparable to ApAP, minimal hepatotoxicity, antipyresis, and a favorable cytochrome P450 metabolism. Analysis of the 21 compounds that were synthesized revealed some with low c Log P values, ~0.5, signifying likely poor bioavailability when used as oral drugs. However, SRP6D (Clog P: 1.42) and SRP6R (Clog P: 1.89) are comparable to ApAP (Clog P 0.91) and SCP-1 (Clog P 1.28), Table. Note that SCP-1M has an interval Clog P that ranges from 1.07 to −2.48 depending on medium pH because it has a polar ionizable group.

In two different in vivo analgesia mouse models, acetic acid-induced abdominal writhing and the tail flick assays, SRP6D and R are comparable to ApAP (FIG. 1). The number of writhes induced by injection of acetic acid was 15.7+/−1.2 (n=3) for SRP6D (n=7, p<0.02) and 9.5+/−4. for SRP6R (n=7, p<0.008; FIG. 1A), compared to 42.3+/−7.2 for vehicle only. A second set of experiments with n=7 demonstrates the analgesia of the various SRP compounds, which are similar to ApAP but lower than control (raw data for FIG. 1A):

TABLE 3

Analgesic activities of SRP compounds compared with ApAP as assessed by Acetic acid induced abdominal stretch (writhes) assay.

| Treatment Groups | No. of writhes counted within a 10 min time interval, 25 min post drug administration, beginning 5 min after acetic acid injection | | | | | | |
|---|---|---|---|---|---|---|---|
| Control | 42 | 41 | 31 | 30 | 29 | 25 | 24 |
| ApAP | 11 | 12 | 14 | 15 | 16 | 16 | 16 |
| SRP6D | 15 | 11 | 14 | 20 | 15 | 15 | 18 |
| SRP6I | 7 | 12 | 16 | 17 | 22 | 27 | 33 |
| SRP6J | 10 | 14 | 16 | 17 | 18 | 18 | 19 |
| SRP6O | 11 | 14 | 16 | 17 | 17 | 18 | 24 |
| SRP6P | 14 | 17 | 24 | 26 | 29 | 30 | 14 |
| SRP6R | 9 | 12 | 18 | 20 | 25 | 26 | 26 |

Note:
n = 7 for all treatment group; animals belonging to control group received 0.9% saline (vehicle) in lieu of drugs. Drugs of choice were administered per os (p.o.), at a dose of 75 mg/Kg body weight.

The tail flick test demonstrated a comparable significant analgesia for SRP6D, R to ApAP and marked improved latency compared to vehicle only (FIG. 1B).

Figure 4:
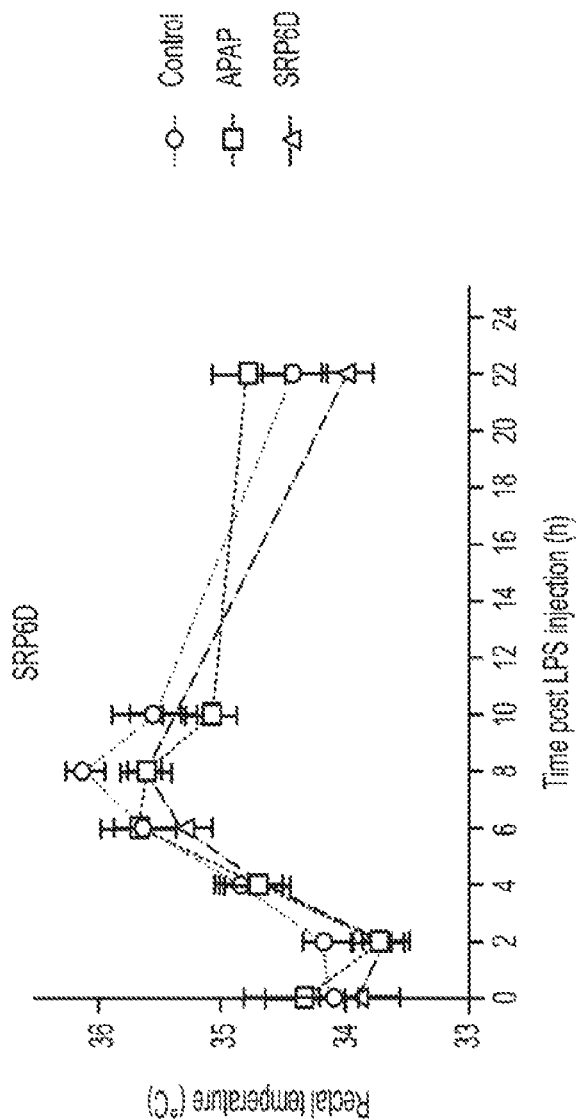
FIG. 4 shows an antipyretic effect for the SRP compounds. Temperature curves demonstrate comparable antipyresis to ApAP for A) SRP6D and B) SRP6R in an LPS-induced fever mouse model. Note that 2, 8 and 10 h, the antipyresis is similar for ApAP, SRP6D and SRP6R. A Baker's yeast-induced fever demonstrates similar antipyretic effects of ApAP, C) SRP6D and D) SRP6R, n=10 per group. E) Pyrogenic dose of baker yeast (15% yeast, 0.1 ml/10 g body weight; control received ip injection of vehicle, 0.9% saline) was done ip and temperatures were recorded at 4 hours, after which, drugs were administered orally to febrile animals belonging to the treatment groups— (ApAP and SRP compounds at 300 mg/Kg body weight). Two hours post injection, rectal temperatures determined total change in body temperature. Data expressed as mean±SEM, n=10.

SRP6D and SRP6R retain an antipyretic effect comparable to ApAP (FIG. 4). Antipyresis was determined using two different mouse assays. Temperature curves demonstrate comparable antipyresis to ApAP for SRP6D and SRP6R in an LPS-induced fever mouse model (FIG. 4A, B). Note that at 2 h, 8 h and 10 h, the antipyresis is similar for ApAP, SRP6D and SRP6R. A Baker's yeast-induced fever model of antipyresis demonstrated similar antipyretic effects of ApAP and SRP6D and SRP6R (FIG. 4C, D). Comparable effect of antipyretics on baker yeast-induced hyperthermia is noted in FIG. 4E for ApAP and SRP6D and SRP6R.

Figure 2:
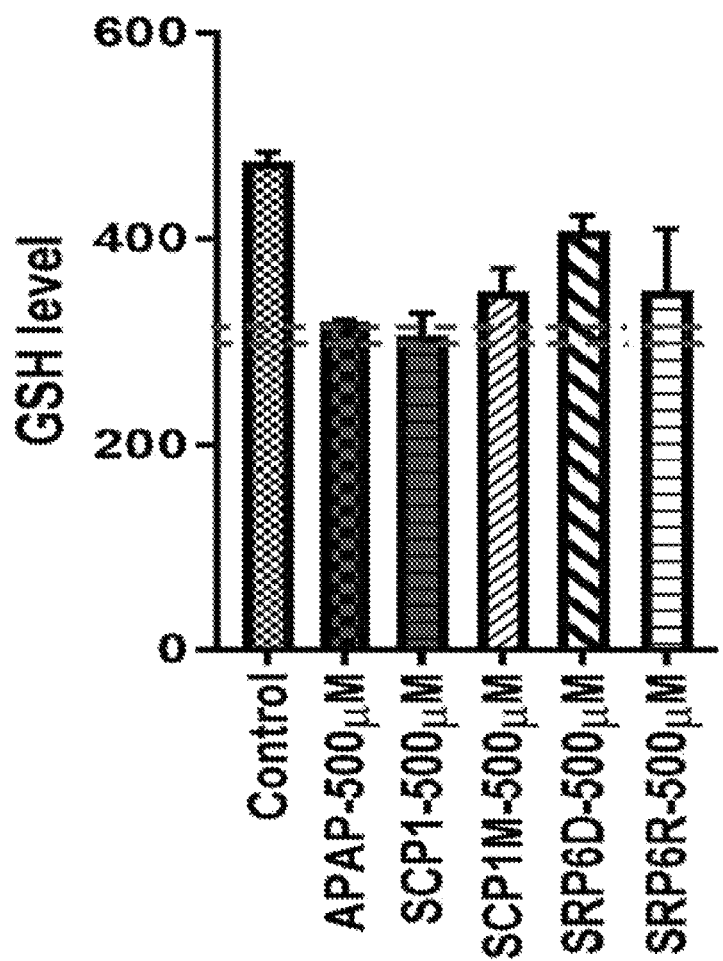
FIG. 2 shows hepatotoxicity assays in primary human hepatocytes (hHEPs) reveal decreased toxicity for novel compounds SRP6D, R, compared to ApAP and to first generation saccharin ApAP derivatives, SCP-1 and SCP-1M. For example, doses tested were 500 µM ApAP, SCP1, SCP1M, SRP6D and SRP6R.
Figure 3:
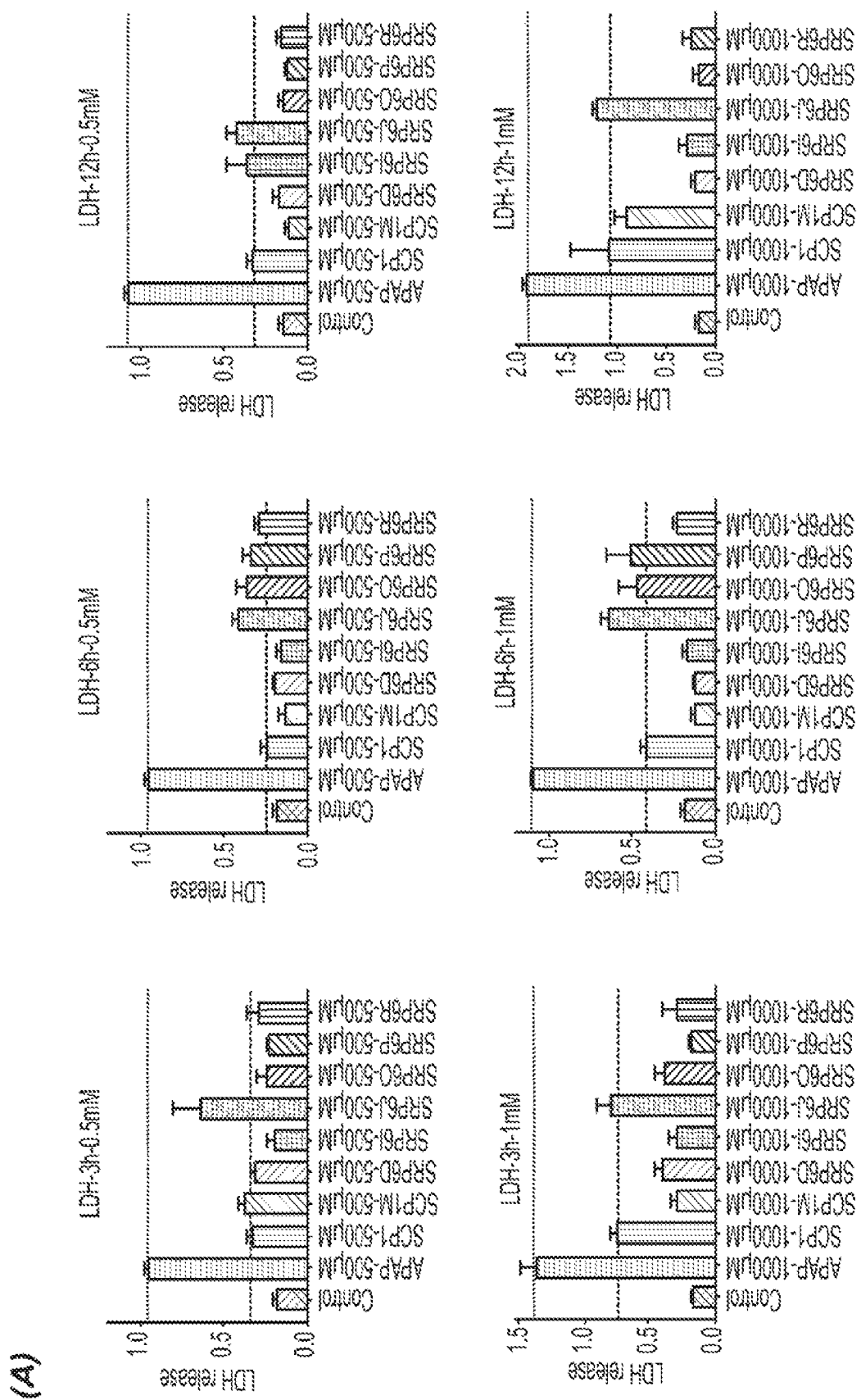
FIG. 3 shows hepatotoxicity assays in primary human hepatocytes (hHEPs), revealing decreased toxicity for novel compounds SRP6D and R, compared to ApAP and to first generation saccharin ApAP derivatives, SCP-1 and SCP-1M. A) Lactate dehydrogenase (LDH) release is increased and B) reduced glutathione (GSH) is decreased in hHEPs in a time and dose-dependent manner for ApAP but not for SRP6D and R. Doses tested in (A) and (B) were 500 µM (0.5 mM) and 1000 µM (1 mM). C) A marked reduction in liver function tests is noted for the SRP6D and R, compared to ApAP, the largest being in ALT. Dosage tested was 600 mg/kg.

Next, the hepatotoxicity profile for compounds SRP6D and R, compared to ApAP and to the first generation saccharin ApAP derivatives, SCP-1 and SCP-1M, was determined in both HepaRG and hHEPs. Decreased toxicity was noted for SRP6D and R, compared to ApAP: lactate dehydrogenase (LDH) release was consistently decreased and the amount of reduced glutathione (GSH) was increased for SRP6D and R, whereas ApAP led to an increased LDH release (FIG. 3) and depletion of GSH (FIG. 2) in a time and dose-dependent manner. In mouse liver and human hepatocytes (HepaRG and hHEP), at human equivalent therapeutic doses, a dose- and time-dependent effect of decreased hepatotoxicity thru decreased LDH and increased GSH release was observed with progressive clinical signs of liver injury for SRP6D and R but not ApAP. A marked reduction in liver function tests was noted for the SRP6D and R, compared to ApAP, the largest being in ALT. Increased levels of ALT, AST and AP enzyme activity for APAP was noted while SRP6D and R were similar to the control (vehicle only, FIG. 3C).

Figure 5:
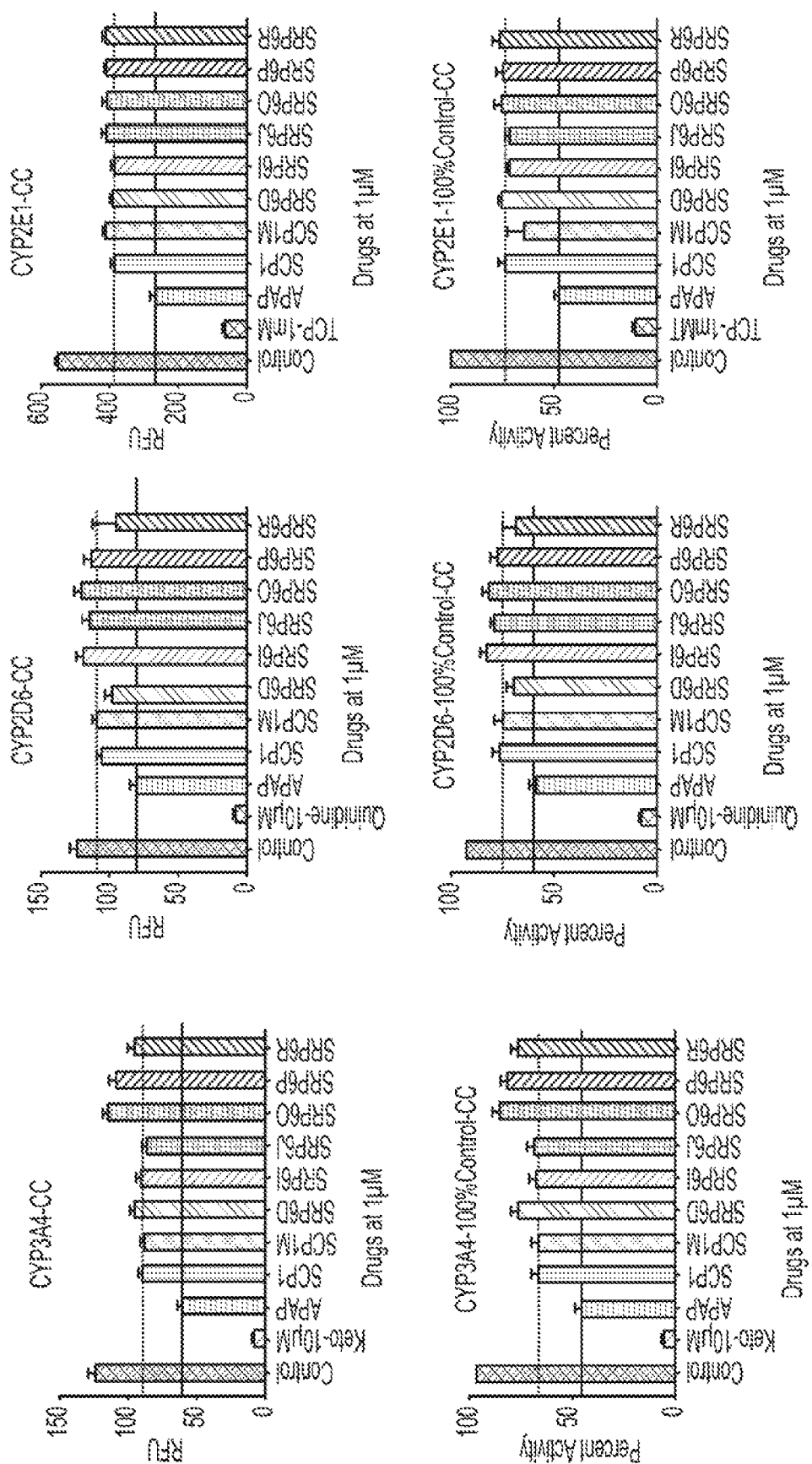
FIG. 5 shows favorable cytochrome P450 metabolism for SRP6D and SRP6R in various P450 isoenzymes. Red hash mark demonstrates the effect of ApAP and green hash mark denotes the first generation saccharin derivative of ApAP. Top panels are enzyme activities in relative fluorescence units and bottom panels are percent enzymatic activity.
Figure 6:
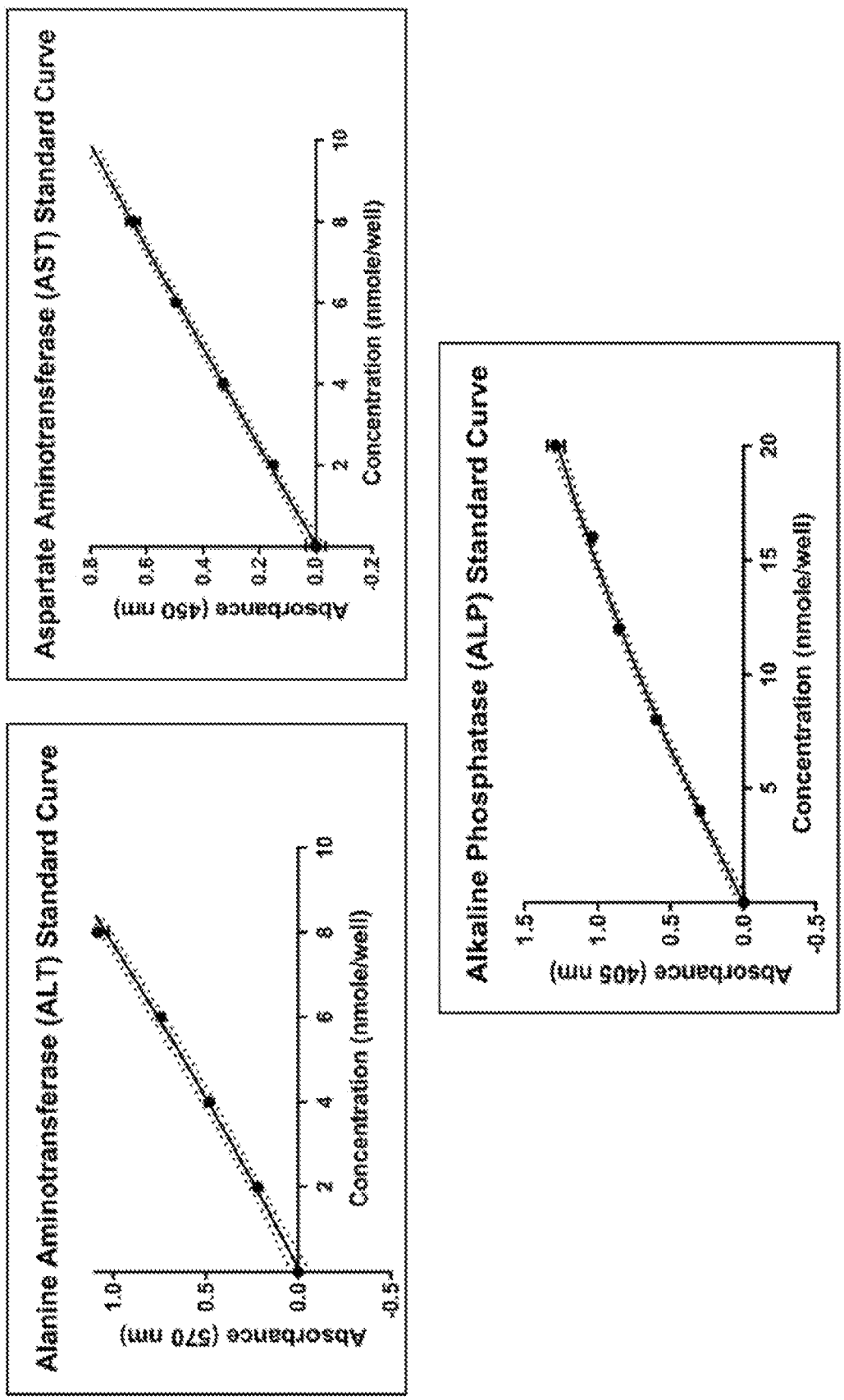
FIG. 6 shows standard curves for liver function tests (LFTs) for SRP compounds.
Figure 7:
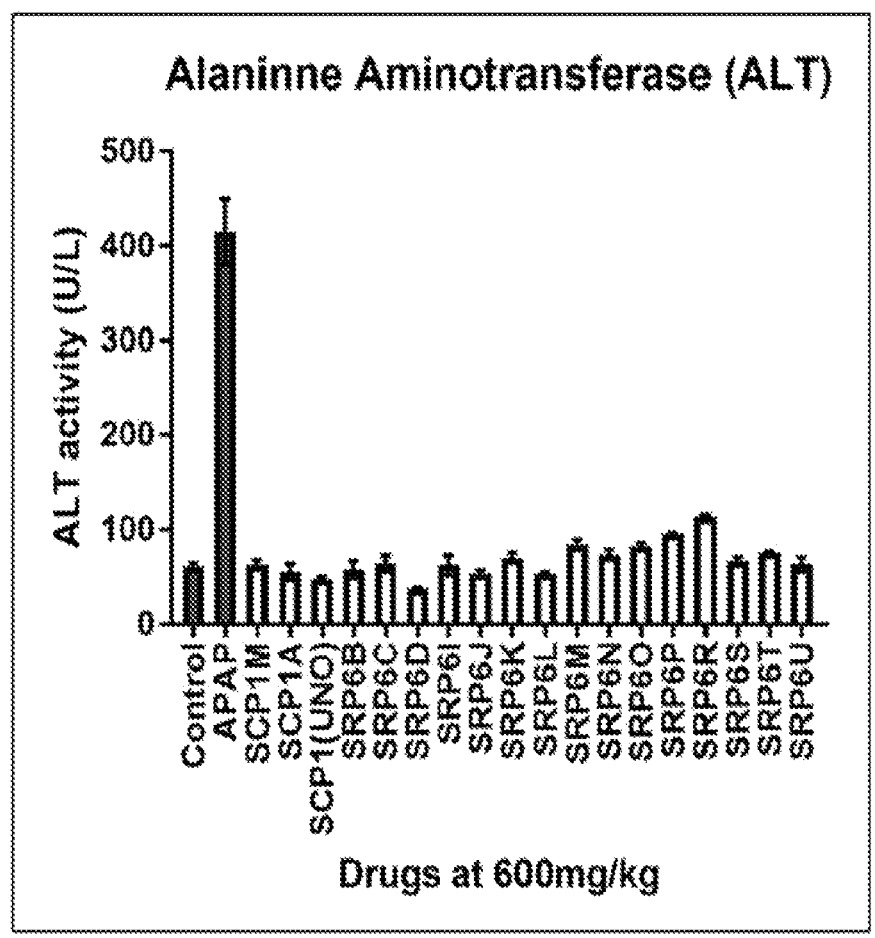
FIG. 7 shows liver function assays. (ALT, AST and ALP) were run after dosing CD1 male mice with 600 mg/kg of compounds—SRP compounds and APAP via PO (per os) (gavage). The assays were run with serum collected from mice injected with compounds or vehicle, after overnight (15 hours) fasting. After drug administration, water and food were provided to the mice ad libitum. The results showed increased levels of liver enzyme activity for APAP while, the other compounds were similar to the vehicle. LFT levels for the SRP compounds did not reach APAP levels.
Figure 8:
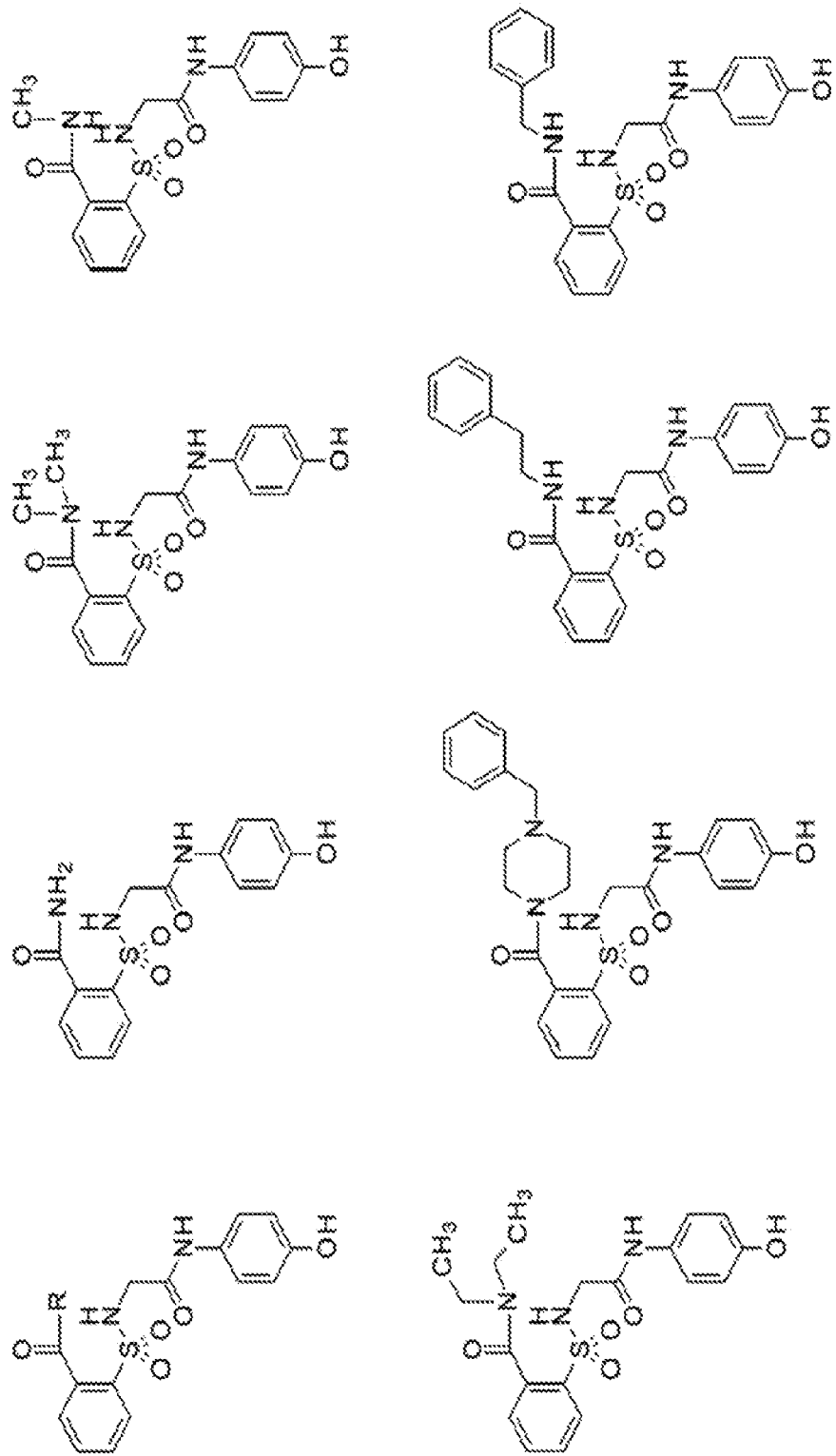
FIG. 8 shows chemical embodiments of the invention.
Figure 9:
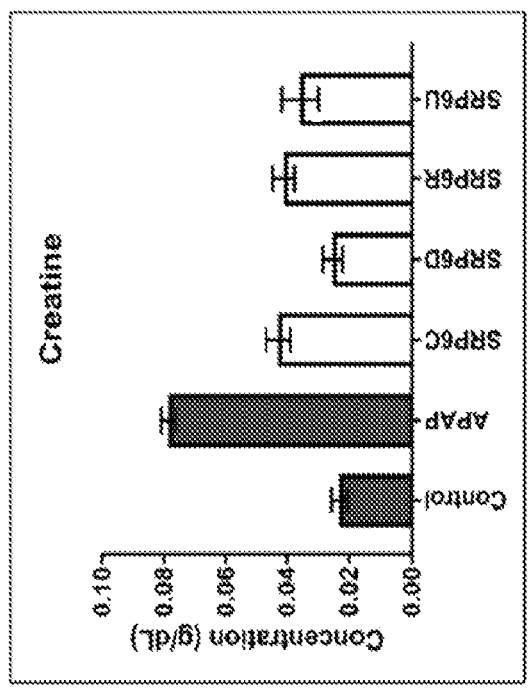
FIG. 9 shows functional assay to determine blood creatinine levels were run after dosing CD1 male mice with 600 mg/Kg (body weight) of compounds—SRP compounds and APAP via PO (per os) (gavage). The assays were run with serum collected from mice injected with compounds or vehicle, after overnight (15 hours) fasting. After drug administration, water and food were provided to the mice ad libitum. The results showed increased levels of creatinine for APAP while, SRP6D was similar to the vehicle. LFT levels for the other SRP compounds did not reach APAP levels.
Figure 9:
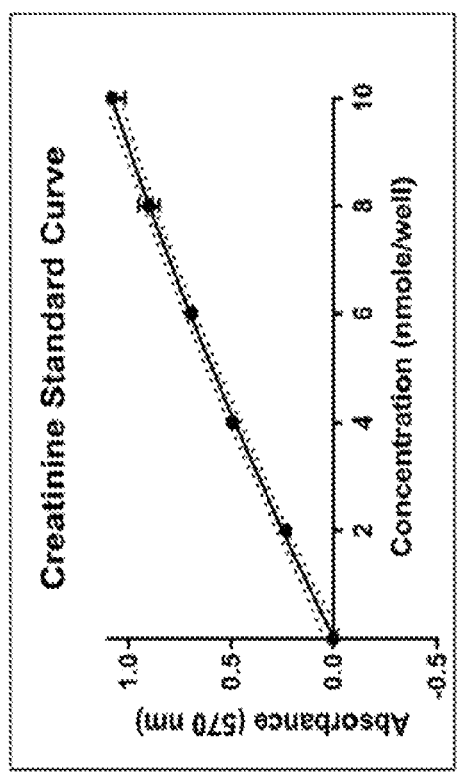

Lastly, a favorable cytochrome P450 metabolism for SRP6D and SRP6R was noted in various cytochrome P450 isoenzymes, including CYP3A4, CYP2D6, and CYP2E1. SRP6D and SRP6R only inhibit the activity of CYP2E1 and CYP3A4 by ~25% compared to 50% for ApAP and have a marginal inhibitory effect for CYP2D6 (FIG. 5).

Discussion

We demonstrate minimal hepatotoxicity in two novel compounds that are analogs to the metabolite of a saccharin derivative of ApAP. Using two well-accepted hepatic cells [18] hHEPs and HepaRGs as cell-based in vitro hepatic models, a consistent reduction in LDH release and increased reduced glutathione (GSH) release. These cells have the highest predictive capacity for ApAP-induced acute liver failure[19]. Reduced hepatotoxicity was further corroborated in an in vivo model. As ApAP hepatotoxicity mechanisms are similar in both humans and mice[20], we then chose the mouse to study clinical signs of liver injury (LFTs).

The in vitro toxicity assays utilized hHEPs and HepaRGs because they are the more reproducible for toxicology studies. Despite the inherent limits of primary cell cultures, including limited availability and a short life-span, hHEPs are the best cells available for in vitro hepatotoxicity assays [21]. There are intrinsic difficulties with a primary cell culture, however, and a recent toxigenomics analysis found that HepaRGs, a human hepatic cell line derived from hepatocellular carcinoma, expresses liver-specific genes at similar levels of hHEPs[19] and displays the best adult hepatocyte-like phenotype out of all available hepatic cell lines[18].

Though widely used as an over the counter analgesic worldwide, the main drawback of ApAP is its dose-dependent hepatotoxicity, which therapeutic index is further narrowed in individuals with compromised hepatic reserve. However, cases of unintentional or intentional overdosing may not be recognized in this short time period and ApAP remains the most common cause of acute fulminant hepatic failure in the United States[5], usually after advertent ingestion of large quantities or by consumption of over 3-4 grams per day in patients with impaired liver function. ApAP is available as a single-ingredient over the counter (OTC) medicine and in combination with other OTC medicines, including decongestants, and as prescription ApAP-opioid formulations. ApAP causing ALF likely occurs in unintentional cases when individuals ingest ApAP without knowledge of ApAP being present in these various formulations. In the United States around 30,000 patients are admitted to hospitals every year for the treatment of ApAP hepatotoxicity [22]. Although most patients experience only mild morbidity, such as hepatitis, cholestasis and a transient increase in liver transaminases, acute liver failure ensues in untreated patients ingesting large doses and may progress to convulsions, coma and death if not promptly recognized and treated. N-acetylcysteine (NAC) can prevent ApAP-hepatic injury by providing cysteine to restore GSH if given within 12 hours of ApAP overdose ingestion.

Another application of this technology could be to help curb the large opioid epidemic in the United States. In 2016, drug overdose deaths peaked at >65,000 cases, mostly due to opioid pain relievers and heroin. Workplace injuries may be driving many of these cases because there is evidence that prescribed oral narcotics are the likely source and two of the largest concentrations of overdose deaths are in Appalachia and the Southwest United States (CDC 2016).

NAPQI. APAP-induced hepatotoxicity is related to the formation of an electrophilic reactive metabolite, NAPQI, which is detoxified through conjugation with reduced glutathione (GSH). GSH is an important cellular antioxidant in the liver and GSH depletion is likely an important event in APAP-induced acute liver injury, although this mechanism is still poorly understood [23]. ApAP is metabolized by CYP enzymes, mainly CYP2E1 and CYP3A, to NAPQI. However, following a toxic dose, GSH depletion is followed by formation of reactive oxygen and nitrogen species leading to mitochondrial permeability and hepatocyte death [24]. A mechanism by which these compounds are minimally hepatotoxic may be because they do not generate NAPQI . . . (await this data).

REFERENCES IN THIS EXAMPLE

[1] W. Gamal, P. Treskes, K. Samuel, G. J. Sullivan, R. Siller, V. Srsen, K. Morgan, A. Bryans, A. Kozlowska, A.

Koulovasilopoulos, I. Underwood, S. Smith, J. Del-Pozo, S. Moss, A. I. Thompson, N.C. Henderson, P. C. Hayes, J. N. Plevris, P. O. Bagnaninchi, L. J. Nelson, Low-dose acetaminophen induces early disruption of cell-cell tight junctions in human hepatic cells and mouse liver, Scientific reports, 7 (2017) 37541.

[2] K. Brune, B. Renner, G. Tiegs, Acetaminophen/paracetamol: A history of errors, failures and false decisions, European journal of pain, 19 (2015) 953-965.

[3] A. Bertolini, A. Ferrari, A. Ottani, S. Guerzoni, R. Tacchi, S. Leone, Paracetamol: new vistas of an old drug, CNS Drug Rev, 12 (2006) 250-275.

[4] B. B. Brodie, J. Axelrod, The fate of acetanilide in man, The Journal of pharmacology and experimental therapeutics, 94 (1948) 29-38.

[5] A. M. Larson, J. Polson, R. J. Fontana, T. J. Davern, E. Lalani, L. S. Hynan, J. S. Reisch, F. V. Schiodt, G. Ostapowicz, A. O. Shakil, W. M. Lee, G. Acute Liver Failure Study, Acetaminophen-induced acute liver failure: results of a United States multicenter, prospective study, Hepatology, 42 (2005) 1364-1372.

[6] A. Reuben, H. Tillman, R. J. Fontana, T. Davern, B. McGuire, R. T. Stravitz, V. Durkalski, A. M. Larson, I Liou, O. Fix, M. Schilsky, T. McCashland, J. E. Hay, N. Murray, O. S. Shaikh, D. Ganger, A. Zaman, S. B. Han, R. T. Chung, A. Smith, R. Brown, J. Crippin, M. E. Harrison, D. Koch, S. Munoz, K. R. Reddy, L. Rossaro, R. Satyanarayana, T. Hassanein, A. J. Hanje, J. Olson, R. Subramanian, C. Karvellas, B. Hameed, A. H. Sherker, P. Robuck, W. M. Lee, Outcomes in Adults With Acute Liver Failure Between 1998 and 2013: An Observational Cohort Study, Annals of internal medicine, 164 (2016) 724-732.

[7] J. G. Bessems, N. P. Vermeulen, Paracetamol (acetaminophen)-induced toxicity: molecular and biochemical mechanisms, analogues and protective approaches, Crit Rev Toxicol, 31 (2001) 55-138.

[8] M. Ouellet, M. D. Percival, Mechanism of acetaminophen inhibition of cyclooxygenase isoforms, Archives of biochemistry and biophysics, 387 (2001) 273-280.

[9] R. J. Flower, J. R. Vane, Inhibition of prostaglandin synthetase in brain explains the anti-pyretic activity of paracetamol (4-acetamidophenol), Nature, 240 (1972) 410-411.

[10] E. D. Hogestatt, B. A. Jonsson, A. Ermund, D. A. Andersson, H. Bjork, J. P. Alexander, B. F. Cravatt, A. I. Basbaum, P. M. Zygmunt, Conversion of acetaminophen to the bioactive N-acylphenolamine AM404 via fatty acid amide hydrolase-dependent arachidonic acid conjugation in the nervous system, The Journal of biological chemistry, 280 (2005) 31405-31412.

[11] C. Mallet, D. A. Barriere, A. Ermund, B. A. Jonsson, A. Eschalier, P. M. Zygmunt, E. D. Hogestatt, TRPV1 in brain is involved in acetaminophen-induced antinociception, PloS one, 5 (2010).

[12] M. Dani, J. Guindon, C. Lambert, P. Beaulieu, The local antinociceptive effects of paracetamol in neuropathic pain are mediated by cannabinoid receptors, European journal of pharmacology, 573 (2007) 214-215.

[13] N. Fresno, R. Perez-Fernandez, C. Goicoechea, I. Alkorta, A. Femandez-Carvajal, R. de la Torre-Martinez, S. Quirce, A. Ferrer-Montiel, M. I. Martin, P. Goya, J. Elguero, Adamantyl analogues of paracetamol as potent analgesic drugs via inhibition of TRPA1, PloS one, 9 (2014) e113841.

[14] C. Sinning, B. Watzer, O. Coste, R. M. Nusing, I. Ott, A. Ligresti, V. Di Marzo, P. Imming, New analgesics synthetically derived from the paracetamol metabolite N-(4-hydroxyphenyl)-(5Z,8Z,11Z,14Z)-icosatetra-5,8,11,14-enamide, Journal of medicinal chemistry, 51 (2008) 7800-7805.

[15] A. L. Vaccarino, D. Paul, P. K. Mukherjee, E. B. Rodriguez de Turco, V. L. Marcheselli, L. Xu, M. L. Trudell, J. M. Minguez, M. P. Matia, C. Sunkel, J. Alvarez-Builla, N. G. Bazan, Synthesis and in vivo evaluation of non-hepatotoxic acetaminophen analogs, Bioorg Med Chem, 15 (2007) 2206-2215.

[16] J. G. Cui, X. Zhang, Y. H. Zhao, C. Chen, N. Bazan, Allodynia and hyperalgesia suppression by a novel analgesic in experimental neuropathic pain, Biochemical and biophysical research communications, 350 (2006) 358-363.

[17] L. Miao, L. Xu, K. W. Narducy, M. L. Trudell, First Multi-gram Preparation SCP-123, A Novel Water Soluble Analgesic, Org Process Res Dev, 13 (2009) 820.

[18] M. Santoh, S. Sanoh, Y. Ohtsuki, Y. Ejiri, Y. Kotake, S. Ohta, Acetaminophen analog N-acetyl-m-aminophenol, but not its reactive metabolite, N-acetyl-p-benzoquinone imine induces CYP3A activity via inhibition of protein degradation, Biochemical and biophysical research communications, 486 (2017) 639-644.

[19] R. M. Rodrigues, A. Heymans, V. De Boe, A. Sachinidis, U. Chaudhari, O. Govaere, T. Roskams, T. Vanhaecke, V. Rogiers, J. De Kock, Toxicogenomics-based prediction of acetaminophen-induced liver injury using human hepatic cell systems, Toxicology letters, 240 (2016) 50-59.

[20] M. R. McGill, C. D. Williams, Y. Xie, A. Ramachandran, H. Jaeschke, Acetaminophen-induced liver injury in rats and mice: comparison of protein adducts, mitochondrial dysfunction, and oxidative stress in the mechanism of toxicity, Toxicology and applied pharmacology, 264 (2012) 387-394.

[21] E. L. LeCluyse, R. P. Witek, M. E. Andersen, M. J. Powers, Organotypic liver culture models: meeting current challenges in toxicity testing, Crit Rev Toxicol, 42 (2012) 501-548.

[22] M. Blieden, L. C. Paramore, D. Shah, R. Ben-Joseph, A perspective on the epidemiology of acetaminophen exposure and toxicity in the United States, Expert Rev Clin Pharmacol, 7 (2014) 341-348.

[23] M. A. Abdelmegeed, K. H. Moon, C. Chen, F. J. Gonzalez, B. J. Song, Role of cytochrome P450 2E1 in protein nitration and ubiquitin-mediated degradation during acetaminophen toxicity, Biochemical pharmacology, 79 (2010) 57-66.

[24] J. A. Hinson, A. B. Reid, S. S. McCullough, L. P. James, Acetaminophen-induced hepatotoxicity: role of metabolic activation, reactive oxygen/nitrogen species, and mitochondrial permeability transition, Drug Metab Rev, 36 (2004) 805-822.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:
1. An analgesic composition of formula (I):

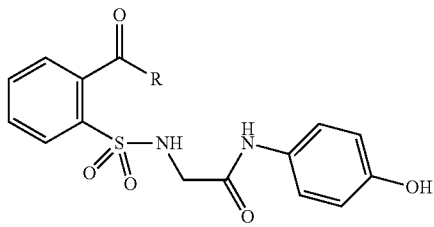

wherein R is selected from the group consisting of $NH_2$, $N(CH_3)_2$, $NHCH_3$, $N(CH_2CH_3)_2$, $N_2(CH_2)_4CH_2C_6H_5$, $NH(CH_2)_2C_6H_5$, $NHCH_2C_6H_5$, $NO(CH_2)_4$, $NHCH_2CH_2CH_2CH_3$, $NHCH_2C_6H_4CH_3O$, $NHCH_2C_6H_3Cl_2$, $NHCH_2C_6H_5CH_3$, $NHCH_2C_6H_4Cl$, $NHCH_2C_6H_4NO_2$, $NHC_5H_9$, $NHCH_2CH(CH_3)_2$, $NHCH(CH_3)_2$, $NHCH_2C_6H_3(OH)_2$, $NHCH_2C_5H_4N$, $NHC_5H_3NCH_3$, $NHCH_2CH_2C_4H_8N$, $N(CH_3)CH_2CH_2OH$, $NHCH_2CH(OH)CH_2NH_2$, $NHR^1$, and $NR^1R^2$, wherein $R^1$ is selected from the group consisting of H, OH, $CH_3$, $CH_2CH_3$, $(CH_2)_2C_6H_5$, $CH_2C_6H_5$, $CH_2CH_2CH_2CH_3$, $CH_2C_6H_4OH$, $CH_2C_6H_3Cl_2$, $CH_2C_6H_4CH_3$, $CH_2C_6H_4Cl$, $CH_2C_6H_4NO_2$, $C_5H_9$, $CH_2CH(CH_3)_2$, $CH(CH_3)_2$, $CH_2CH_2C_6H_3(OH)_2$, $CH_2C_5H_4N$, $CH_2C_5H_3NCH_3$, $CH_2CH_2C_4H_8N$, $CH_2CH_2OH$, $CH_2CH(OH)CH_2NH_2$, an alkyl group, a haloalkyl group, a halobenzyl group, a phenyl group, —O-(alkyl), —O-(haloalkyl), —O-(halobenzyl), —O-(phenyl), an alkyl phenyl, a haloalkyl-phenyl, an alkyl-halobenzene, an alkyl-nitrobenzene, —O-(alkyl phenyl), —O-(haloalkyl)-phenyl, and a cycloalkane group, and wherein $R^2$ is selected from the group consisting of H, $CH_3$, and an alkyl group; wherein the alkyl group comprises C1-C10 carbons, the halo group comprises F, Br, or Cl, and wherein the cycloalkane group comprises a 5 or 6 membered ring; or a pharmaceutically acceptable salt thereof.

2. The analgesic composition of claim 1 having a chemical structure selected from the group consisting of:

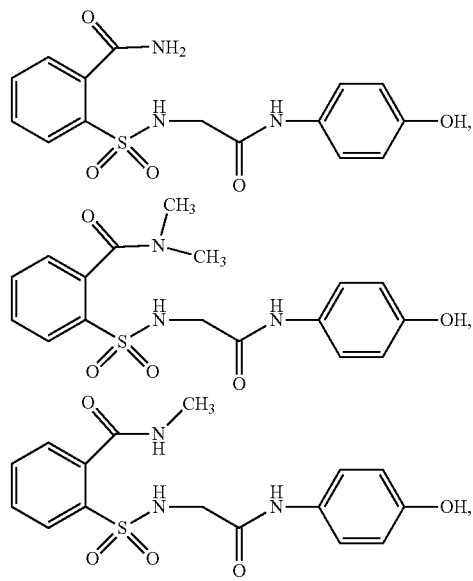

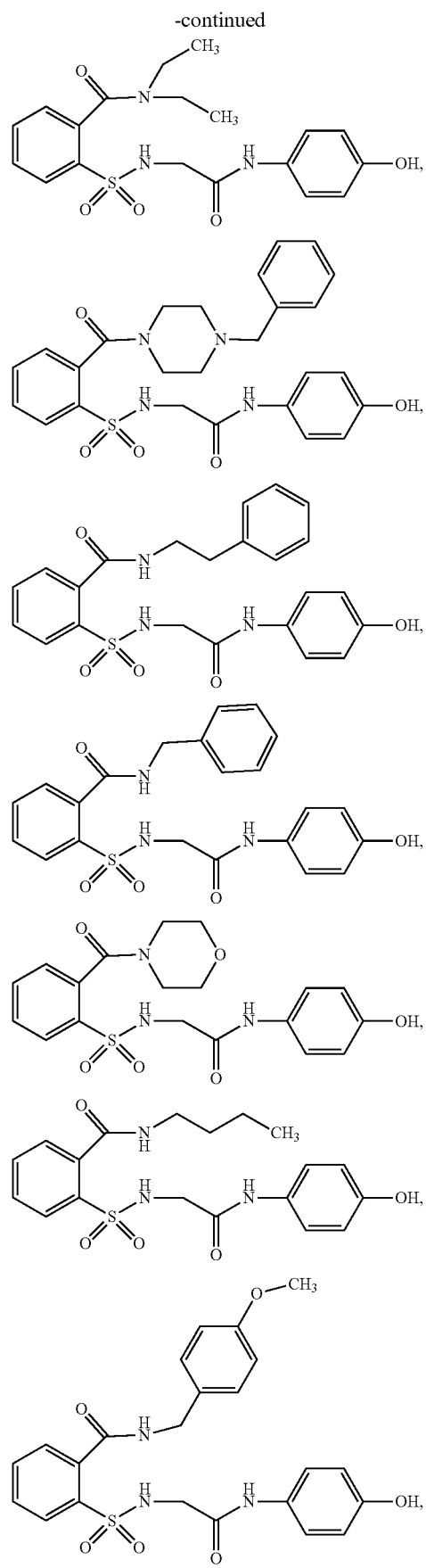

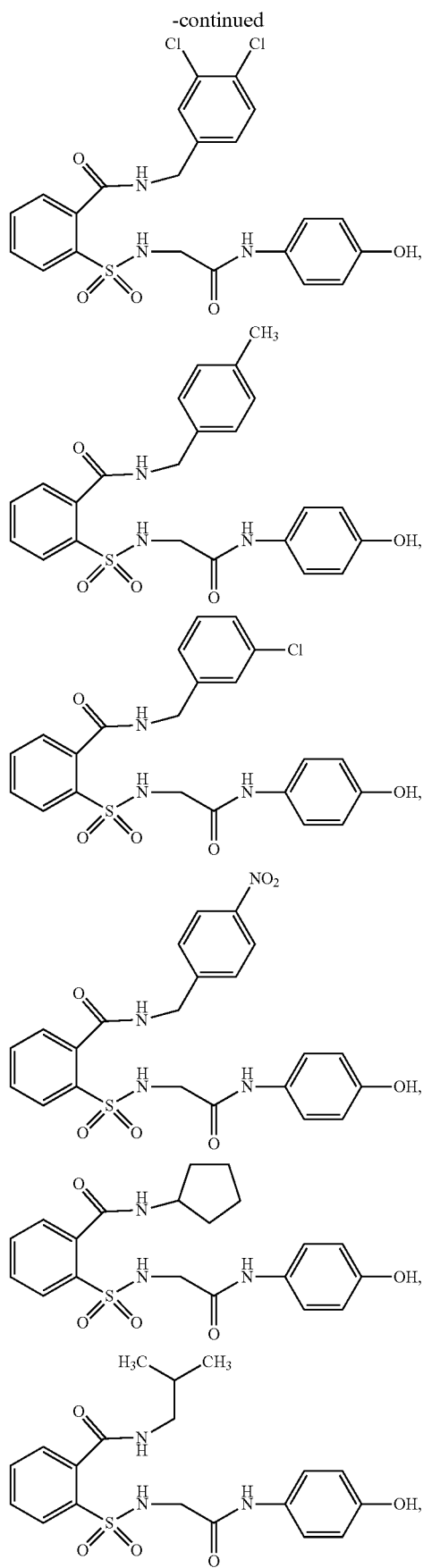
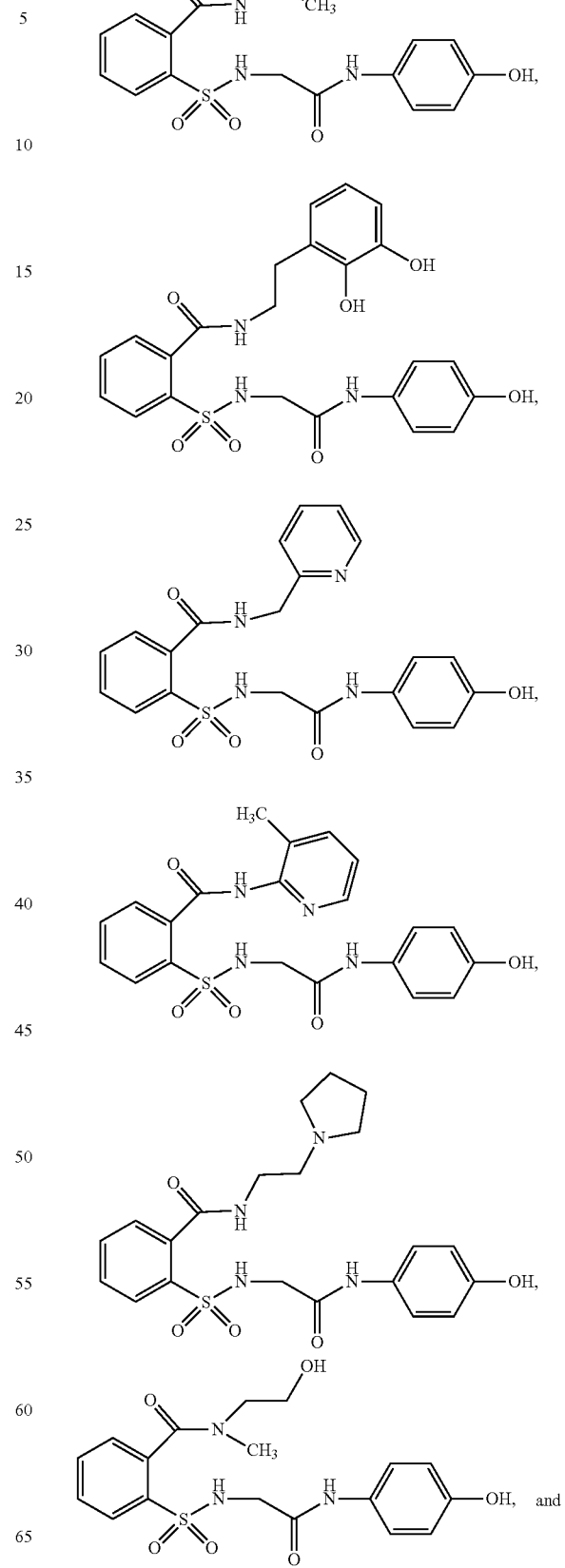

-continued

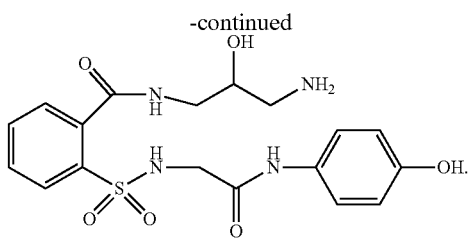

3. The analgesic composition of claim 1, wherein said composition has a reduced risk of hepatotoxicity when administered in vivo.

4. A method of alleviating pain in a subject, the method comprising administering to said subject afflicted with pain a therapeutically effective amount of the analgesic composition of claim 1.

5. A method of preventing pain in a subject, the method comprising administering to said subject afflicted with pain a therapeutically effective amount of the analgesic composition of claim 1.

6. A method of ameliorating pain in a subject, the method comprising administering to said subject afflicted with pain a therapeutically effective amount of the analgesic composition of claim 1.

7. A method of reducing the incidence of pain in a subject, the method comprising administering to said subject afflicted with pain a therapeutically effective amount of the analgesic composition of claim 1.

8. A method of delaying the development of pain in a subject, the method comprising administering to said subject afflicted with pain a therapeutically effective amount of the analgesic composition of claim 1.

9. A method of preventing the development of pain in a subject, the method comprising administering to said subject afflicted with pain a therapeutically effective amount of the analgesic composition of claim 1.

10. A method of palliating pain in a subject, the method comprising administering to said subject afflicted with pain a therapeutically effective amount of the analgesic composition of claim 1.

11. The method of claim 4, wherein pain comprises neuropathic pain, nociceptive pain, or a combination thereof.

12. The method of claim 11, wherein the neuropathic pain comprises post-surgical pain, neuropathic pain, dental pain, ophthalmic pain, arthritic pain, post- and/or traumatic pain, or a combination thereof.

13. The method of claim 4, wherein the therapeutically effective amount comprises a dose of about 10 μM to about 10 mM of the composition is administered to the subject.

14. The method of claim 4, wherein the composition is administered in a single dose.

15. The method of claim 4, wherein the composition is administered at intervals of about 4 hours, 12 hours, or 24 hours.

16. The method of claim 4, wherein the composition is administered orally, parentally, transdermally, or nasally.

17. The method of claim 4, wherein the composition is administered in the form of a pill, capsule, cream, spray, lotion, or aqueous solution.

18. The method of claim 4, wherein the composition exhibits analgesia, antipyresis, or a combination thereof.

19. The method of claim 4, wherein the composition reduces the risk of hepatotoxicity by at least about 20%.

20. The method of claim 4, further comprising administering concurrently or subsequently a therapeutically effective amount of an opioid and/or NSAID to the subject.

21. The method of claim 4, wherein the composition is not metabolized to NAPQI.

22. A medical kit for the treatment of pain, the kit comprising: printed instructions for administering the composition to the subject afflicted with pain; an analgesic composition of claim 1.

23. A pharmaceutical composition comprising an analgesic composition of claim 1.

* * * * *